(12) United States Patent
Luxon et al.

(10) Patent No.: US 10,772,998 B2
(45) Date of Patent: Sep. 15, 2020

(54) SYSTEMS, DEVICES AND METHODS FOR DRAINING AND ANALYZING BODILY FLUIDS

(71) Applicant: Potrero Medical, Inc.

(72) Inventors: Evan S. Luxon, Lincoln, NE (US); Marcie Hamilton, San Francisco, CA (US); Daniel R. Burnett, San Francisco, CA (US); Mark Ziegler, Palo Alto, CA (US)

(73) Assignee: Potrero Medical, Inc., Hayward, CA (US)

( * ) Notice: Subject to any disclaimer, the term of this patent is extended or adjusted under 35 U.S.C. 154(b) by 489 days.

(21) Appl. No.: 15/201,156

(22) Filed: Jul. 1, 2016

(65) Prior Publication Data

US 2016/0310711 A1    Oct. 27, 2016

Related U.S. Application Data

(63) Continuation of application No. PCT/US2015/010530, filed on Jan. 7, 2015.
(Continued)

(51) Int. Cl.
*A61M 1/00* (2006.01)
*A61M 25/00* (2006.01)
*A61B 5/20* (2006.01)

(52) U.S. Cl.
CPC ........... *A61M 1/0033* (2014.02); *A61B 5/208* (2013.01); *A61M 25/0017* (2013.01);
(Continued)

(58) Field of Classification Search
CPC ...... A61M 25/0026; A61M 27/00–008; A61M 1/0025; A61M 1/0001–0017; A61B 5/208
See application file for complete search history.

(56) References Cited

U.S. PATENT DOCUMENTS

| | | | |
|---|---|---|---|
| 1,444,565 | A | 2/1923 | Smith |
| 3,730,209 | A | 5/1973 | Binard et al. |

(Continued)

FOREIGN PATENT DOCUMENTS

| | | |
|---|---|---|
| WO | WO 2003/024330 | 3/2003 |
| WO | WO 2004/037334 | 5/2004 |

(Continued)

*Primary Examiner* — Susan S Su
(74) *Attorney, Agent, or Firm* — Levine Bagade Han LLP

(57) ABSTRACT

A device for draining bodily fluids is described herein which generally may comprise an elongate body defining one or more lumens configured to receive a bodily fluid from a cavity, e.g., bladder, of a patient body. The one or more lumens are in fluid communication with a reservoir which may receive the bodily fluid. A pumping mechanism may be used to urge the bodily fluid through the one or more lumens, where the pumping mechanism is configured to maintain an open space within the one or more lumens such that outflow of the bodily fluid through the one or more lumens remains unobstructed such that a negative pressure buildup in the cavity is inhibited. The device may also include a vent or valve mechanism in communication with the elongate body to allow air to enter or exit the one or more lumens.

34 Claims, 43 Drawing Sheets

Related U.S. Application Data

(60) Provisional application No. 61/924,529, filed on Jan. 7, 2014, provisional application No. 61/937,597, filed on Feb. 9, 2014.

(52) U.S. Cl.
CPC ....... *A61M 1/0066* (2013.01); *A61M 25/0026* (2013.01); *A61M 2205/50* (2013.01); *A61M 2205/502* (2013.01); *A61M 2205/52* (2013.01)

(56) References Cited

U.S. PATENT DOCUMENTS

| | | | |
|---|---|---|---|
| 3,851,650 A | 12/1974 | Darling | |
| 4,535,786 A | 8/1985 | Kater | |
| 5,222,008 A | 6/1993 | Yamagishi et al. | |
| 5,411,472 A * | 5/1995 | Steg, Jr. | A61M 1/0031 604/6.11 |
| 5,573,007 A | 11/1996 | Bobo, Sr. | |
| 5,704,353 A | 1/1998 | Kalb et al. | |
| 5,738,656 A | 4/1998 | Wagner | |
| 6,017,493 A | 1/2000 | Cambron et al. | |
| 6,210,346 B1 * | 4/2001 | Hall | A61B 5/031 600/561 |
| 6,342,048 B1 * | 1/2002 | Verkaart | A61J 1/05 604/323 |
| 6,434,418 B1 | 8/2002 | Neal et al. | |
| 6,447,462 B1 | 9/2002 | Wallace et al. | |
| 6,673,022 B1 | 1/2004 | Bobo et al. | |
| 6,935,999 B2 | 8/2005 | Schock et al. | |
| 7,004,899 B2 | 2/2006 | Tracey | |
| 7,112,170 B2 | 9/2006 | Schock et al. | |
| 7,229,403 B2 | 6/2007 | Schock et al. | |
| 7,524,315 B2 | 4/2009 | Blott et al. | |
| 7,739,907 B2 | 6/2010 | Boiarski | |
| 7,883,494 B2 | 2/2011 | Martin | |
| 7,892,217 B2 | 2/2011 | Boiarski | |
| 7,931,630 B2 | 4/2011 | Nishtala et al. | |
| 7,938,817 B2 | 5/2011 | Gelfand et al. | |
| 7,947,001 B1 | 5/2011 | Sarvazyan | |
| 7,976,533 B2 | 7/2011 | Larsson | |
| 8,066,681 B1 * | 11/2011 | Hall | A61B 5/031 600/561 |
| 8,157,775 B2 | 4/2012 | Bobroff et al. | |
| 8,192,368 B2 | 6/2012 | Woodruff et al. | |
| 8,403,884 B2 | 3/2013 | Nishtala | |
| 8,424,376 B2 | 4/2013 | Boiarski | |
| 8,486,051 B2 | 7/2013 | Larsson | |
| 8,491,550 B2 | 7/2013 | Ramella et al. | |
| 8,568,387 B2 | 10/2013 | Paz | |
| 8,715,254 B2 | 5/2014 | Nishtala | |
| 8,801,684 B2 | 8/2014 | Walti et al. | |
| 8,813,551 B2 | 8/2014 | Boiarski | |
| 8,827,924 B2 | 9/2014 | Paz et al. | |
| 8,953,159 B2 | 2/2015 | Cunningham et al. | |
| 9,216,242 B2 | 12/2015 | Nishtala et al. | |
| 2003/0138349 A1 * | 7/2003 | Robinson | A61M 1/02 422/44 |
| 2004/0184953 A1 * | 9/2004 | Litzie | A61M 1/3629 422/45 |
| 2006/0100743 A1 | 5/2006 | Townsend et al. | |
| 2006/0271019 A1 * | 11/2006 | Stoller | A61F 5/44 604/544 |
| 2007/0010798 A1 | 1/2007 | Stoller et al. | |
| 2008/0015434 A1 | 1/2008 | Rubinstein et al. | |
| 2008/0117416 A1 | 5/2008 | Hunter et al. | |
| 2008/0312550 A1 | 12/2008 | Nishtala et al. | |
| 2009/0149776 A1 | 6/2009 | Adams | |
| 2010/0094173 A1 * | 4/2010 | Denton | A61M 1/0043 600/584 |
| 2010/0130949 A1 | 5/2010 | Garcia | |
| 2010/0137743 A1 | 6/2010 | Nishtala et al. | |
| 2010/0286667 A1 * | 11/2010 | Paz | A61M 1/0019 604/544 |
| 2011/0060300 A1 * | 3/2011 | Weig | A61F 5/451 604/319 |
| 2011/0208026 A1 | 8/2011 | Goodall et al. | |
| 2011/0257576 A1 * | 10/2011 | Simpson | A61M 1/3666 604/4.01 |
| 2012/0035595 A1 | 2/2012 | Goedje et al. | |
| 2013/0172840 A1 * | 7/2013 | Lampotang | A61M 1/0021 604/328 |
| 2013/0218106 A1 | 8/2013 | Coston et al. | |
| 2014/0074071 A1 | 3/2014 | Paz | |
| 2014/0194835 A1 | 7/2014 | Ehlert | |
| 2014/0316219 A1 | 10/2014 | Paz et al. | |
| 2015/0362351 A1 | 12/2015 | Joshi et al. | |
| 2016/0123998 A1 * | 5/2016 | MacIntyre | A61B 5/02042 436/66 |
| 2016/0183819 A1 | 6/2016 | Burnett et al. | |
| 2016/0310711 A1 | 10/2016 | Luxon et al. | |
| 2017/0030758 A1 | 2/2017 | Joshi | |
| 2017/0100068 A1 | 4/2017 | Kostov | |
| 2017/0138027 A1 | 5/2017 | Chuang | |
| 2019/0041405 A1 * | 2/2019 | Macintyre | A61M 1/0001 |

FOREIGN PATENT DOCUMENTS

| | | |
|---|---|---|
| WO | WO 2006/046060 | 8/2006 |
| WO | WO 2009/142508 | 11/2009 |
| WO | WO 2012/016179 | 2/2012 |
| WO | WO 2012/033906 | 3/2012 |
| WO | WO 2015/105916 | 7/2015 |
| WO | WO 2015/192054 | 12/2015 |
| WO | WO 2015/192108 | 12/2015 |

\* cited by examiner

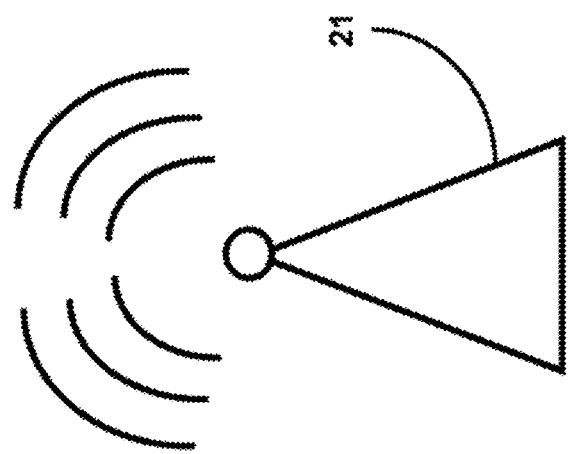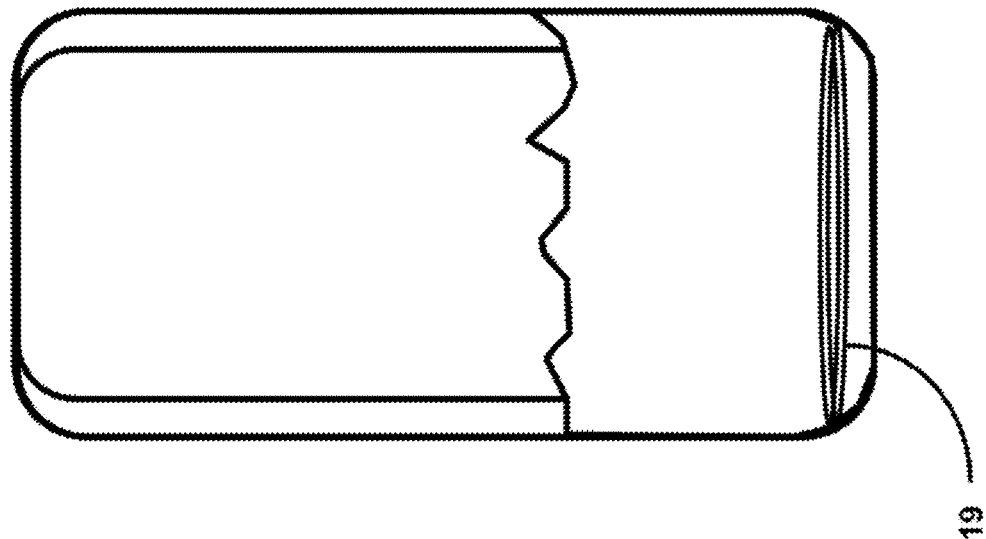
Fig. 5

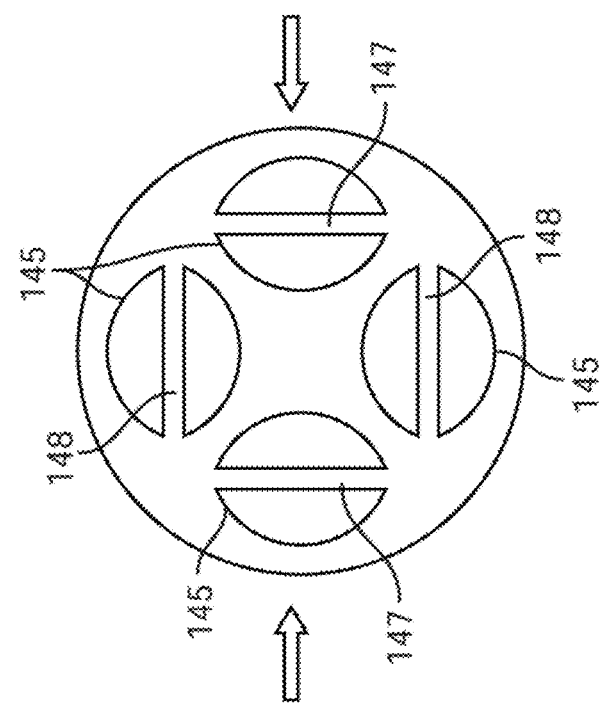
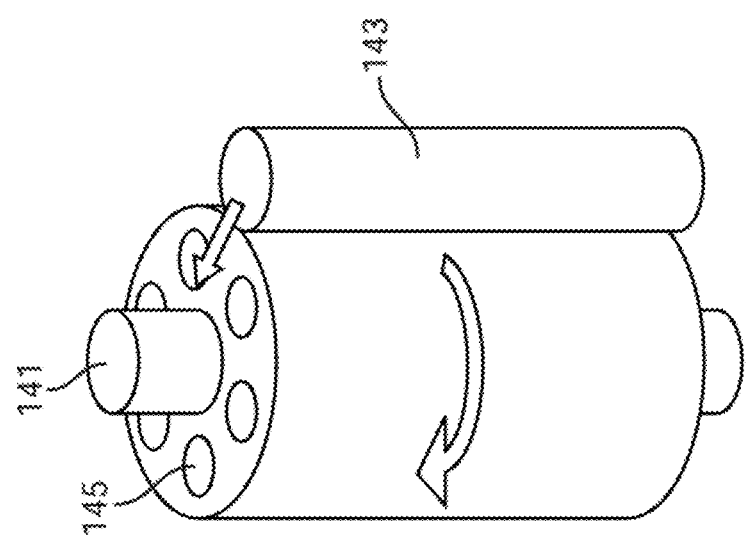

|  | Drain Line Status | |
|---|---|---|
|  | Backpressure: Handrail w/ air lock | Siphon: Handrail w/o air lock |
| Bard® & AbViser™ Intermittent (pressure transducer w/ valve) | +20.7<br>False Positive | -0.9<br>Accurate |
| Bard® & AbViser™ Continuous (pressure transducer w/o valve) | +12.9<br>False Positive | -19.5<br>False Negative |
| Theranova Accuryn™ | -0.3<br>Accurate | -0.3<br>Accurate |

FIG. 13

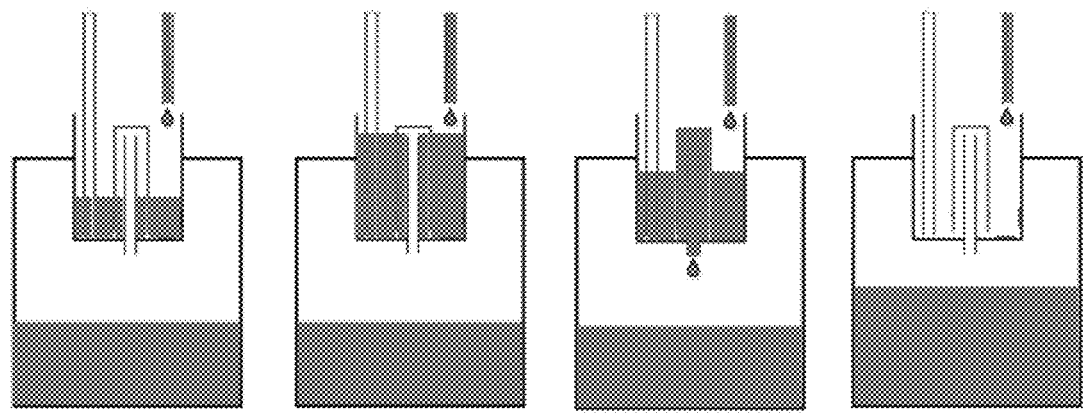
FIG. 19A   FIG. 19B   FIG. 19C   FIG. 19D
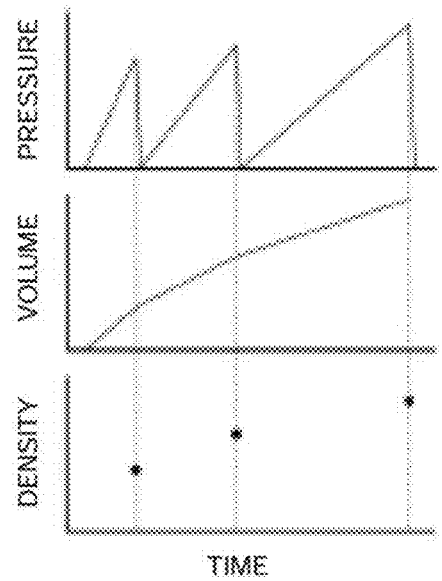
FIG. 20
| Parameter | Condition | | | |
|---|---|---|---|---|
| | AKI | | | UTI |
| | Prerenal | Intrinsic | Postrenal | |
| Urine Oxygen Tension | ↓ then ↑ | ↓ then ↑ | - | ↓↓ |
| Urine Output | ↓ | ↓↓ | ↓↓↓ | - |
| Urine Conductance | ↓ | ↑↑ | ↑↑ | - |
| Specific Gravity | ↑ | ↓ | - | ↑ |
FIG. 21

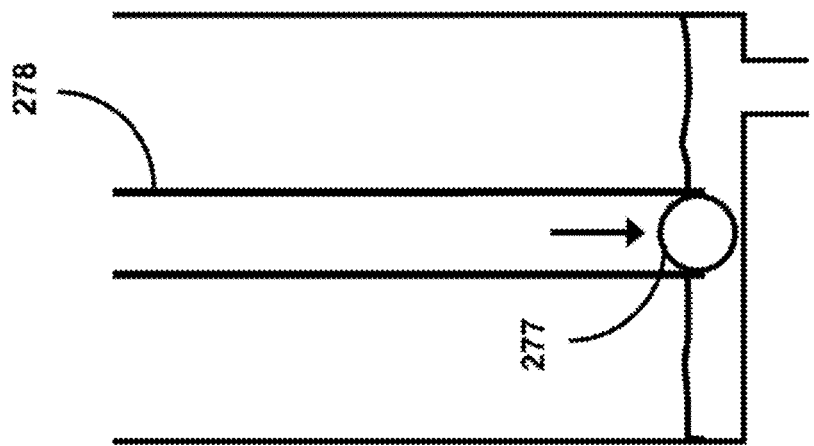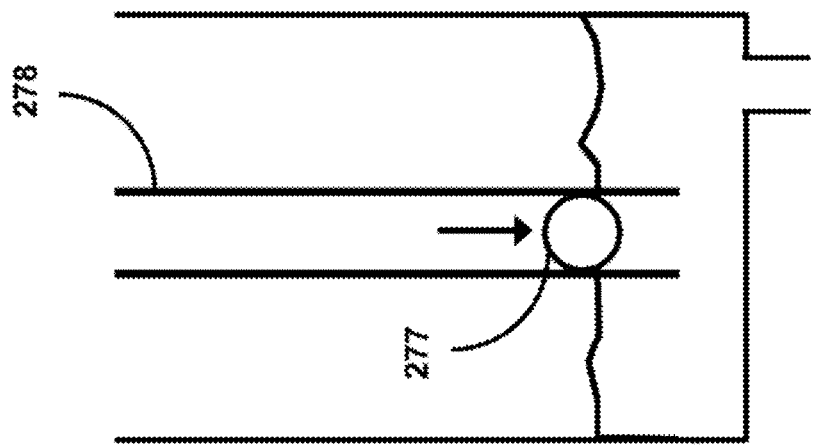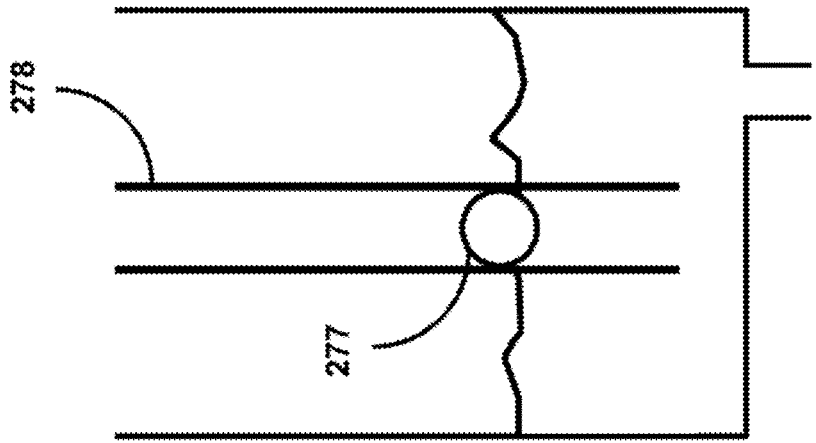
FIG. 33

SYSTEMS, DEVICES AND METHODS FOR DRAINING AND ANALYZING BODILY FLUIDS

CROSS-REFERENCE TO RELATED APPLICATIONS

This application is a continuation of International Application No. PCT/US2015/010530 filed Jan. 7, 2015, which claims the benefit of priority to U.S. Provisional Application No. 61/924,529 filed Jan. 7, 2014 and U.S. Provisional Application No. 61/937,597 filed Feb. 9, 2014, each of which is incorporated herein by reference in its entirety.

TECHNICAL FIELD OF THE INVENTION

The present invention relates to the field of medical devices, in particular devices that aid emptying of the bladder, measure urine output and various urine parameters such as oxygen tension, urine conductance and urine specific gravity, monitor renal function, analyze urine content, and track fluid administration. The present invention further relates to medical devices capable of sensing physiologic data based on sensors incorporated into a catheter or implant adapted to reside in any of a urinary tract, gastrointestinal tract, rectal location, pre-peritoneal or other implanted site.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

It is estimated that 10% of all hospitalized and long-term care patients receive an in-dwelling urethral catheter. Almost all critically ill patients receive one, and in the ICU it is routine procedure to monitor urine output every hour. The amount of urine produced is an indicator of fluid status and renal function. However, numerous sources of error can cause erroneous measurements of this important indicator.

The most common device used to drain the bladder is the Foley catheter. Since its introduction the design of a flexible tube with an anchoring balloon and eyelets that allow urine to drain through a central lumen has remained largely unchanged. However, it has been found that the current design of Foley catheters can result in a large residual volume remaining in the bladder, for example greater than 50 mL in supine patients. See Fallis, Wendy M. Indwelling Foley Catheters Is the Current Design a Source of Erroneous Measurement of Urine Output? Critical Care Nurse 25.2 (2005): 44-51. In one study, mean residual volume was 96 mL in the ICU and 136 mL in the general ward. See. Garcia et al., Traditional Foley Drainage Systems—Do They Drain the Bladder?, J Urol. 2007 January; 177(1):203-7; discussion 207. A large residual volume of urine is also often found in the drain tube that connects the Foley catheter to the drainage bag.

The residual urine in the bladder and drain tube is a result of large air bubbles (air locks) that are formed in the tube and prevent the flow of urine from the bladder to the drainage bag. As a result, it has become routine procedure for nurses to manipulate the drainage tube prior to measuring urinary output, which helps empty the tubing. In the ICU, where measurements are made as often as every hour, this is a very repetitive and imprecise process.

In addition, the development of air locks has been found by the inventors to significantly skew intra-abdominal pressure readings (Burnett, D R. Luxon, E S, Hamilton, M H. Preventing Inaccurate Intra-Abdominal Pressure Readings Due to Air-Locks and Siphon Effects in Urinary Drainage Lines. Int J Abd Res. 1(1). 2013, p 91). This has not been recognized by the clinical community as an issue and another of our innovations is the detection and removal of air locks in the setting of intra-abdominal pressure measurements.

SUMMARY OF THE INVENTION

The present invention seeks to more effectively drain the bladder, prevent airlocks from forming in the drainage tube and clearing them when they do, and increase the accuracy with which urine output is measured in an automated way. The invention also seeks to incorporate additional measurements of the urine, including oxygen tension, conductance, and specific gravity, to improve the monitoring of fluid status, renal function, and other important patient parameters.

Generally, one example of such a device for draining bodily fluids may comprise an elongate body defining one or more lumens configured to receive a bodily fluid from a cavity, e.g., bladder, of a patient body. The one or more lumens are in fluid communication with a reservoir which may receive the bodily fluid. A pumping mechanism may be used to urge the bodily fluid through the one or more lumens, where the pumping mechanism is configured to maintain an open space within the one or more lumens such that outflow of the bodily fluid through the one or more lumens remains unobstructed such that a negative pressure buildup in the cavity is inhibited. The device may also include a vent or valve mechanism in communication with the elongate body to allow air to enter or exit the one or more lumens.

Generally in use, the elongate body may be positioned within a cavity of a patient body such that the one or more lumens receive a bodily fluid from the cavity and the pumping mechanism may be used to urge the bodily fluid through the one or more lumens from the cavity while maintaining an open space within the one or more lumens such that outflow of the bodily fluid through the one or more lumens remains unobstructed and negative pressure buildup within the cavity is inhibited. Air may be allowed to flow into or from the one or more lumens via the vent or valve mechanism in communication with the elongate body and the bodily fluid may be received in the reservoir which is in fluid communication with the one or more lumens.

According to one aspect, the present invention relates to a device for draining bodily fluids, comprising one or more lumens configured to receive a bodily fluid from a patient body, a reservoir in fluid communication with the one or more lumens for receiving the bodily fluid, and a pumping mechanism to urge fluid through the one or more lumens. The pumping mechanism never fully obstructs outflow of said bodily fluid. In one alternative embodiment, the lumens have an interior diameter that maintains a siphon. The lumens may be less than ¼ inch in interior diameter. In some embodiments, the pumping mechanism cannot fully obstruct outflow even in the case of a system failure. In some embodiments, the pumping mechanism is peristaltic.

According to another aspect, embodiments of the present invention include a device for draining and measuring bodily fluids comprising multiple lumens, a pumping mechanism, and a volume or flow output measurement mechanism. In one alternative embodiment, the lumens have an interior diameter that maintains a siphon. The lumens may be less than ¼" inch in interior diameter. In some embodiments, the pumping mechanism urges fluid through the lumen without fully obstructing the lumen. In another alternative embodiment, the pumping mechanism is peristaltic. In some embodiments, the output measurement mechanism is pressure-based, resistance-based, capacitance-based, ultrasonically-based, or optically-based.

According to a third aspect, embodiments of the present invention include a device for draining and measuring bodily fluids comprising one or more lumens, a pumping mechanism in fluid communication with the one or more lumens, a volume or flow output measurement mechanism in fluid communication with the one or more lumens, and at least one additional analysis mechanism. The additional analysis mechanism is configured to detect one or more physiological parameters from the bodily fluids contained within the volume or flow output measurement mechanism and received through the one or more lumens. In some embodiments the lumens have an interior diameter that maintains a siphon. The lumens can be less than ¼" inch in interior diameter. In some embodiments, the pumping mechanism urges fluid through the lumen without fully obstructing the lumen. In some embodiments the pumping mechanism is peristaltic. In some embodiments, the output measurement mechanism is pressure-based, resistance-based, capacitance-based, ultrasonically-based, or optically-based. In some embodiments, the additional analysis mechanisms analyze at least one of specific gravity, oxygen tension, conductivity, gas pressures, and sediment.

According to a fourth aspect, embodiments of the present invention provide a method of automatically clearing one or more lumens used for draining bodily fluids, comprising passing bodily fluids from a patient through at least one drainage line, receiving the bodily fluids into a reservoir via the drainage line, and applying one of a pulsatile mechanical, vibratory acoustic, thermal, vibratory, pinching, rolling or electromagnetic stimulus to cause at least one of a movement of the drainage line and the bodily fluids within. In some embodiments, the rolling stimulus comprises compressing the lumens sequentially such that the lumens are never all compressed at the same time.

According to a fifth aspect, embodiments of the present invention provide a method of detecting and clearing a drainage line having one or more lumens used for draining bodily fluids, comprising draining bodily fluids from a bodily organ via a drainage line, detecting a pressure spike in the drainage line while a pressure within the bodily organ remains constant, and using massaging rollers to create negative pressure through the drainage line until the pressure in the drainage line equals the pressure in the bodily organ.

According to a sixth aspect, embodiments of the present invention provide a method for taking measurements of multiple urine parameters for detecting acute kidney injury, urinary tract infection, intra-abdominal hypertension, abdominal compartment syndrome, or sepsis. The urine parameters may include conductance, specific gravity, urine output, and oxygen tension.

According to a seventh aspect, embodiments of the present invention include a device for draining bodily fluids, comprising one or more lumens configured to receive a bodily fluid from a patient body, a reservoir in fluid communication with the one or more lumens for receiving the bodily fluid, a pumping mechanism to urge fluid through the one or more lumens, and a vent at the proximal (patient) end of the lumens to allow air to enter the line and thus prevent negative pressure from being applied to the patient. The pumping mechanism never fully obstructs outflow of said bodily fluid. In one alternative embodiment, the lumens have an interior diameter that maintains a siphon. The lumens may be less than ¼ inch in interior diameter. In some embodiments, the pumping mechanism cannot fully obstruct outflow even in the case of a system failure. In some embodiments, the pumping mechanism is peristaltic.

According to an eighth aspect, embodiments of the present invention include a device for draining and measuring bodily fluids comprising multiple lumens, a pumping mechanism, a vent at the proximal (patient) end of the lumens, and a volume or flow output measurement mechanism. In one alternative embodiment, the lumens have an interior diameter that maintains a siphon. The lumens may be less than ¼" inch in interior diameter. In some embodiments, the pumping mechanism urges fluid through the lumen without fully obstructing the lumen. In another alternative embodiment, the pumping mechanism is peristaltic. In some embodiments, the output measurement mechanism is pressure-based, resistance-based, capacitance-based, ultrasonically-based, or optically-based.

According to a ninth aspect, embodiments of the present invention include a device for draining and measuring bodily fluids comprising one or more lumens, a pumping mechanism in fluid communication with the one or more lumens, a vent at the proximal (patient) end of the lumens, a volume or flow output measurement mechanism in fluid communication with the one or more lumens, and at least one additional analysis mechanism. The additional analysis mechanism is configured to detect one or more physiological parameters from the bodily fluids contained within the volume or flow output measurement mechanism and received through the one or more lumens. In some embodiments the lumens have an interior diameter that maintains a siphon. The lumens can be less than ¼" inch in interior diameter. In some embodiments, the pumping mechanism urges fluid through the lumen without fully obstructing the lumen. In some embodiments the pumping mechanism is peristaltic. In some embodiments, the output measurement mechanism is pressure-based, resistance-based, capacitance-based, ultrasonically-based, or optically-based. In some embodiments, the additional analysis mechanisms analyze at least one of specific gravity, oxygen tension, conductivity, gas pressures, and sediment.

According to a tenth aspect, embodiments of the present invention include a device for draining bodily fluids, comprising one or more lumens configured to receive a bodily fluid from a patient body, a reservoir in fluid communication with the one or more lumens for receiving the bodily fluid, a pumping mechanism to urge fluid through the one or more lumens, and a valve at the proximal (patient) end of the lumens to maintain a specific level of negative pressure. The pumping mechanism never fully obstructs outflow of said bodily fluid. In one alternative embodiment, the lumens have an interior diameter that maintains a siphon. The lumens may be less than ¼ inch in interior diameter. In some embodiments, the pumping mechanism cannot fully obstruct outflow even in the case of a system failure. In some embodiments, the pumping mechanism is peristaltic. In other embodiments, the pumping mechanism is a diaphragm pump, impeller pump, or any other suitable pump. In yet other embodiments, the pumping mechanism is wall suction applied to the drainage reservoir.

According to an eleventh aspect, embodiments of the present invention include a device for draining bodily fluids, comprising one or more lumens configured to receive a bodily fluid from a patient body, a reservoir in fluid communication with the one or more lumens for receiving the bodily fluid, a pumping mechanism to urge fluid through the one or more lumens, a pressure sensor at the proximal (patient) end of the lumens, and closed-loop feedback control of suction to maintain a specific level of negative pressure. The pumping mechanism never fully obstructs outflow of said bodily fluid. In one alternative embodiment, the lumens have an interior diameter that maintains a siphon. The lumens may be less than ¼ inch in interior diameter. In other embodiments, the pressure sensor is located at the fluid reservoir. In some embodiments, the pumping mechanism cannot fully obstruct outflow even in the case of a system failure. In some embodiments, the pumping mechanism is peristaltic. In other embodiments, the pumping mechanism is a diaphragm pump, impeller pump, or any other suitable pump. In yet other embodiments, the pumping mechanism is wall suction applied to the drainage reservoir.

BRIEF DESCRIPTION OF THE DRAWINGS

The novel features of the invention are set forth. A better understanding of the features and advantages of the present invention will be obtained by reference to the following detailed description that sets forth illustrative embodiments, in which the principles of the invention are utilized, and the accompanying drawings of which:

FIG. 5 shows a urine receptacle that includes an RFID chip or circuitry, configured to collect and transmit data directly from within the receptacle to an RFID reader.

FIG. 10 shows another embodiment comprising multiple lumens organized circumferentially around a stiff member that the pinching or rolling mechanism rotates around.

FIG. 11 shows an alternative embodiment in which the lumens are organized such that they can only be completely compressed when pinched in a certain direction.

FIG. 13 is a table comparing intra-abdominal pressure (IAP) measurements using a standard drainage line and IAP sensor with the present invention in combination with a pressure-sensing Foley catheter under air lock and siphon effects.

FIGS. 19A-D illustrate the emptying sequence for the apparatus shown in FIG. 18.

FIG. 20 illustrates the use of the sample collection vessel and pressure tube to provide information about the volume and density (specific gravity) of the urine being collected.

FIG. 21 shows a table that lists combinations of parameters that allow for a fingerprint (unique combination of parameters) for the different causes of Acute Kidney Injury, or, AKI (pre-renal, intrinsic and obstructive).

FIG. 33 shows a small float that can be used in a pressure tube to completely drain when the siphon drains.

DETAILED DESCRIPTION OF THE INVENTION

The preferred embodiments of the present invention are described in detail herein. However, alternative embodiments of various features of the device are also possible. Examples of these embodiments are provided below, but the scope of the invention is not limited to these specific configurations.

The Urine Output Collection System

Figure 1:
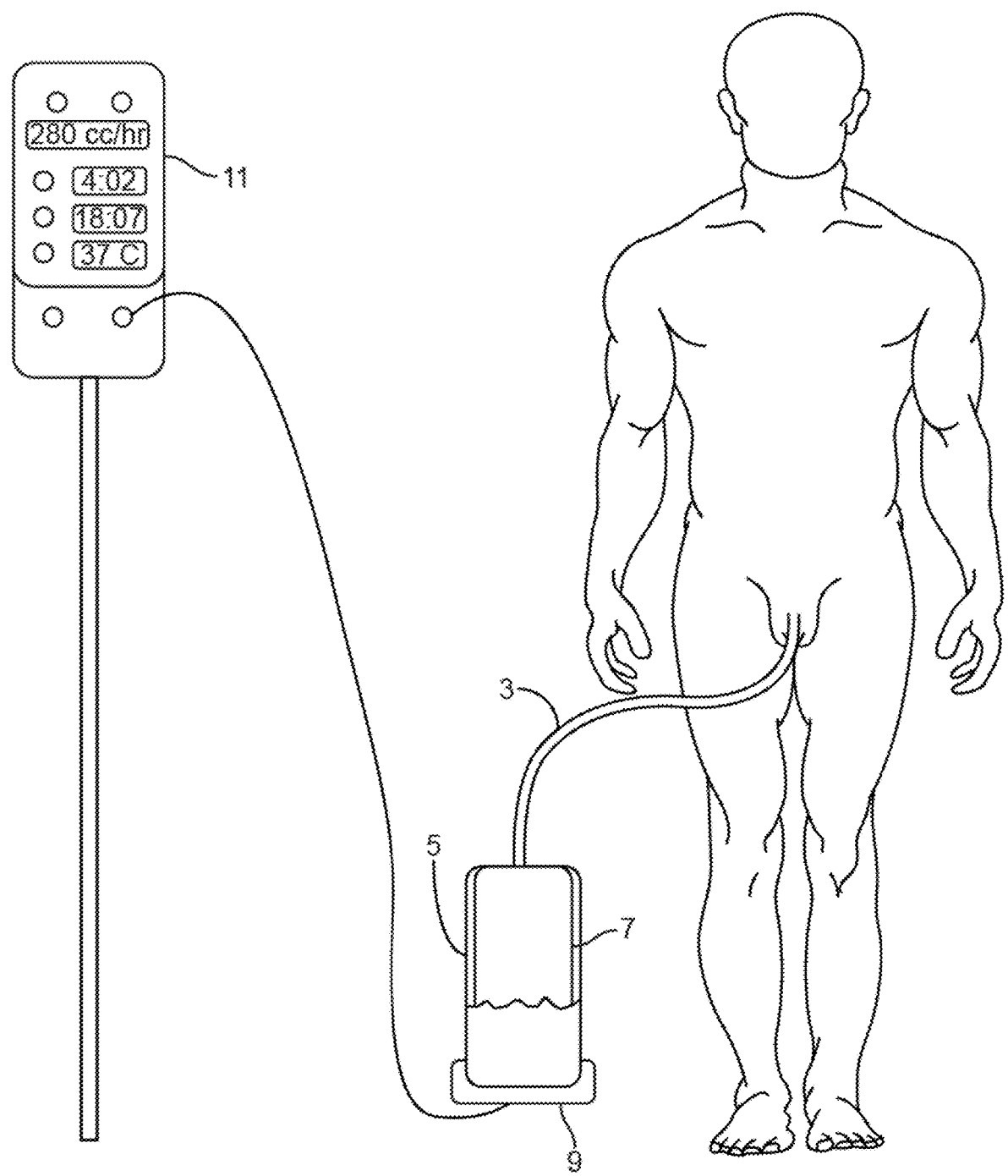
FIG. 1 shows an exemplary sensing Foley catheter urine output collection system (hereinafter, the sensing Foley catheter system) configured to measure urine output from a human subject.

FIG. 1 shows an exemplary sensing Foley catheter urine output collection system (hereinafter, the sensing Foley catheter system) configured to measure urine output from a human subject. The sensing Foley catheter system comprises urinary catheter 3 that empties into urinary receptacle 5 equipped with urine sensors 7. The urine sensors report the level of urine via any suitable modality, such as conductivity, resistance, and/or impedance. The urine sensors may also detect or measure levels of bacteria, hemoglobin, or other substances of clinical interest in urine. Receptacle docking station 9 may connect the urinary receptacle 5 and transmit data to a control unit either via wires or wirelessly. The receptacle docking station may also measure urine volume via weight or other methods. Receptacle docking station 9 is configured for data transmission to a data receiving and processing controller such as a bedside console or a central computer. In some embodiments, the docking station delivers data regarding the volume of urine in the urine receptacle, as well as data that are informative regarding electrical parameters of the urine, such as conductivity, resistance, or impedance. Console/controller 11, in communication with the receptacle docking station 9, can trigger an alert if the urine output is too low or too high over a set period of time.

Figure 2:
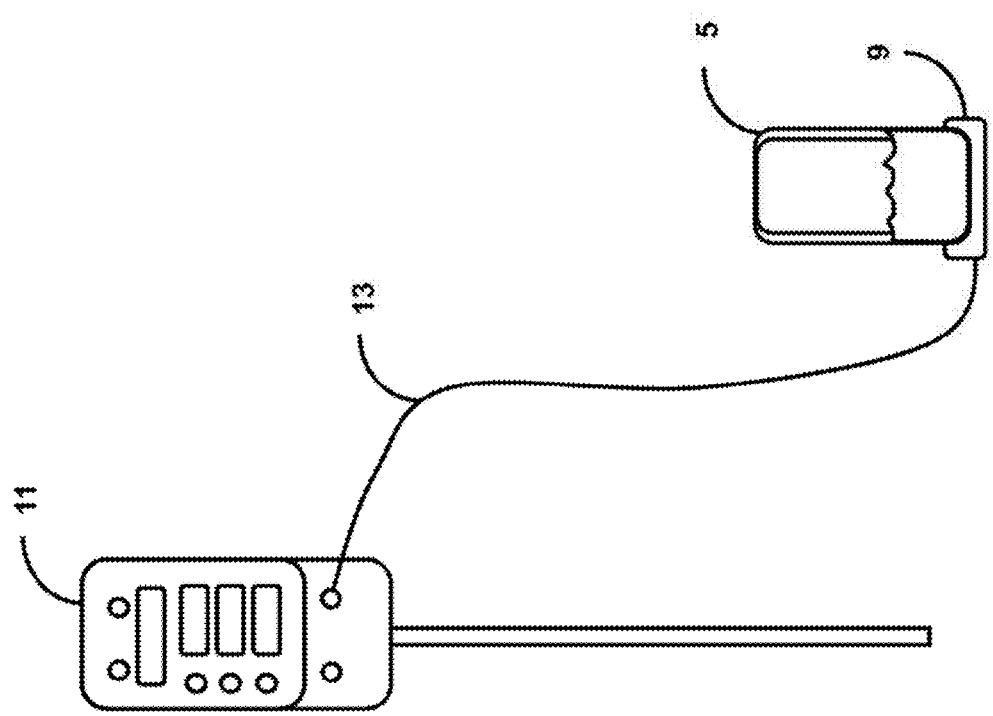
FIG. 2 shows an embodiment of the sensing Foley catheter urine system comprising a console in communication with the receptacle docking station that accommodates a urine collection receptacle.

FIG. 2 shows an embodiment of the sensing Foley catheter urine system comprising console/controller 11 in communication with receptacle docking station 9 that accommodates urine collection receptacle 5. The communication path between the docking station and the console may include a wired connection 13, as shown, or it may be a wireless connection. The console may record and display output/input data. The data from sensors associated with the sensing Foley catheter may be held in a memory, displayed, printed, or directly transmitted to a centralized data collection server.

In some embodiments, the bedside console or controller is portable and able to travel with the patient. Embodiments of the console may be attachable to a patient's bed or an IV pole, or a wall mount. The console/controller may have its own display, and may be able to provide critical alerts. Some embodiment of console may be adapted to be able to operate on a battery backup for 4 or more hours, as for example when wall power is unavailable or has been lost. This portability feature of console is advantageous in situations where patients are usually not monitored, such as when a patient is in transit from his or her bed to another location. Embodiments of the console may also be configured to communicate to a base station with alerts and centralized reporting and data collection. The controller or base station may also generate mobile alerts that may be sent to nurses or healthcare providers. Signal analysis and/or predictive algorithms may also be used to provide useful clinical data from sensors.

Figure 3:
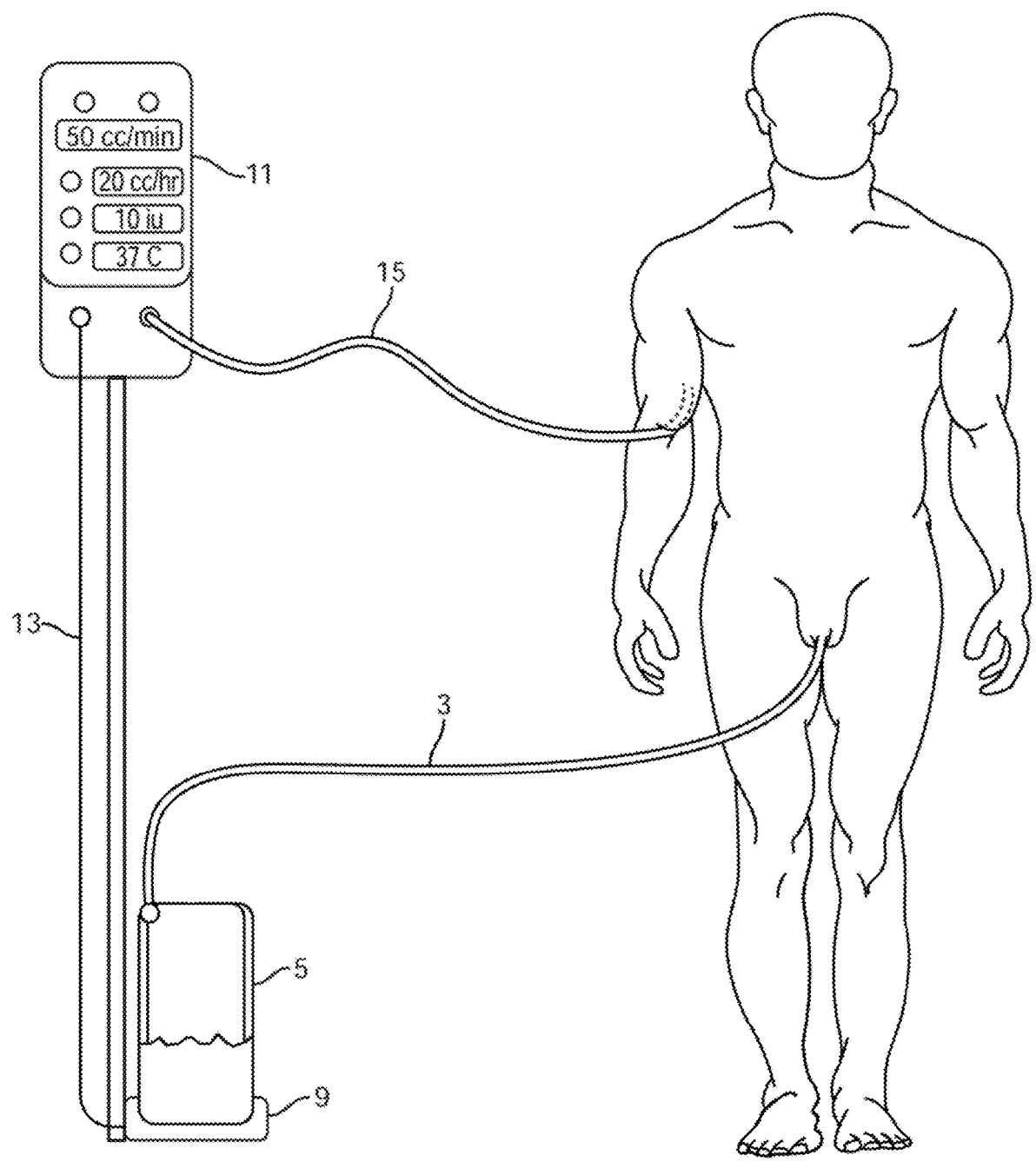
FIG. 3 shows an embodiment of the sensing Foley catheter system configured as an automated infusion therapy system for a human subject.

FIG. 3 shows an embodiment of the sensing Foley catheter system configured as an automated infusion therapy system for a human subject. In this embodiment console 11 may integrate patient data, such as data relating to fluids received or urine output recorded, and then automate therapeutic infusion via infusion catheter 15 in response to these data. For example, delivery of fluids or drug solutions such as a physiological saline solution may be initiated or regulated if the patient is dehydrated, or a diuretic may be infused if the patient is fluid overloaded. In some embodiments, the console may trigger a local alert (e.g., audible beeping), or trigger a centralized alert (e.g., a system alarm) if urine output drops too low. This embodiment may be particularly beneficial to burn patients. The console may also integrate a hydrating or medicinal fluid infusion capability, such as an IV infusion pump (not shown), and may adjust infusion rates based on these data or based on data acquired from other sensors automatically. Console 11 may communicate wirelessly, as well, to these, and other sensors within the body.

The Urine Receptacle and Receptacle Docking Station

Figure 4:
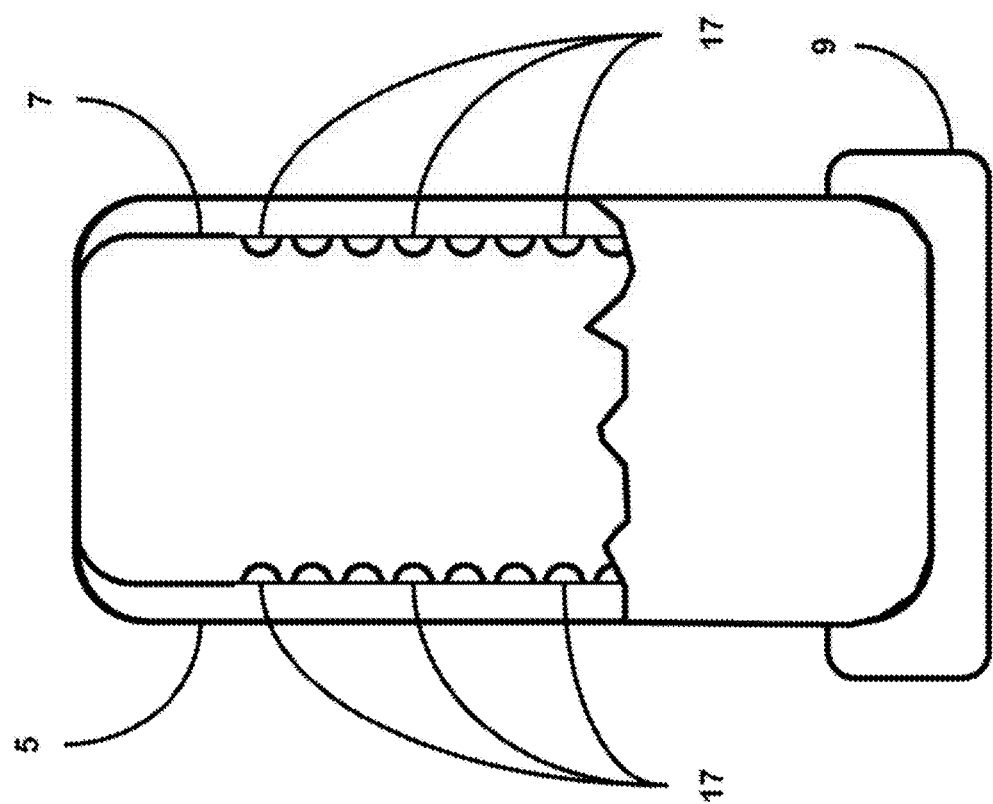
FIG. 4 shows a urine receptacle configured to sense urine volume, accommodated within a receptacle docking station, per an embodiment of the sensing Foley catheter system.

FIG. 4 shows urine receptacle 5 configured to sense urine volume, accommodated within a receptacle docking station, per an embodiment of the sensing Foley catheter system. The receptacle may detect urine output based upon level at which sensors 7 are triggered. For example, sensors 7 may comprise electrical contacts 17 arranged as hash-marks, and when an electrical path is made between two contacts and all contacts below, the level can be reported at that level. Urine receptacle 5 may include electrical, optical, chemical, acoustic, or mechanical sensors. Embodiments of urine receptacle 5 may also include diffuse or discrete sensing areas that detect analytes of interest, e.g., hemoglobin, protein, glucose, bacteria, blood, leukocyte esterase. Sensing or data reporting of sensed data may be of either an intermittent or a continuous nature.

Urine receptacle 5 may include a capability to report sensing data to the bedside console, locally (e.g., by beeping) or centrally via piping data to a central information collection area. For example, an alert may be triggered if urine output drops below 30 cc/hr. in post-operative setting or below any otherwise predetermined threshold. Urine receptacle 5 may connect to a receptacle docking station 9 through electrical contacts; data communication among embodiments of the receptacle, docking station, and a console or central computer may also be wireless. If a receptacle docking station 9 is used, it may detect urine output based on weight or pressure of urine receptacle 5 that is applied to base.

Urine receptacle 5 may include disposable or durable optical, electrical or chemical sensors capable of sensing and measuring urine content of analytes such as glucose, electrolytes, bacteria, hemoglobin, or blood. Urine receptacle 5 may include an interface with a specifically designed area of the urine receptacle to allow for this measurement, such as an optically clear window for optical measurement of blood. Receptacle docking station 9 may also grasp the urine receptacle in any manner to secure the receptacle. The docking station or the receptacle may include an inductive antenna or RFID capabilities to allow for wireless querying and reporting of the level of urine or other fluid collection.

FIG. 5 shows urine receptacle 5 that includes RFID chip or circuitry 19, configured to collect and transmit data directly from within the receptacle to a RFID reader. When queried by RFID reader 21, urine receptacle 5 may detect impedance, resistance, capacitance or any other electrical or non-electrical property to measure the urine level and report this back to the reader. RFID reader 21 may then trigger an alert if urine output is out of a normal or desirable range. RFID chip or circuitry 19 may be capable of detecting changes in optical, chemical, electrical acoustic or mechanical properties, as well. RFID chips or circuitry 19 may be active or passive, and may contain an antenna to transmit a receptacle-identifying signal to the reader, and allow multiple receptacles to be queried simultaneously. RFID chip or circuitry 19 may incorporate a small battery (to extend its range) in an active RFID embodiment, or it may be a passive chip powered by the transmission from the RFID reader. RFID reader 21 may query a device from a distance to wirelessly check the urine output level or it may be centralized to query all receptacles within a unit, floor or hospital and issue an alert if urine output is out of a normal or desirable range. RFID reader 21 may record urine output, as well, and functionally replace individual unit console/controller 11 shown in FIGS. 1-3. RFID reader 21 may also report data from other sensors within the system, including bladder temperature or presence of analytes (as detailed elsewhere herein) in the urine.

Airlocks and Embodiments of the Device with Line Clearing

Some embodiments of the device may incorporate mechanisms to keep the drainage line clear of blockages in order to maintain an empty, flaccid bladder and avoid false positive LAP measurements. These blockages may be caused by airlocks in the drainage tube or by crystals, blood clots, or other physical blockages. Any of the embodiments to keep the line clear as described in Burnett PCT Patent Application PCT/US13/60003 would be suitable. In one embodiment, this is accomplished with active line clearing, such as a bellows to provide negative pressure or a pump to clear obstructions. This embodiment allows for clearing of both airlocks and physical blockages. In another embodiment, the line clearing is passive, and may be accomplished with vents that allow air to escape the drainage line instead of forming airlocks. In yet another embodiment, the IAP measurements from the present device may be combined with urine output measurements obtained with the Burnett device, in any manner they have disclosed.

Automated Drainage Line-Clearing Device

Figure 6:
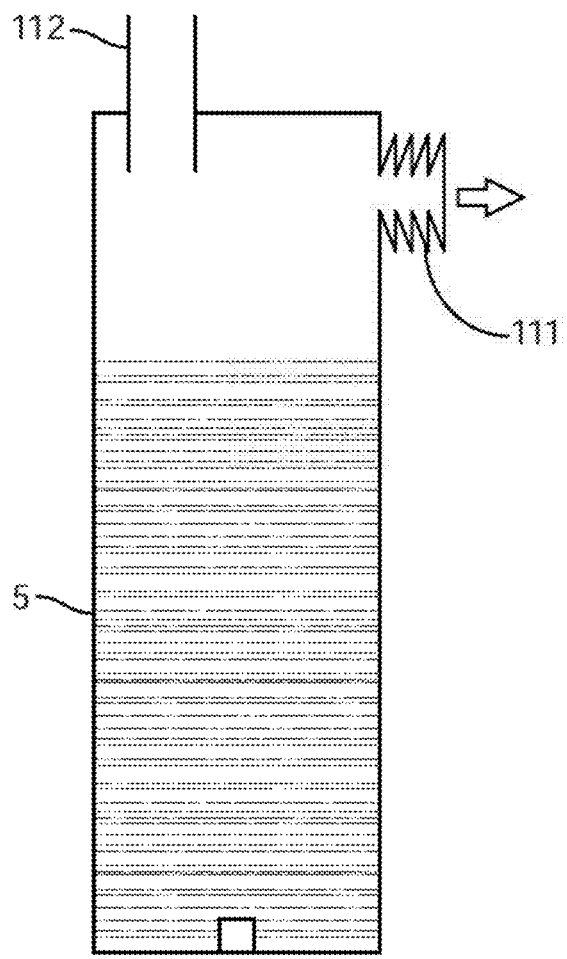
FIG. 6 shows an embodiment for clearing the drainage line that uses a vacuum applied to the end of the drainage line.

One embodiment of the sensing Foley catheter system also includes an automated drainage line-clearing device. The drainage line is the tube that connects the Foley catheter to the drainage bag. FIG. 6 shows an embodiment for clearing the drainage line that uses a vacuum applied to the end of the drainage line. The vacuum, transmitted through drainage line 112 and, the Foley catheter to the bladder of the patient, facilitates more effective draining than a drainage line without vacuum. In one aspect, the vacuum is created by bellows 111 attached to urine collection device or receptacle 5. Bellows 111 is expanded in its natural state, but is compressed before the urine catheter is inserted into the patient. Once the catheter is in place, bellows 111 is released, and the restoring force creates a negative pressure in the urine collection device. In another embodiment, the restoring force may also be created by a spring within bellows 11. In another aspect, the vacuum is created by a pump. The pump may be any suitable pump, including but not limited to diaphragm pumps, peristaltic pumps, or vane pumps. The pump may be powered by a wall outlet, battery, human power, or any other suitable source. In another aspect, the vacuum preferably is in the range of 0 to −50 mmHg.

Figure 7B:
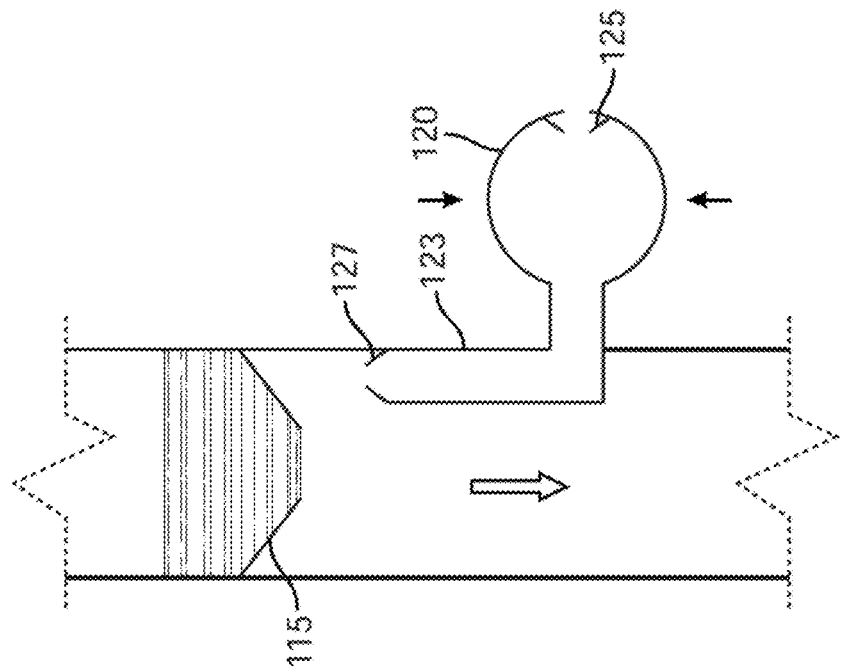
FIGS. 7A-7B, show an embodiment of the clearing mechanism comprising a device for positive airflow near the start of the drainage line.
Figure 7A:
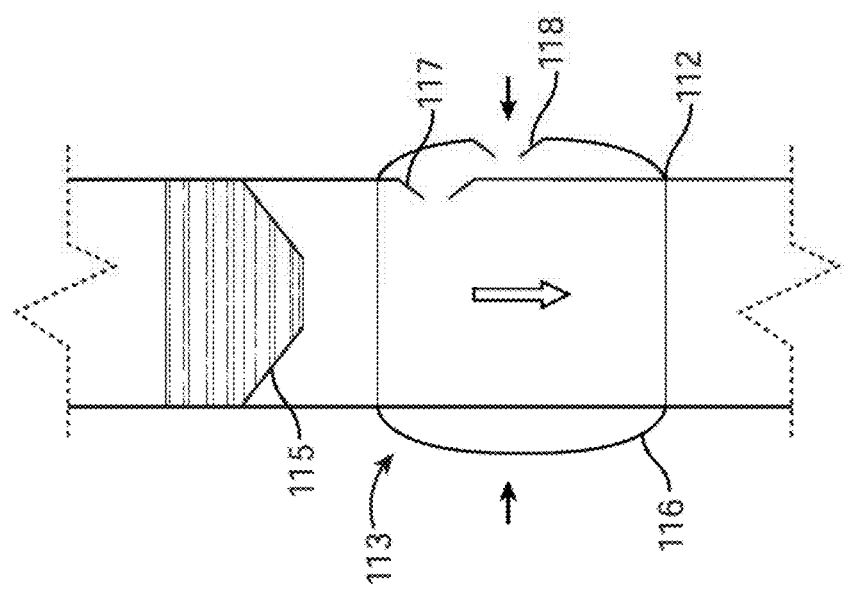

FIGS. 7A-7B, show an embodiment of the clearing mechanism comprising a device for positive airflow 113 near the start (or patient side) of drainage 112. Said positive airflow facilitates drainage by forcing urine to flow through the drainage line. In one aspect, shown in FIG. 7A, the positive airflow device comprises one-way valve 115 at the end of the urine catheter that allows urine to only flow toward the urine collection device, and prevents air from entering the catheter. In another aspect the positive airflow device comprises diaphragm 116 attached to the start of the drainage line. Said positive airflow device also comprises one-way valve 117 that allows air to enter the drainage line but prevents air or urine from exiting and one-way valve 118 that allows air to enter the diaphragm but prevents air from exiting. Therefore, as diaphragm 116 is compressed, it forces air to flow through drainage line 112. When compression is relieved, diaphragm 116 expands into its natural state and new air is introduced through one-way valve 118. One-way valves 117 and 118 could be any suitable valves, including but not limited to umbrella valves and duckbill valves. In another aspect, shown in FIG. 7B, diaphragm 120 is connected to the start of drainage line 112 through lumen or tube 123 that runs from the patient end of the drainage line to diaphragm 120. Diaphragm 120 also comprises one-way valve 127 that allows air to enter the drainage line but prevents air or urine from exiting, and one-way valve 125 that allows air to enter the diaphragm but prevents air from exiting. In yet another aspect (not shown), the positive airflow device comprises a pump. The pump may be any suitable pump, including but not limited to a diaphragm pump, peristaltic pump, or vane pump. The pump may be powered by a wall outlet, battery, human power, or any other suitable source. In yet another aspect, the positive airflow device comprises a syringe attached to the drainage tube. The syringe may attach to the drainage tube with a luer lock, septum valve, or any other suitable interface.

In another embodiment, the clearing mechanism comprises a coating on the inside of the drainage tube to reduce surface tension and facilitate drainage. In one aspect, said coating is a hydrophobic polymer, including but not limited to PTFE or FEP.

Figure 8:
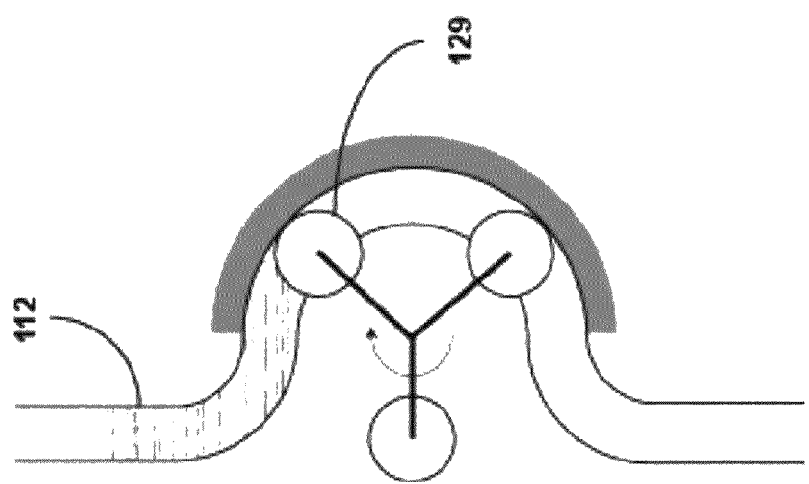
FIG. 8 shows a clearing mechanism comprising an apparatus for automated massaging, or squeezing, of the drainage line.

In another embodiment, shown in FIG. 8, the clearing mechanism comprises an apparatus for automated massaging, or squeezing, of drainage line 112. In one aspect, the squeezing apparatus comprises a peristaltic pump 129. Peristaltic pump 129 also provides slight vacuum to the bladder, which helps to facilitate drainage as described herein. In another aspect, the squeezing mechanism comprises a slider-crank mechanism attached to a rotary motor. In another aspect, the squeezing mechanism comprises a solenoid. In another aspect, the clearing mechanism further comprises one-way valves on either side of the squeezing mechanism to force urine and air to only flow down the tube and further provide vacuum to the bladder.

In another embodiment, air locks are removed through use of a pulsatile mechanical, vibratory acoustic, thermal, or electromagnetic stimulus that results in movement of the drainage tubing and/or the fluid within. This vibration, in combination with the pressure gradient driving the urine preferentially from the patient to the urine drainage bag, allows the urine to move forward in small increments until the resistance of the air lock has been overcome. At this point, a siphon is created and normal drainage can resume. The pulsatile stimulus is effective due to the hysteresis involved in the flow of the urine in the presence of a pressure gradient. Small movements of the urine due to energy pulses will have a net effect of moving the urine away from the patient. In one aspect using pulsatile energy, a vibratory stimulus is employed. The vibratory stimulus described can be created using a coin vibration motor, eccentric motor, or other similar means.

As an alternative to the vibratory stimulus, the drainage tube may be pinched or rolled intermittently, which has a similar net effect of moving the urine away from the patient due to hysteresis. This pinching or rolling may be achieved using a peristaltic-like mechanism, slider-crank mechanism, or other similar means. An alternative approach would be to use a pneumatic or hydraulic pump to cycle compression and decompression, like a sphygomomanometer, on different sections of the tube to mimic manual milking of the tube. This approach is distinct from the automated massaging or squeezing described above, in that only a slight pulse of stimulus is required. The pulsatile approach, then, can avoid generating vacuum in the bladder, which may adversely affect bladder tissue. The vibratory or pinching stimulus may be placed near the patient, near the drainage tube, or anywhere in between.

In another aspect using pulsatile energy, an acoustic stimulus is employed. The acoustic stimulus may be of a subsonic frequency designed to agitate the fluid but not the patient (due to the stimulus being below the range of hearing). The stimulus may also be in the sonic range or even in the supersonic range to achieve higher energy delivery. In the acoustic embodiment, the pressure waves will be transmitted down the fluid column generating the same hysteresis effect.

In another aspect using pulsatile energy, an electromagnetic stimulus is employed. The electromagnetic stimulus may be a cuff or other device external to the drainage tube that creates pulses of electromagnetic energy. This energy has an effect on the salts in the urine, effectively agitating it slightly toward the drainage bag. The principles underlying this method are that of an electromagnetic pump, which is used in other applications. The electromagnetic approach takes advantage of the same hysteresis effect as the other approaches, and has the same effect of removing air locks by agitating the urine toward the drainage bag until a siphon effect is achieved.

In another aspect using pulsatile energy, a thermal stimulus is employed. The thermal stimulus may be used to rapidly heat and cool a small portion of the drainage tubing, thereby expanding and contracting the urine or air within. In the expansion phase, the leading edge of the urine or air preferentially expands toward the drainage bag, due to the pressure gradient. Similarly, in the contraction phase, the tailing edge of the urine or air moves toward the drainage bag. The thermal stimulus thus takes advantage of the same hysteresis effect as the other approaches. Rapid heating of the urine or air can be achieved with a heating coil, chemical reaction, or other similar means, while rapid cooling of the urine or air can be achieved with a Peltier cooler, chemical reaction, gas expansion, or other similar means.

In another embodiment the mechanical, acoustic, electromagnetic, thermal, vibratory or pinching stimulus may be continuous, scheduled, or sensor-based. In the continuous embodiment, the stimulus is always on. In the scheduled embodiment, the stimulus repeats itself after a given time period, such as, but not limited to, every 1 minute, 5 minutes. 10 minutes, 30 minutes, or 1 hour. In the sensor-based embodiment, the mechanical, acoustic, electromagnetic, thermal, vibratory or pinching stimulus is applied whenever an air lock is suspected or detected based on urine output and sensed pressures. This detection can be accomplished in a variety of ways, including, but not limited to, a flow sensor, an optical sensor that distinguishes between urine and air, or an in-line oxygen sensor. Furthermore, each of these embodiments could be expected to interfere with pressure measurements in the sample collection vessel described below and will preferably be performed immediately after a siphon activation to allow for minimization of the risk of missing a vessel emptying or interfering with a specific gravity measurement.

Figure 9:
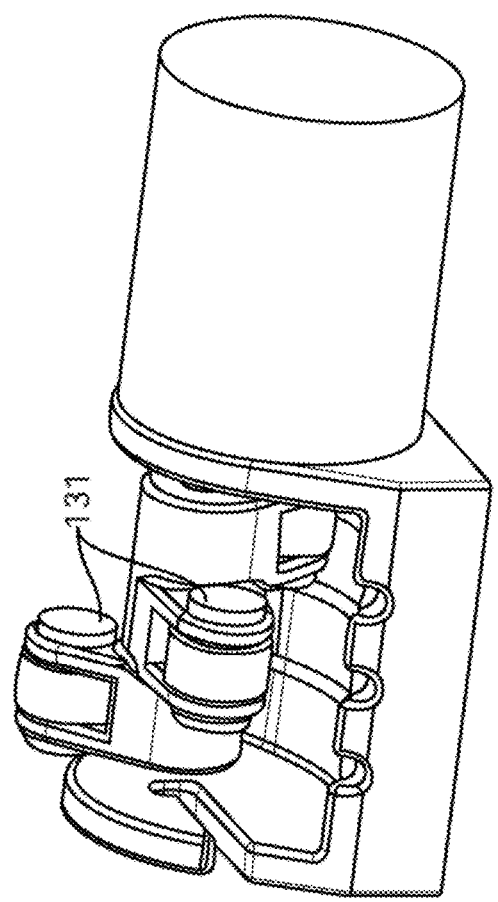
FIG. 9 shows another embodiment of the pinching or rolling stimulus, in which the lumens are compressed sequentially by rollers.

FIG. 9 shows another embodiment of a pinching or rolling stimulus, the lumens are compressed sequentially by rollers 131 such that they are never all compressed at the same time. This feature serves to prevent all lumens from becoming obstructed, a scenario that could cause urine to back up in the patient's bladder and lead to detrimental conditions. Having multiple lumens that are only compressed one at a time also helps reduce the amount of negative pressure that is applied to the bladder wall. This prevents trauma to the soft tissues. In one aspect, the lumens lay side-by-side in a strip fashion, and the pinching or rolling mechanisms are offset such that they can only compress one lumen at a time.

Preferably, an entire drain tube will be cleared with one roll; at a minimum, one half of a drain tube height may be cleared, given a maximum air lock height. Advantageously, these rollers can handle high viscosity urine. The rollers comprise cam profiles that may be round or oval-which can provide varying pressure for clearing clots. Should a blood clot obstruction occur at a Foley catheter inlet hole, the rollers can be used to temporarily reverse the flow of urine to dislodge the clot, or (as previously described) intentional vibration of the fluid column can be used to dislodge the clot. The roller position can be selectively controlled so as to avoid "parking" on tubes. This ensures that flow is completely unobstructed from the bladder to the drainage bag. Controlling the parked location can be accomplished with any suitable means, including, but not limited to a stepper motor, current sensing of the motor (current will drop when the rollers are not compressing the tubes), a limit switch, an encoder, magnetic positioning, detection of a change in tube diameter as it is compressed, and/or pressure sensors on the lumen or roller. However, in certain instances, parking the rollers on the tubing may be beneficial for selectively limiting the flow if it is too high for the chamber to handle, particularly when first intubating the bladder. In these instances, selective control of the roller position will be used to ensure one of the tubes is compressed.

The rollers can be activated manually, using a timed means, or automatically triggered if, based on the number or urine drips in a chamber, no urine output is detected for a specified member of minutes. Suction trauma to the soft tissues is prevented by setting the roller speed so that it occurs slowly enough to remain quasi-static. In the event of an air lock with an empty bladder, for example, in one embodiment the roller would pull gentle suction on one tube, but the suction transmitted to the bladder would be limited by the ability of fluid to move from one tube to the other by virtue of their being joined at the proximal end of the tube where it connects to the Foley catheter.

FIG. 10 shows another embodiment comprising multiple lumens 145 organized circumferentially around stiff member 141 that the pinching or rolling mechanism 143 rotates around, thereby compressing one lumen at a time and avoiding complete obstruction of all lumens. FIG. 11 shows an alternative embodiment in which the lumens 145 are organized such that they can only be completely compressed when pinched in a certain direction 147, or 148. A plurality of rolling or pinching mechanisms are used to compress the tube sequentially from multiple directions, and each mechanism can only compress those lumens that are designed to be compressed in that direction. FIG. 11 illustrates an example of lumen geometries that are only fully compressed in a preferential direction. In the non-preferential direction, the lumens cannot be completely compressed. In this example, lumens 147 will be compressed with the illustrated pinching force, while lumens 148 will not. Alternatively, a single rolling or pinching mechanism rotates around the tube to compress it sequentially from multiple directions. In another embodiment of the sequential pinching or rolling stimulus, the portion of the tube that is pinched or rolled is only a small portion of the entire drainage tube, such that the geometry of the rest of the drainage tube is not limited to the geometries required to facilitate sequential compression of the lumens. In another embodiment of the peristaltic pumps used for massaging, squeezing, or pulsing, the pump is a finger-style peristaltic pump that uses linear motion to stimulate the drainage tubing.

In another embodiment, a pressure sensing lumen may be incorporated into the tubing to allow for measurement of pressure within the drain tube, Foley catheter or bladder itself. This pressure measurement can be used to control the pump or line clearing mechanism to allow for effective air lock removal without the generation of negative pressure and suction trauma in the bladder. This device may also be used in combination with a pressure sensing Foley catheter as described in US Pat. App. No. US20130066166, Ser. No. 13/414,307. This combination will allow for the effective measurement of true bladder pressure and activation of the pump to ensure that the sensed bladder pressure is truly a result of intra-abdominal hypertension and not the result of a confounding air lock. The sensing balloon of the Foley can also be incorporated proximally into the Foley catheter or be attached to the drainage tube in order to minimize the intravesical profile of the device. The sensing lumen could also be another lumen in the tube that conducts the pressure through the lumen to the pressure sensor and roller pump. In the absence of an air lock, the pressure seen in fluid communication with the inside of the bladder is actually a vacuum. In order to provide an accurate measurement of bladder pressure in the setting of a siphon effect (i.e. with a vented Foley drain system or in the absence of any air lock) the pumping mechanism can actually be driven backwards until it has offset the siphon effect. There will still be no net movement of fluid in this scenario and the pump action will be increased until further increases do not generate an increase in sensed pressure. At this point the true bladder pressure can be read and the flow from the bladder can be allowed to resume.

Figure 12:
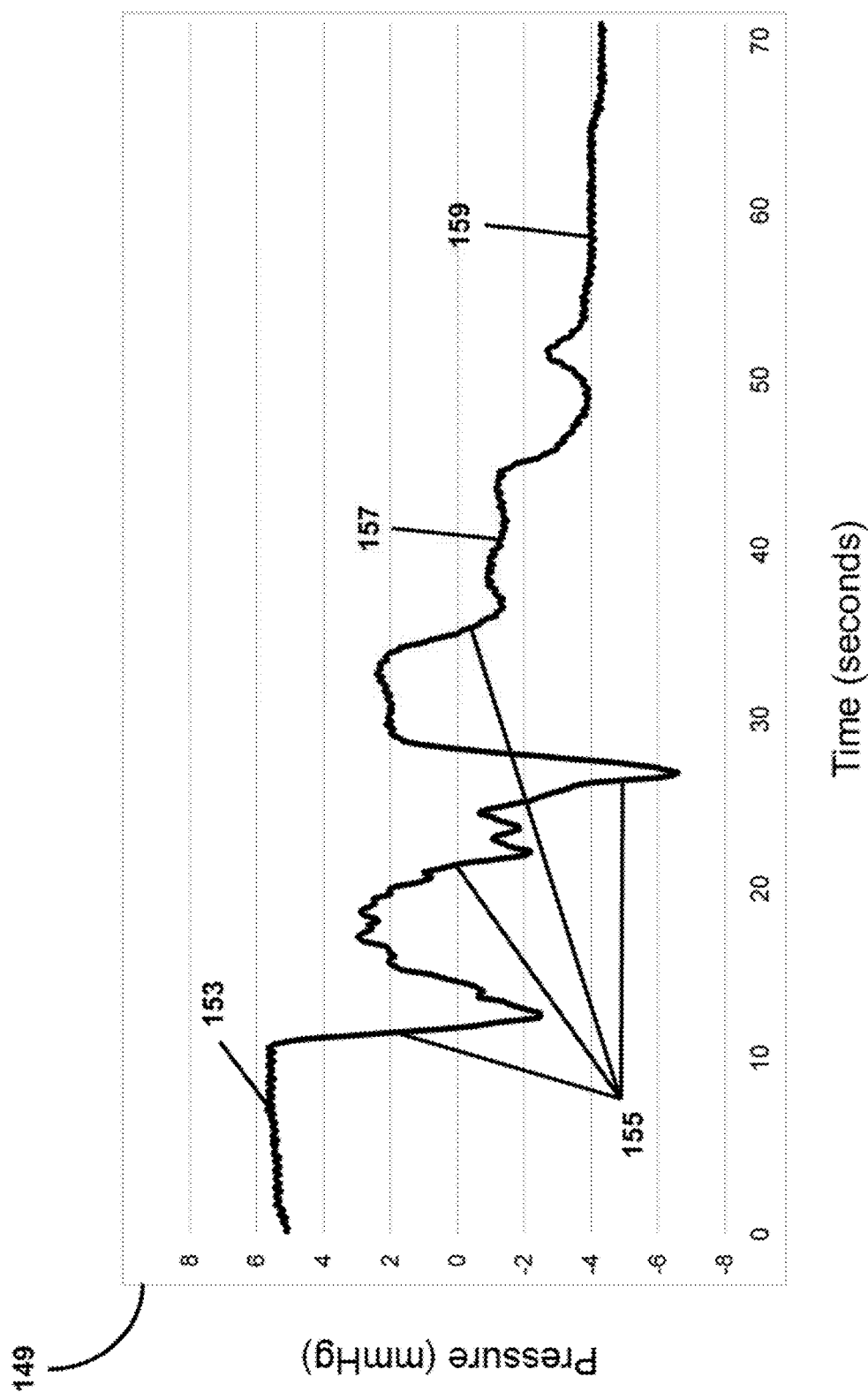
FIG. 12 shows a graph of the pressure profile, pressure (mmHg) over time (seconds) in the drain tube while the peristaltic roller pump is activated.

FIG. 12 shows a graph of the pressure profile, pressure (mmHg) 149 over time (seconds) in the drain tube while the peristaltic roller pump is activated. The graph shows an airlock being formed and pressure building 153, vacuum 155 generated in drainage tube, Foley catheter by peristaltic action of pump and detected by pressure sensor, elimination of airlock with the pump parked on one tube 157, and airlock eliminated with the pump parked on none of the tubes 159. No matter how the vacuum is generated (peristaltic pump, integrated gear pump, etc.) the bladder is at risk of suction trauma. This suction trauma can cause mucosal irritation and bleeding and can increase the risk of bladder infection. Monitoring the pressure and activating/deactivating pump operation based on the sensed pressure mitigates this risk and allows for effective line clearance without exposing the bladder to excessive vacuum. In addition, in the event that a siphon effect is generated, purposefully occluding one of the outflow tubes can decrease the overall vacuum generated within the bladder. Temporarily reversing the action of the pump can offset the siphon and provide a true bladder pressure.

FIG. 13 is a table comparing LAP measurements using a standard drainage line and IAP sensor with the present invention in combination with a pressure-sensing Foley catheter under air lock 161 and siphon 163 effects. A sheep bladder was used to compare pressure measurements between standard drainage technologies and the present invention (shown here as Accuryn). In the presence of an air lock, traditional technologies to measure IAP report false positive values, whereas the Accuryn device shows greater accuracy. In the absence of an air lock, but in the presence of a siphon (due to a full drainage tube), the traditional technology reports accurate values if used intermittently, with a valve in place to temporarily block flow from the bladder to the drainage tube. The present device also reports accurate values in the presence of a siphon. However, when used continuously without a valve, the traditional technology severely underreports the true pressure. Without air lock prevention and elimination, IAP cannot be accurately and reliably measured. In addition, respiratory rate, tidal volume, heart rate, cardiac output and stroke volume readings from the bladder may be diminished and/or corrupted due to the floating baseline of pressure within the bladder.

In yet another embodiment (not shown), the present invention and the pressure-sensing Foley catheter can be used together to detect and clear obstructions from blood clots or other obstructions. During milking of the drainage tube, if the pressure in the drainage tube spikes while the pressure within the bladder remains unchanged, this is indicative of a blockage between the bladder and the termination of the pressure sensing lumen. To clear this blockage, additional negative pressure can be generated using the massaging rollers until the pressure suddenly drops and matches the pressure within the bladder. This is indicative that the blockage has been cleared. In yet another embodiment, blockages such as those from blood clots can be prevented by ensuring that the inner diameter of the drainage lumen/tube only gets larger or remains the same size from the bladder to the drainage bag. When the opposite occurs, this creates the potential for bottlenecks that can become a site for obstruction.

In addition, any and all of the aforementioned inventions may be utilized in other drainage tubes including tubes draining liquid (urinary, pleural cardiac, bile, wound, peritoneal dialysate, drain tubes, etc.) or tubes pulling air (i.e. pneumothorax evacuation, etc.). Chest tubes, in particular, have been noted to be susceptible to air locks and pressure accumulation within the chest wall which can subsequently lead to poor outcomes. These tubes would greatly benefit from an air lock prevention/removal feature, particularly if this feature were controlled by pressure measurement near the chest wall to control the degree of vacuum/suction generated by the pump.

In another aspect of the present invention, an automated urine output measurement device is provided, comprising one or more methods for detection of passing urine and a number of its parameters.

Figure 14A:
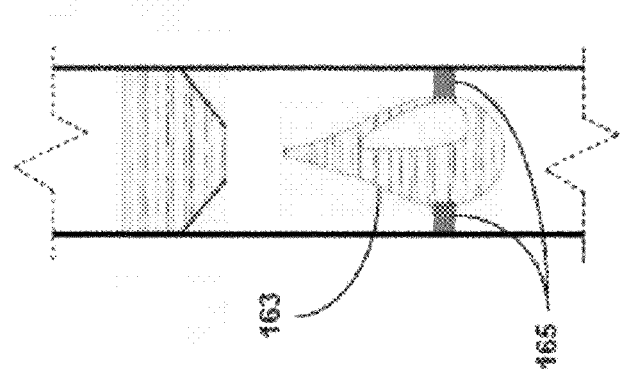
FIGS. 14A-D illustrate resistive or conductive methods for detecting urine, urine is detected by a change in resistance or conductance between two or more electrical leads.

FIGS. 14A-D illustrate resistive or conductive methods for detecting urine; urine is detected by a change in resistance or conductance between two or more electrical leads. In FIG. 14A, the urine is controlled to create drips 163, which pass between two or more leads 165 and change the resistance or conductance between the leads 165. When the change in resistance or conductance is detected, a drip 163 is counted and the calibrated volume of drop 163 is added to the total urine output volume. In order to create uniform drips for drip counting, urine should be allowed to run along a tube for drip counting. In cases where the viscosity of the urine is changing dramatically, the size of each drip may be affected, which could interfere with the conversion of drips to volume. However, this issue can be overcome by using real time drip calibration, where the volume of drips is calculated based on volume at conductivity leads. With each triggering of the conductivity leads, the known volume at that level is divided by the number of drips since the last emptying to calculate the volume of each drip. Alternatively, the change in the pressure signal may be used to account for changes in viscosity that lead to varying drip size; more viscous drips will be larger and therefore have a larger "splash" pressure wave. If accounting for viscosity by means of varying drip size, this information may also be displayed as another parameter in the urinalysis, including real-time and trending data. Because viscosity and specific gravity of urine are closely related, this parameter may also be used in place of true specific gravity measurements.

Figure 14B:
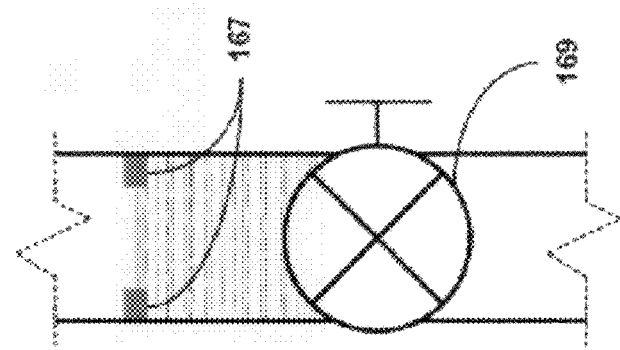
Figure 14C:
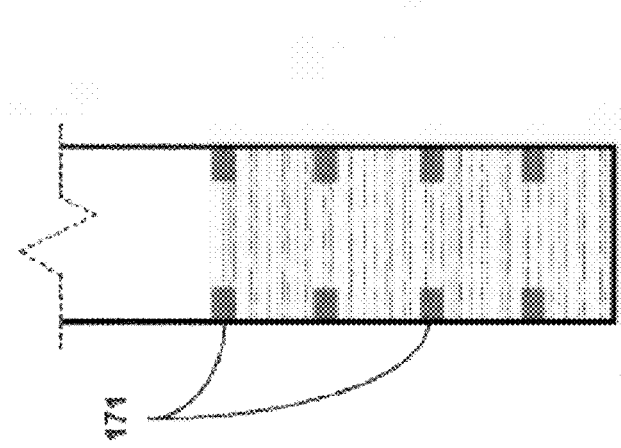
Figure 14D:
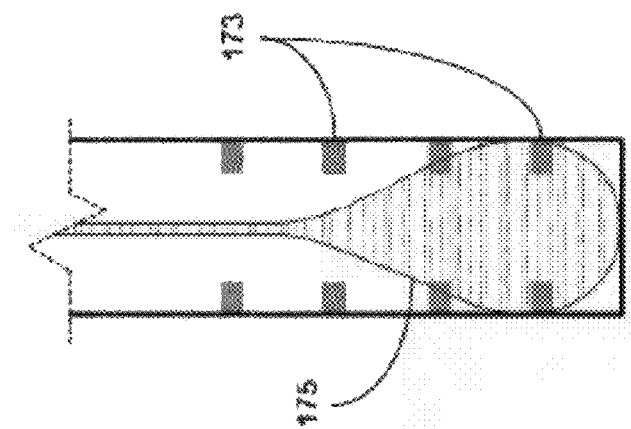

FIG. 14B shows the collection device with embedded electrical leads 167 on the inside which make contact with the urine only when it has risen to a certain level, at which point the collection device is emptied by opening valve 169, tilting, or some other similar method, and the calibrated volume is added to the total urine output volume. In another aspect, shown in FIG. 14C, the collection device has embedded electrical leads 171 on the inside that run the height of said collection device, and are always in contact with the urine. The total urine output volume is determined by the resistance or conductance measured between said leads 171, which changes as the volume of urine increases. In yet another aspect for any of the resistive or conductive embodiments described herein, shown in FIG. 14D, the leads 173 do not make physical contact with the urine, but instead the urine fills a balloon or bladder 175 within the urine collection device, which expands and makes contact with the leads. The balloon or bladder 175 can be made of any suitable elastomeric material, including but not limited to silicone, polyurethane, or nylon. In another aspect, the resistance or conductance of the urine is used as an indicator of the density, or specific gravity, of the urine, which is another indicator of the fluid status and renal function of the patient.

In other embodiments, shown in FIGS. 14A-D, the method for detecting urine is capacitive, in which urine is detected by a change in the capacitance between two or more electrical plates or leads. The electrical plates or leads can take any of the same forms as described for the resistive detection methods herein, including as a drip counter, can be in direct contact with the urine or through a balloon or bladder, and can use capacitance as an indicator of specific gravity.

In other embodiments, shown in FIGS. 14A-D, the method for detecting urine is thermal, in which urine is detected by a change in the temperature of one or more probes. The probes can take any of the same forms as described for the resistive detection methods herein, including as a drip counter, and can be in direct contact with the urine or through a balloon or bladder. The probes can comprise any suitable temperature transducer, including but not limited to thermistors or thermocouples.

In other embodiments, shown in FIGS. 14A-D, the method for detecting urine is optical, in which urine is detected by one or more optical sensors, including but not limited to infrared emitter-detector pairs or cameras. The optical sensors can take any of the same forms as described for the resistive detection methods herein, including as a drip counter, and can use urine clarity as an indicator of specific gravity. The optical sensors may detect changes in opacity in the urine. They may also look at the color spectrum to detect red, which could signal blood, or white, which could signal pus. The optical sensors may also detect bacteria, cells and urinary casts, which are small particles made up of white blood cells, red blood cells, or kidney cells. The overall opacity of the urine may also be indicative of certain diseases, i.e. rhabdomyolysis, internal hemorrhage, etc. In one preferred embodiment, bacterial contamination can be estimated based on photospectrometric analysis of the sample at certain wavelengths. In the preferred embodiment, the urine sample may be exposed to an emitter of 260 nm and 280 nm wavelength light with one or more receivers positioned to receive the light after it has passed through the sample. The ratio of absorptions at 260 nm vs 280 nm can then be used to estimate the quantity of DNA and RNA versus protein in the sample. In the preferred embodiment, as well, visible light and light in the red spectrum can also be used to determine the overall turbidity of a solution and the presence (or absence) of blood in the sample. For example, light with wavelength of around 500 nm has good sensitivity to overall turbidity and may provide a good marker of bacterial overgrowth (in the absence of absorption of red wavelength, which would indicate the presence of blood). An increase in the DNA in the sample that has stable transmission of visible and red wavelengths could indicate an increasing bacterial load. Increasing absorption of red wavelength in the sample, on the other hand, may indicate blood and also throw an alarm.

In another embodiment, the method for detecting urine is microfluidic, in which the urine passes through a microfluidic flow detection chip and is integrated to determine total urine output volume. In another aspect, the microfluidic chip measures volume instead of flow, and adds a discrete volume of urine to total urine output volume each time said discreet volume passes through the chip.

Figure 15:
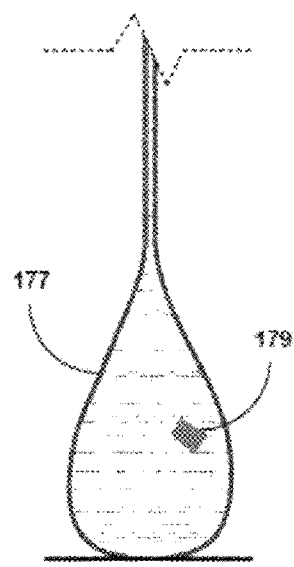
FIG. 15 illustrates a method for detecting urine that is strain-based.

FIG. 15 illustrates a method for detecting urine that is strain-based, in which an increase in urine volume stretches balloon or bladder 177 and is detected by one or more suitable strain transducer 179, including but not limited to electrical foil gages or fiber Bragg grating optical sensors. In one aspect, balloon or bladder 177 contains the entire urine output volume, which is measured continuously. In another aspect balloon or bladder 177 fills to a certain volume, indicated by the strain transducer 179, and is emptied into a larger storage container. With each emptying, the calibrated volume is added to the total urine output volume. Balloon or bladder 177 can be made of any suitable elastomeric material, including but not limited to silicone, polyurethane, or nylon. In another aspect, balloon or bladder is made of an electroactive polymer that compresses when voltage is applied.

Figure 16A:
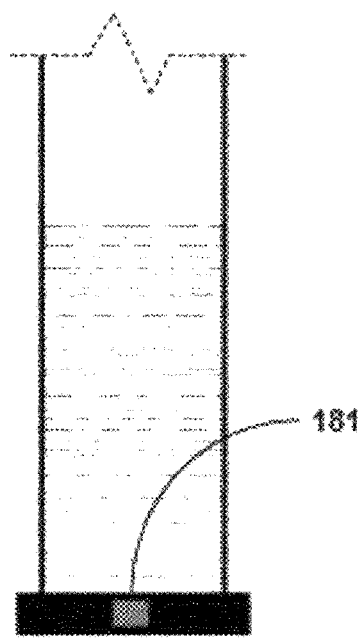
FIGS. 16A-C show methods for detecting urine that are weight- or pressure-based, in which an increase in urine volume increases the weight of the collection device and the pressure of the urine column.
Figure 16B:
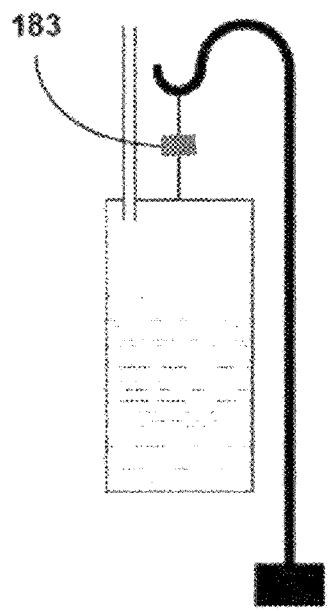
Figure 16C:
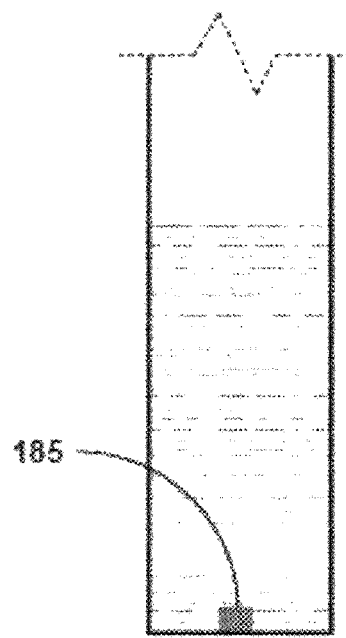

FIGS. 16A-C show methods for detecting urine that are weight, or pressure, based in which an increase in urine volume increases the weight of the collection device and the pressure of the urine column. In one aspect, shown in FIG. 16A, the urine collection device is placed on top of force measuring device 181, such as but not limited to a scale. In another aspect, shown in FIG. 16B, the urine collection device is hung from force measurement device 183. In another aspect, said collection device fills to a certain volume, indicated by measurement device 183, and is emptied into a larger storage container. With each emptying, the calibrated volume is added to the total urine output volume. In another embodiment, shown in FIG. 16C, the method for detecting urine is pressure-based, in which an increase in urine volume is detected by one or more pressure transducers 185, including but not limited to piezoelectric or potentiometric sensors. Transducers 185 provide an indication of the height of the urine, which is converted to volume by multiplying by the known cross-sectional area of the urine collection device.

Figure 17:
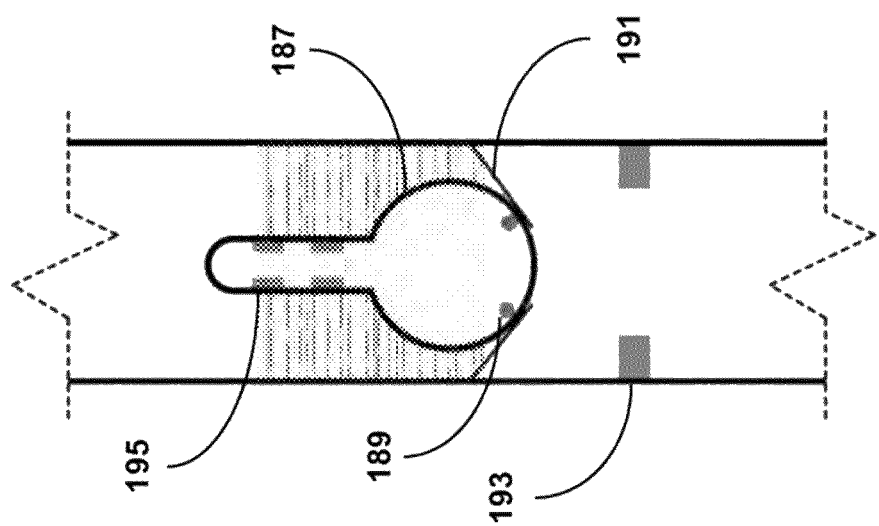
FIG. 17 illustrates a method for detecting urine makes use of a magnetic float valve, which is initially held closed with a magnet.

FIG. 17 illustrates a method for detecting urine makes use of magnetic float valve 187, which is initially held closed with magnets 189. As urine fills the measurement container, float 187 becomes submerged under the urine and the buoyant force increases until it eventually overcomes the magnetic force, breaking free and opening valve 191. The urine is then allowed to pass through valve 191 as float 187 descends, eventually reengaging with magnetic force and closing valve 191. Cycles of the valve opening and closing are counted by any suitable means, including but not limited to optical sensors or resistive sensors 193, as described herein. In another aspect, float 187 has detectors on its surface, including but not limited to electrical leads 195, which detect the degree to which the float is submerged. The degree to which float 187 becomes submerged before breaking free from the magnetic force is dependent on the density, or specific gravity, of the urine, which is another indicator of the fluid status and renal function of the patient.

In another embodiment, the method for detecting urine makes use of an impeller, fan, water wheel, or any other suitable device that rotates in the presence of flowing fluid, in which passing urine causes rotations that are detected by means such as but not limited to magnetic or optical encoders. With each rotation, a calibrated volume of urine is added to the total urine output volume.

In another embodiment, the conductance of the urine is measured. This measurement can be accomplished with any of the methods previously described, including using conductive wires or strips to measure the conductance of the urine between them. The wires, strips, or other potential embodiments may also be used to measure urine output volume, as described above, or may be standalone devices used exclusively for the measurement of urine conductance.

In another embodiment, the specific gravity of the urine is measured. This measurement can be accomplished with any of the methods previously described, including using resistance/conductance, capacitance, urine clarity (with optical sensors), or a float/hydrometer. These parameters may also be used to measure urine output volume as described above, or may be standalone devices used exclusively for the measurement of specific gravity. In yet another embodiment, specific gravity is obtained by measuring the pressure just prior to the voiding of the disposable sample collection vessel at a known column height of urine. Density of the urine is thus calculated p=P and converted to specific gravity by dividing by the density of water. This method allows for calculation of specific gravity using the pressure sensor already being used to measure urine output volume. Additional embodiments for measuring specific gravity include, but are not limited to, using refraction measurements, vibration measurements, or any other known methods for measuring specific gravity.

In another embodiment, the oxygen tension of the urine is measured. In one aspect of the embodiment, this measurement is made using an electrochemical sensor such as, but not limited to, Clark type electrodes that make use of a silver/silver chloride anode and platinum cathode to reduce available oxygen or those that make use of phosphorescence quenching.

In another embodiment, prevention of contamination from ambient air on measurements of oxygen tension is accomplished by filling the sample collection vessel with nitrogen gas before use and connecting it to the distal end of the urinary catheter in such a manner that very little to no ambient air is introduced into the vessel. This can be accomplished with the use of a valve, septum or other similar feature. As an alternative to filling the sample collection vessel with nitrogen, it may be evacuated of air prior to use through use of vacuum packaging or other appropriate means. Yet another alternative embodiment may be to include an oxygen absorber in the vessel. Said oxygen absorber can be made from any appropriate material that reacts with available oxygen, including, but not limited to, iron oxide or ascorbic acid. This oxygen-absorbing material may be in the form of loose granules or pellets, in packages, or in rolls or strips. Furthermore, said collection vessel and drainage tubing may be made from a substantially oxygen impermeable material, such as but not limited to glass, metals such as stainless steel, or plastics such as vinyl, polyurethane, PMMA or other oxygen impermeable polymers. This prevents atmospheric oxygen from contaminating the urine samples prior to analysis.

In yet another embodiment, the effects of changing conductivity on measurements of oxygen tension are corrected for using the conductivity measurements already being made. This embodiment is preferred, as changing conductivity levels will affect the readings of oxygen tension using the electrochemical sensors described herein. Therefore, prior to use, the present invention will be calibrated such that the relationship between conductivity, measured oxygen tension, and actual oxygen tension is known and accounted for.

Figure 18:
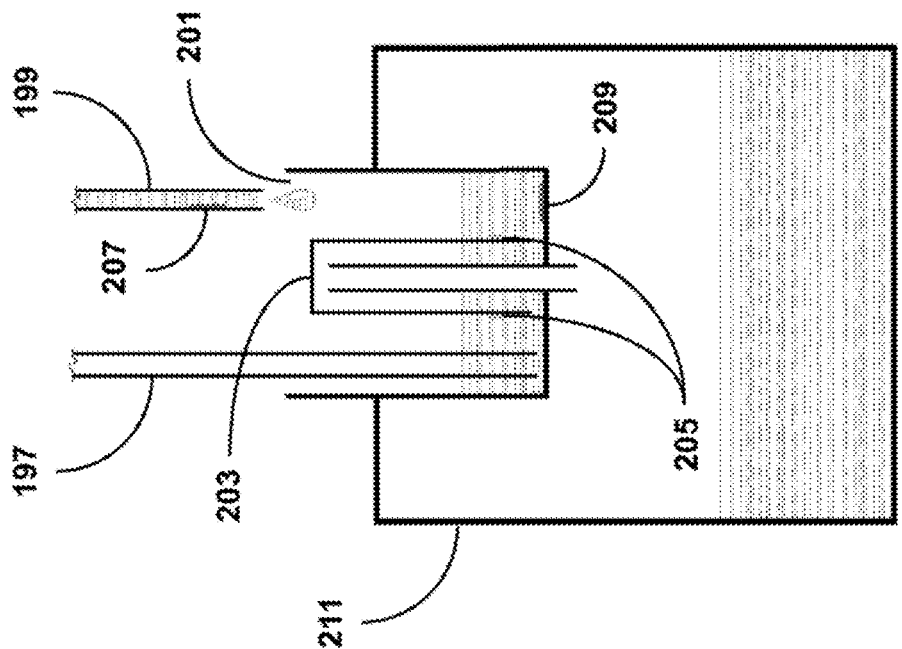
FIG. 18 shows a small sample collection vessel self-emptying by means of a siphon that is triggered when the urine volume reaches a pre-determined level.

In an alternative embodiment, the oxygen and conductance measurements are made within the drainage tube or urinary catheter itself. Measurements are made in-line in order to prevent mixing with previous urine or atmospheric gases or particles. Said measurements are accomplished by placing the oxygen sensor and conductance leads within the drainage tube or urinary catheter. FIG. 18 shows small sample collection vessel 201 self-emptying by means of a siphon that is triggered when the urine volume reaches a pre-determined level. Urine enters sample collection vessel 201 through drainage tubing 199. As urine enters the sample collection vessel, it may pass oxygen sensor 207. Once in the sample collection vessel, the urine level is measured by means of pressure tube 197 that converts pressure to height, based on the urine density, and height to volume, based on the cross sectional area of the sample collection vessel. While the urine is filling the sample collection vessel, additional measurements of conductance, specific gravity, oxygen tension, or carbon dioxide, nitric oxides, nitrogen, and any other gas pressures may be made by means of sensors 205 and 209. As the urine level rises in the sample collection vessel, it also rises in the self-emptying siphon 203, which eventually drains the urine into the larger collection vessel 211.

FIGS. 19A-D illustrate the emptying sequence for the apparatus shown in FIG. 18. In FIG. 19A, the urine is filling the sample collection vessel, which is partially full. In FIG. 19B, the urine has reached the level just before the siphon will be triggered. In FIG. 19C, the siphon has been activated and the urine is draining from the sample collection vessel into the larger collection vessel. Finally, in FIG. 19D the sample collection vessel has emptied completely and the filling process starts over.

Pressure changes in the collection vessel can signal key events, such as overflow and backflow, in urine monitoring. For example, when the pressure in the sample collection vessel rises and then remains high with drips, then urine is overflowing. If the pressure continues to rise with no drips, then the urine is backing up; since this is a failure mode, a clinician should be alerted. Backflow can be prevented by having the user empty the bladder and clamping the disposable tubing and drainage portion before removing them. Alternatively or in addition, the direction of flow of the urine should be marked on the drain tube so that the user can see if it is back-flowing. Alternatively, an air vent at the top of the drainage tube can open when the disposable tubing is removed. Opening this air vent eliminates the siphon effect within the drainage tube, which then to allows the urine to empty into the drainage bag.

The sample collection vessel or chamber needs to be protected from bacteria and encrustation. By raising the temperature of the chamber between the drain tube and collection bag to temperatures higher than 30 degrees Celsius, encrustation can be prevented. Bacteria, such as *Escherichia coli. Candida* spp, *Enterococcus* spp, *Pseudomonas aeruginosa. Klebsiella pneumoniae, Enterobacter* spp, other gram-negative bacteria, *Staphylococcus* spp, *Proteus mirabilis. Enterococcus faecalis* and *Staphylococcus aureus* may also be killed by either high or low temperatures, for example temperatures above 50 degrees Celsius for over 30 minutes. As an alternative, the chamber may be irradiated with UV. A stand-alone clamp-on device may be used for the chamber, as well as the other drainage tubes and Foley catheters. Removal of oxygen from the chamber will kill aerobic bacteria present. The presence of silicone, or other oil-liquid, capsule or as coating—and silver in the chamber will prevent bacterial growth.

FIG. 20 illustrates the use of the sample collection vessel and pressure tube to provide information about the volume and density (specific gravity) of the urine being collected. Each filling of the collection vessel is indicated by a rise in pressure, and each emptying is indicated by a sudden decrease in pressure. Because the vessel empties once it reaches a pre-determined volume, these emptyings can be counted to calculate the volume of urine that has passed. Additionally, the specific gravity can be calculated with each emptying of the vessel, as the density of the urine will determine the pressure at each emptying. In another embodiment, the known volume could be further detected by appropriate placement of the conduction sensing electrodes near the fill line for siphon activation. Once the fluid level reaches these electrodes, the pressure is detected and converted into a specific gravity.

Taking measurements of multiple urine parameters as described, such as conductance, specific gravity, urine output and oxygen tension, provides a synergistic source of information that is more informative than each of these measurements taken alone. This is because a change in any individual parameter could be the result of any number of possible conditions. For a given combination of changing parameters, however, the list of possible conditions that may have caused the change is much smaller. For example, increasing specific gravity in the presence of stable conductance is indicative of urinary deposition of non-conductive solutes, while increasing specific gravity in the presence of decreasing conductance, decreasing oxygen tension, and decreasing urine output is indicative of ischemia (or pre-renal) acute kidney injury (AKI).

FIG. 21 shows a table that lists combinations of parameters that allow for a fingerprint (unique combination of parameters) for the different causes of AKI (pre-renal, intrinsic and obstructive). In addition, there may be a unique fingerprint with respect to the timing of changes of the parameters, which may also determine the causes of AKI (e.g. it is plausible that some parameters change faster for intrinsic AKI caused by glomerulonephritis versus intrinsic AKI caused by acute tubular necrosis). This multi-parametric approach may also facilitate the choice of effective therapies to treat AKI since different causes of AKI have different effective therapies (e.g. recombinant alkaline phosphatase is effective at treating intrinsic (septic) AKI but ineffective at treating non-septic AKI).

In addition to detecting AKI, the present invention is capable of detecting urinary tract infections (UTIs), as indicated by decreasing oxygen tension, carbon dioxide levels, increasing specific gravity, and relatively stable urine output and conductance. The detection of UTI can be achieved in the absence of AKI, and possibly in the presence of AKI, by combining urinary markers for a unique fingerprint of UTI. The unique UTI fingerprint can alert clinicians to the presence of UTI.

In addition to detecting AKI and UTI using the described parameters, these parameters may be used in combination with intra-abdominal pressure (IAP), respiratory rate (RR), heart rate (HR), cardiac output (CO) and/or stroke volume (SV) readings, which are already used for detecting conditions such as intra-abdominal hypertension (IAH), abdominal compartment syndrome (ACS) and sepsis. This combination of parameters may be accomplished by using the present invention in conjunction with a pressure-sensing Foley catheter, such as one described by Burnett WO2012/122267A and also described in an Application for Federal Assistance (SF 424 (R&R) titled A novel device for improving sepsis outcomes through hemodynamic optimization (Tracking Number: GRANT11282036, Funding Opportunity Number:PA-12-088)). Adding IAP, RR, HR, CO and/or SV measurements to the algorithm described herein may increase the sensitivity and specificity of detecting AKI or UTI. On the other hand, adding the measurements obtained by the present invention to an LAP, RR, HR, CO and/or SV measurement algorithm may increase the sensitivity and specificity of detecting IAH. ACS or sepsis. Other clinical applications include the treatment of trauma and burns.

The present invention can be used in a variety of hospital settings (e.g. emergency room, operating room, intensive care unit, ward). At any time, the device may be used to monitor the progression of AKI, and whether it is improving or declining. Its algorithms work to alert clinicians to a newly developed case of AKI or to a change in the status of AKI. The device may be placed before insult to the kidney occurs (e.g. patients undergoing cardiac surgery to detect if insult to the kidneys begins intra-operatively) in order to detect initiation of AKI. It may be placed when insult to the kidney injury is already present in order to detect the degree of insult at that time. The device may also be used to monitor the response the therapy/therapeutic intervention (e.g. renal replacement therapy, fluid resuscitation).

Figure 22:
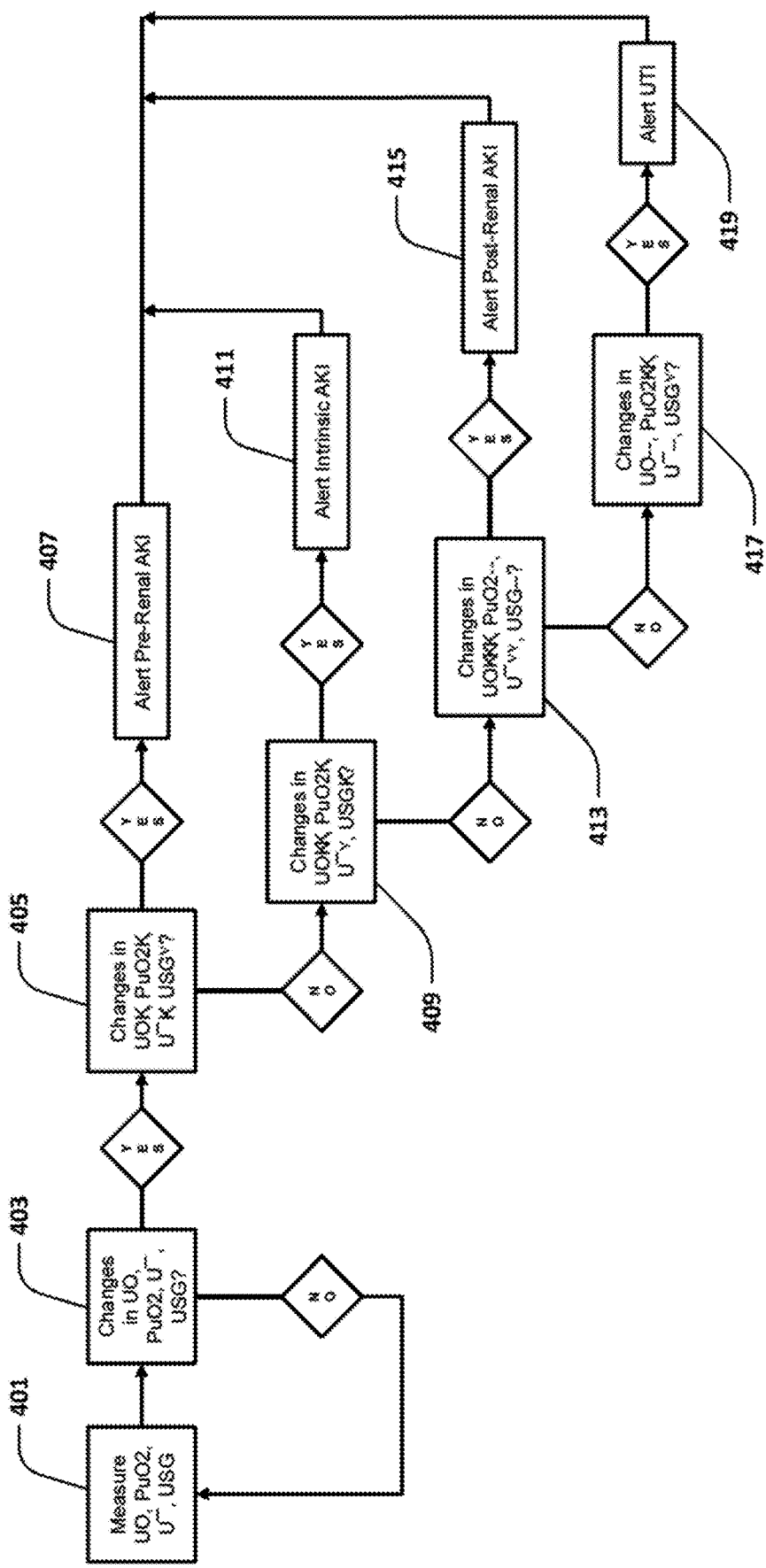
FIG. 22 illustrates the Urine Collection and Detection System (UCDS) algorithm.

FIG. 22 illustrates the Urine Collection and Detection System (UCDS) algorithm. First, urine output, oxygen pressure, conductivity, and specific gravity are measured 401. If there are no changes in these parameters 403, nothing happens and the device continues to take measurements. If urine output, oxygen pressure, and conductivity is decreasing and specific gravity is increasing 405, an alert is thrown for pre-renal AKI 407. If oxygen pressure and specific gravity are decreasing, urine output is rapidly decreasing, and conductivity is increasing 409, an alert is thrown for intrinsic AKI 411. If urine output is decreasing rapidly, conductivity is increasing rapidly, and oxygen pressure and specific gravity are steady 413, an alert is thrown for post-renal AKI 415. If oxygen pressure is decreasing rapidly, specific gravity is increasing, and urine output and conductivity are steady 417, an alert is thrown for UTI 419.

The current invention may utilize a small volume urine sample collection vessel (preferably 5-10 cc in volume) that dumps into the larger collection vessel and performs urinalysis on a mixed fluid of urine production over a given time interval. The current invention has also demonstrated feasibility in that even at pathologically low flow rates, the urine being analyzed consists of a mixture of a fraction of an hour's worth of urine collection. Additionally, the device is able to accommodate any catheter flow rate (i.e., an uneven flow rate) and any flow rate in to or out of the sample collection vessel. Regarding conductance, the present invention measures overall conductance as opposed to concentrations of specific analytes, which are relatively difficult and expensive to perform. Finally, the proposed device does not require the use of calibration fluids, which are expensive and cumbersome to use.

Figure 23:
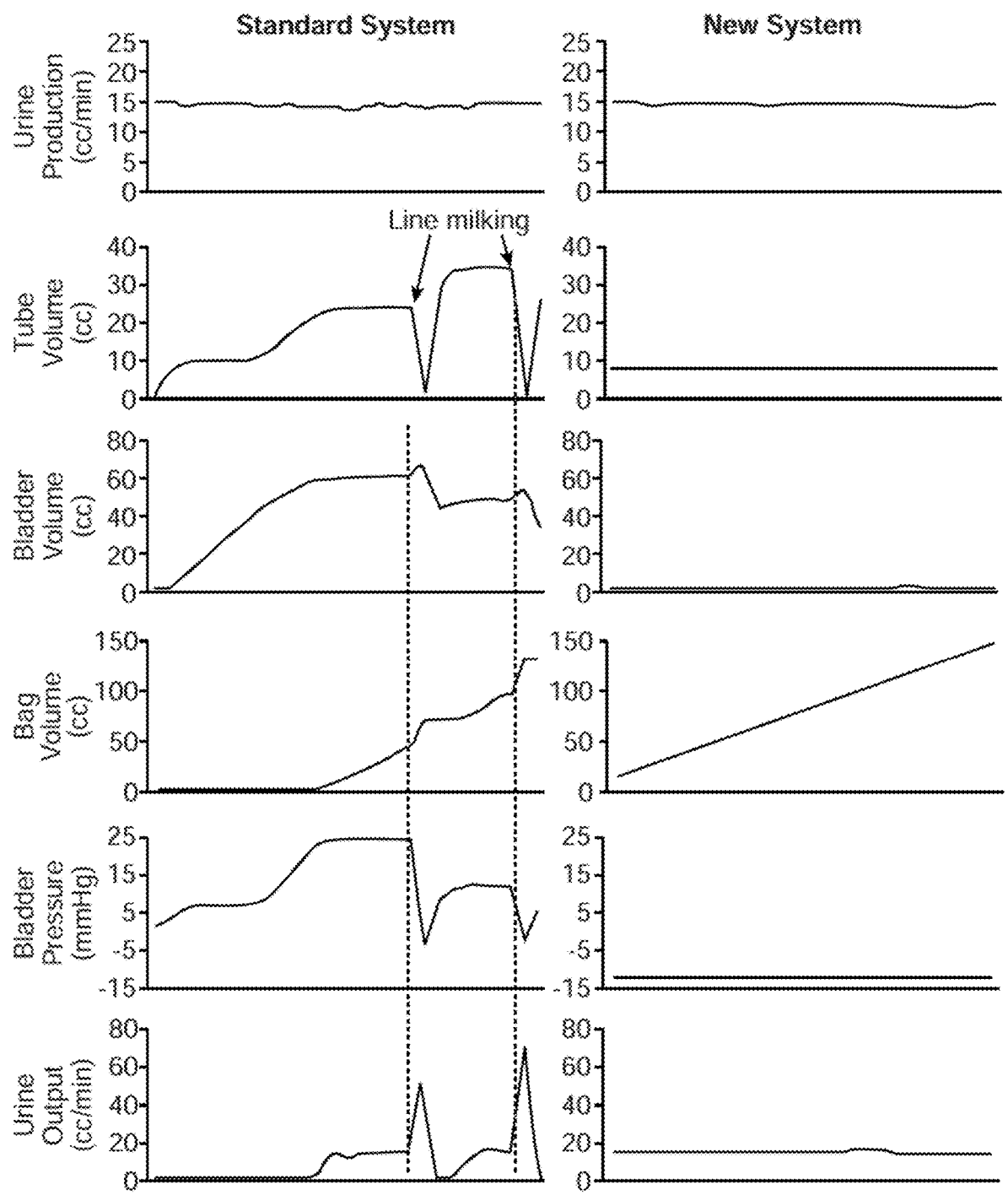
FIG. 23 shows a comparison between an embodiment of the present invention with a Standard System over a variety of parameters during constant urine production on a bench top model.

By combining air lock prevention/clearing with precision urine output measurements, highly accurate urine output measurements can be obtained using the present invention. FIG. 23 shows a comparison between the invention (New System) and a Standard System over a variety of parameters during constant urine production on a bench top model. Urine production is kept steady at 15 cc/min, as shown in the first graph for both systems. In the standard system, the first component to fill with urine is the tube, which fills to a certain amount, becomes air locked, and plateaus. During this plateau, urine begins to collect inside the bladder. Urine then continues to collect in the bladder and the drainage tube such that the pressure inside the bladder equals the pressure due to the air lock. Only when the bladder pressure is high enough to produce an airlock tall enough for the urine to reach the top of the drainage tube does drainage into the bag begin. At this point, urine output measurement using the standard system is accurate. However, once the line is milked (emptied), the cycle repeats itself. As a result, the urine output measurements using a standard drainage system are normally incorrect. With the New System, however, the drainage tube is always completely full (with a much smaller volume than that of the standard tube), which allows the bladder to remain completely empty and measured urine output to accurately match that of true urine production.

In yet another embodiment of the present invention, the method of preventing airlocks is combined with the method of measuring urine output. This combined method is the only way to ensure that urine output measurements accurately reflect true urine production, as airlocks lead to retained urine in the bladder that is not accounted for in the measurement vessel. One preferred embodiment of this method is the combination of urine output measurement with passive air lock prevention using a vented tube. The vented tube preferably has multiple vents or a continuous vent, as described above, or may comprise an internal vent tube. Another preferred embodiment of this method is the combination of urine output measurement with active air lock prevention using any of the methods described above. However, it should be understood by any person of ordinary skill in the art that the current invention applies to any technique of combining air lock prevention and elimination with any technique to measure urine output. The details disclosed are preferred embodiments, but do not limit the scope of the invention.

In yet another embodiment of the present invention, any potential misalignment of the measurement vessel, which could skew urine output readings, can be detected and accounted for. One such method of accounting for misalignment is to have multiple pressure-sensing tubes at the bottom of the measurement vessel, and to use these results to obtain the correct result. For example, in the simplest case, two pressure-sensing tubes are on either side of the measurement vessel. As the vessel tips to the side, one of the pressure-sensing tubes reads a higher than true pressure and the other reads a lower than true pressure. The difference of these readings can be used to calculate the angle at which the measurement vessel is tipped, and therefore used to account for the misalignment and provide the correct result. Another such method of accounting for misalignment is to have multiple conductive leads around the perimeter of the measurement vessel. Depending which leads have detected the presence of liquid, the angle of misalignment can be calculated and accounted for. Yet another method of accounting for misalignment is to have an accelerometer within the device that continuously measures the angle of tilt.

Figure 24C:
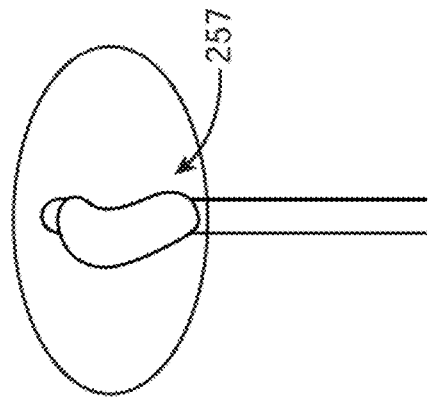
FIGS. 24A-C show alternative retention balloon designs for urine catheters.
Figure 24B:
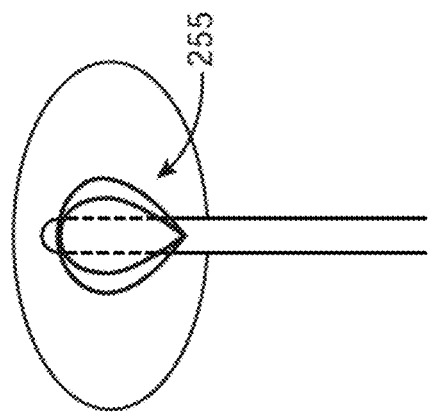
Figure 24A:
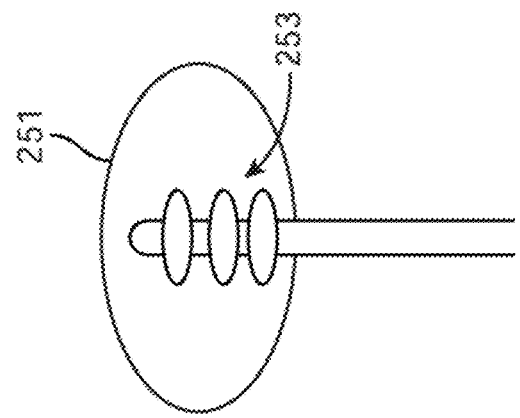

FIGS. 24A-C show alternative retention balloon designs for urine catheters within the bladder 251, comprising one or more balloons to facilitate better urine drainage and decrease the likelihood of becoming obstructed. In one embodiment, shown in FIG. 24A, the balloon comprises two or more separated sections 253, between which are drainage holes, such that tissue intrusion is prevented. In another embodiment, shown in FIG. 24B, the balloon comprises two or more arched members 255 that act as a cage around the drainage holes. In yet another embodiment, shown in FIG. 24C, the balloon comprises eccentric balloon 257 that prevents tissue intrusion into the drainage holes.

Figure 25:
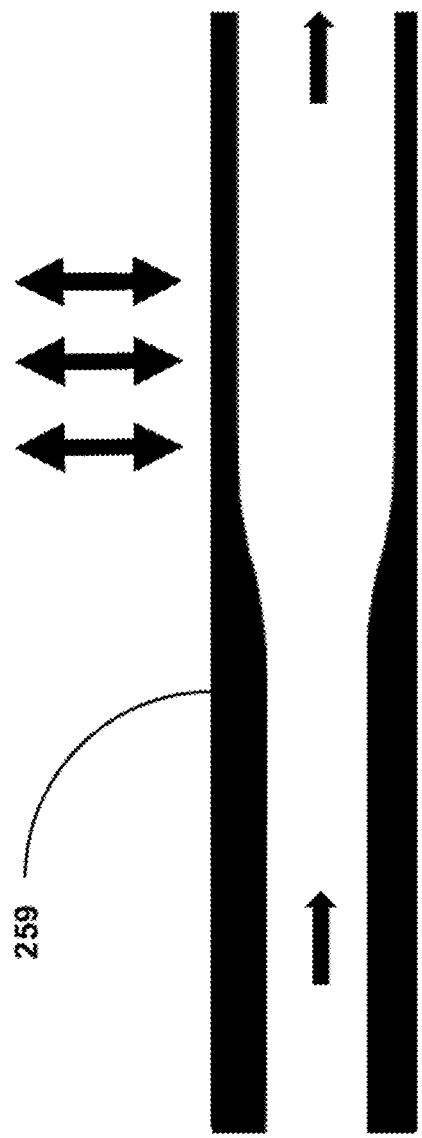
FIG. 25 shows a urine drain tube that allows for partial compression and a motive force based on a vibrating element.

FIG. 25 shows urine drainage tube 259 that allows for partial compression and a motive force based on a vibrating element. In this embodiment, the section of the tube that is subjected to the vibrational or mechanical motive force may be at most around 90% compressed and, therefore, will not have the inherent risk of occlusion that would occur with the stall of a typical pump. Compression may be applied circumferentially or along one or more sides. Compression may be as little as 5% and as much as 90% and may be applied at a point or along a length of the tube. Compression of the tube is, preferably, intermittent and may be of sufficient force to clear blood clots from the urine drain tube.

In yet another embodiment of the present invention, air lock clearance or pumping is performed in a manner such that the path from patient to collection vessel is never completely obstructed. This can be accomplished with any suitable means, including but not limited to using multiple lumens or only partially compressing a lumen, as described above. In this way, the system fails safe by still allowing for urine flow in the event of a system failure.

In yet another embodiment, air locks are prevented by means of a hydrophilic filament that runs the length of the drainage tube and encourage forward movement of the urine via wicking.

Figure 26:
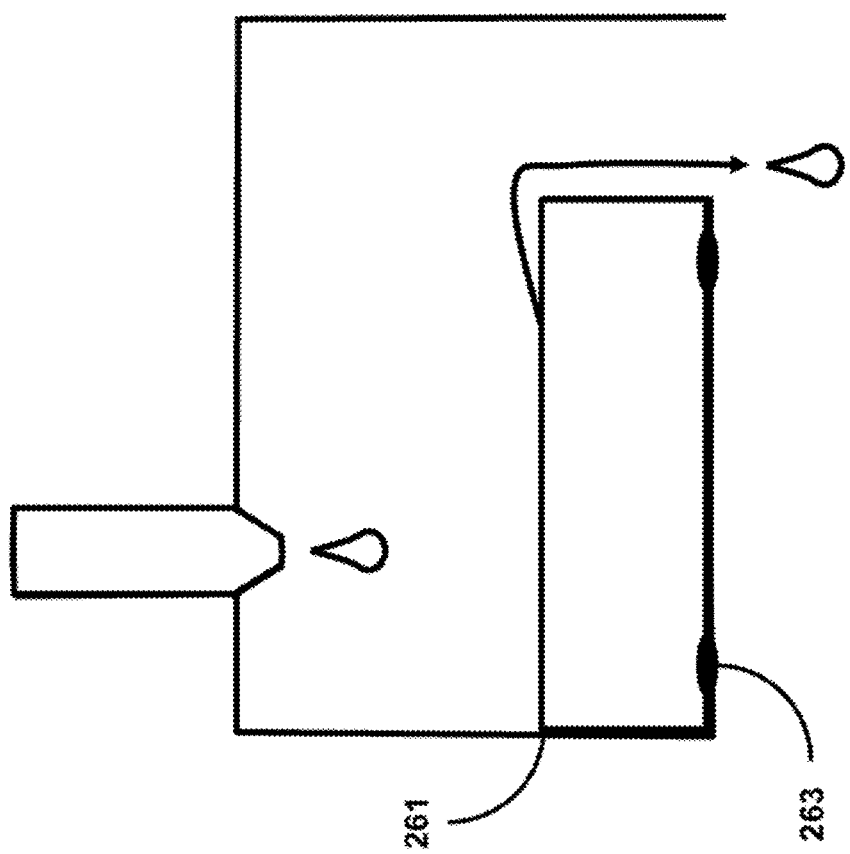
FIG. 26 is an example of a collection reservoir that will not become obstructed with debris, clots or crystals in the urine.

FIG. 26 shows an embodiment of collection reservoir 261 that will not become obstructed with debris, clots or crystals in the urine. In this embodiment (unlike the self-siphoning reservoir) the urine will collect and be continuously pooled and mixed in the collection vessel, before being collected in a urine drain bag. Changes in metabolites, conductance, urinary oxygen tension, specific gravity, etc, will be slower to be reflected in this embodiment, but it will not be subject to the clogging in cases with high protein, blood, debris or crystal content. In order to prevent delays in measurement the volume in the base of the reservoir will, preferably, be minimized with a volume of, at most, 20 cc and preferably as little as 1 cc. The reservoir is preferably disposable and may be instrumented with a pressure sensor connection, conductance electrodes, specific gravity monitor 263, etc.

Figure 27:
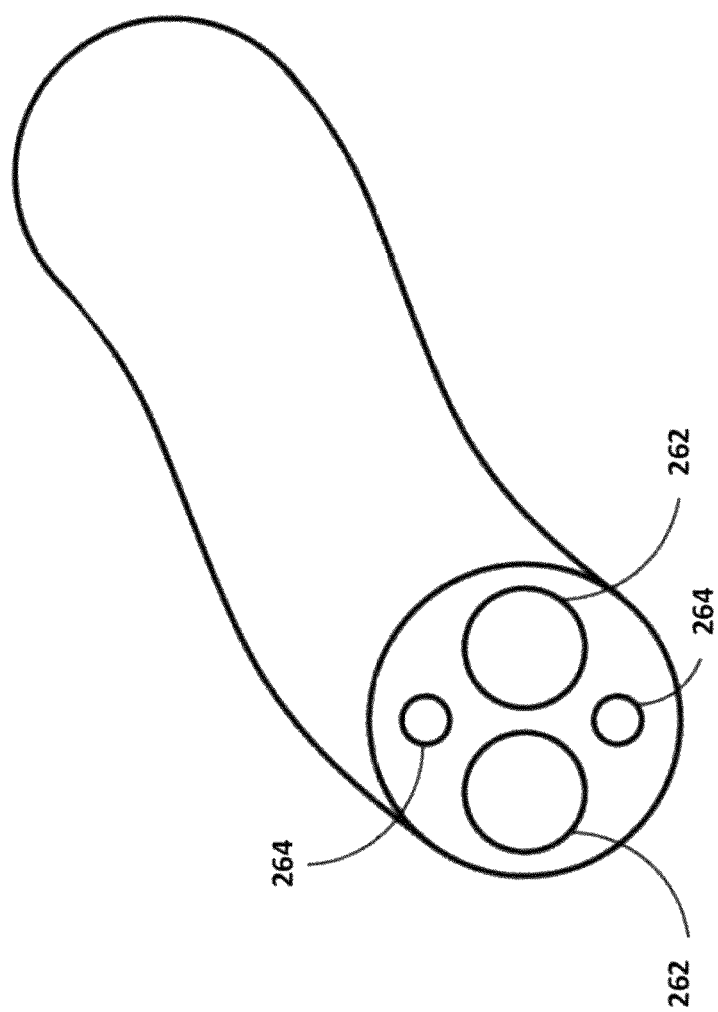
FIG. 27 shows another embodiment of the present invention where the drainage tube has additional lumens beyond those used for drainage.

In yet another embodiment of the present invention, the drainage tube has additional lumens beyond those used for drainage, as shown in FIG. 27, which illustrates the drainage lumens 262 and additional lumens 264. These lumens can be used to measure pressure in the bladder or drainage tube, house a thermistor from the Foley to the console, house wires for detecting the conductivity along the drainage tube for air lock detection, or for carrying/transmitting any additional relevant data to the console.

In yet another embodiment of the present invention, a clamp may be used to temporarily seal the drainage lumen(s) from the patient in order to prevent backflow of urine into the bladder. This clamp may be particularly useful when the patient is being transported and the urine collection vessel may be placed on the bed or held above the level of the bladder.

Figure 28:
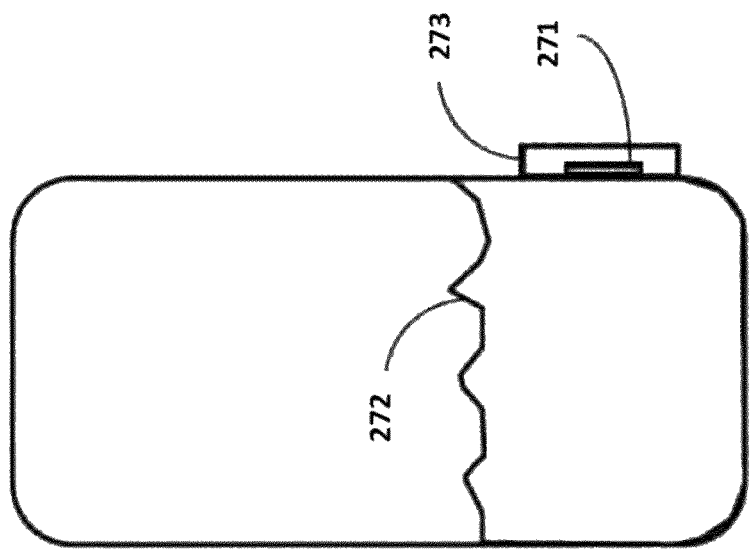
FIG. 28 shows another embodiment of the present invention where measurements of gas partial pressures are made after the gas in the urine has had the chance to equilibrate with gas in a small sample chamber.

In yet another embodiment of the present invention, measurements of gas partial pressures are made after the gas in the urine has had the chance to equilibrate with gas in a small sample chamber. As shown in FIG. 28, this is accomplished by using a gas permeable but liquid impermeable membrane 271 to separate the urine 272 from the gas in the sample chamber 273 and allowing them to equilibrate. Equilibration is performed in one aspect by passive transport between the urine and gas in the sample chamber. In another aspect, the gas is pulled through a looping channel made of the gas permeable membrane in order to maximize the amount of time it has to equilibrate with the urine. In another aspect, the gas is actively pumped into and out of the sample chamber whenever a measurement is taken to prevent contamination between samples. Once equilibration has been achieved, the measurement of the gas pressures is performed with known technologies, such as any means of performing a capnograph to measure carbon dioxide, any means of measuring oxygen (such as a lambda sensor), and any means of measuring the other gases described above.

In another embodiment of the present invention, creatinine clearance can be measured by infusing methylene blue (or any other similar marker) into the patient and measuring creatinine output in their urine. The time until initial detection and rate of clearance give an indication of how well the kidneys are functioning. By synchronizing intermittent infusions of markers with the measurement of these markers in urine, near-continuous information about the kidney function of the patient can be obtained.

Figure 29A:
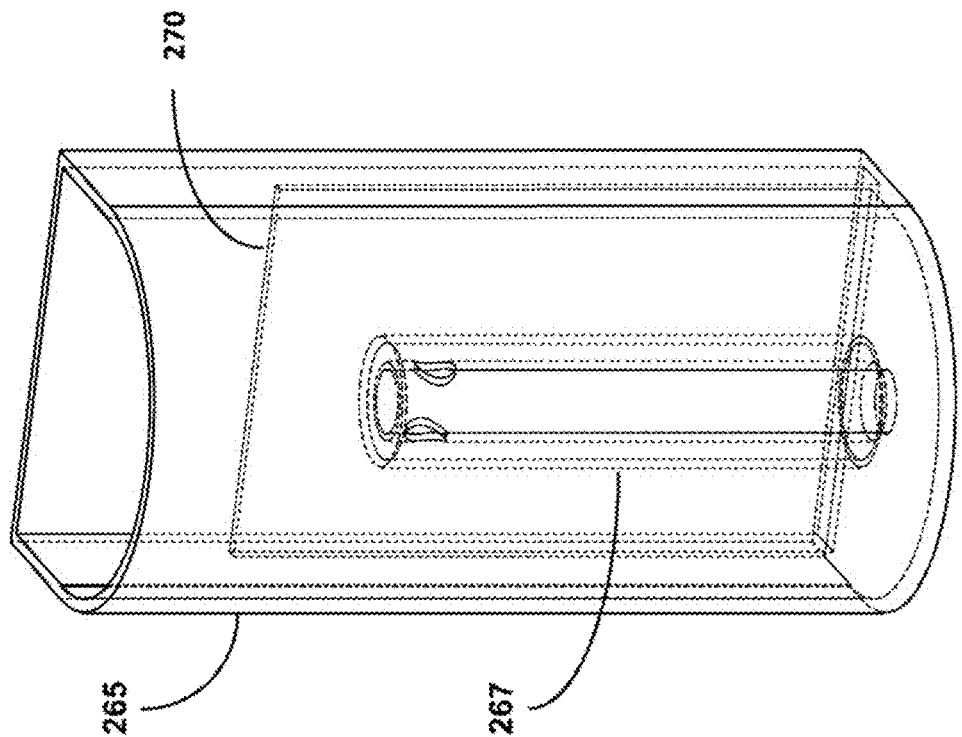
FIGS. 29A-B show embodiments of the sample collection vessels comprising siphon and overflow features.
Figure 29B:
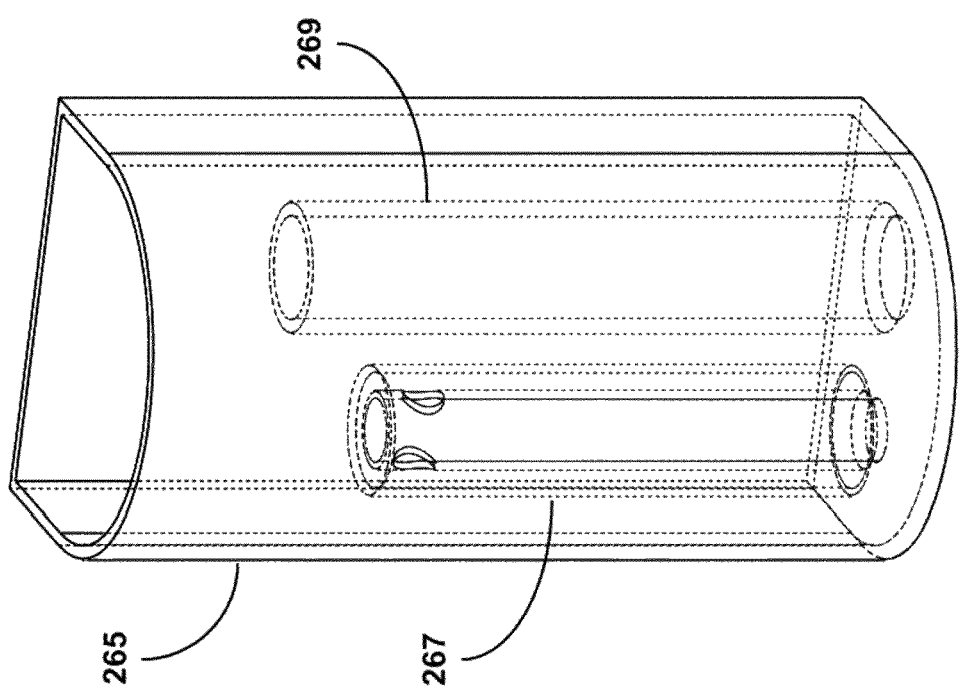

FIGS. 29A-B show embodiments of the sample collection vessels comprising siphon and overflow features. FIG. 29A shows sample collection vessel 265 comprising siphon 267 which, during normal operation should always empty the vessel. An overflow tube will be used if the siphon fails or is clogged, etc.: the urine will pour into overflow tube 269 in order to prevent backup of urine in the vessel. FIG. 29B shows sample collection vessel 265 with siphon 267 and overflow ledge 270. Instead of using a small tube, the overflow is a large "ledge. A large ledge is less likely to become clogged than an overflow tube.

Figure 30B:
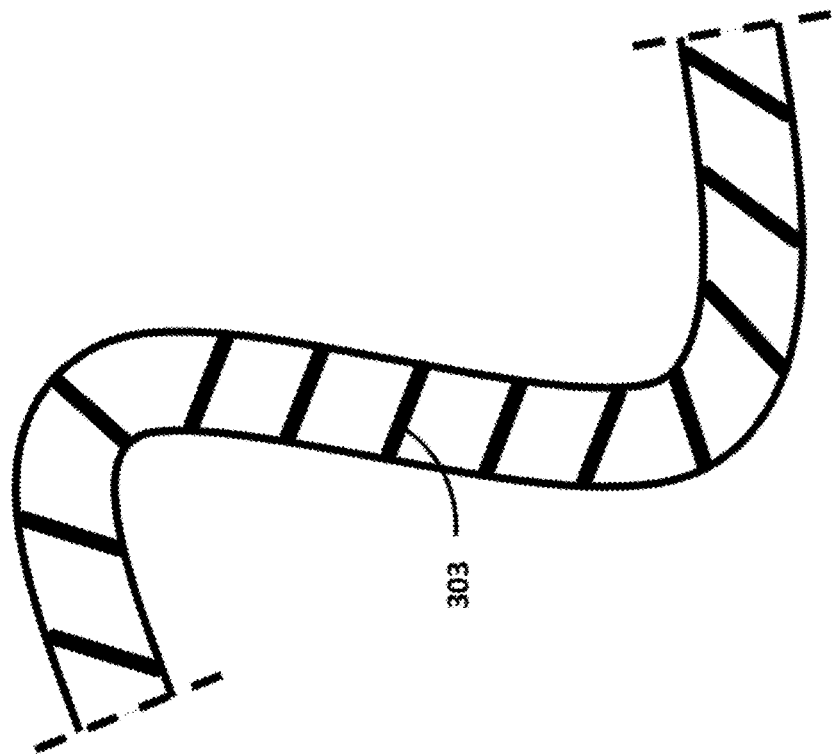
FIG. 30B shows an example of a drainage tube with a spiral vent.
Figure 30A:
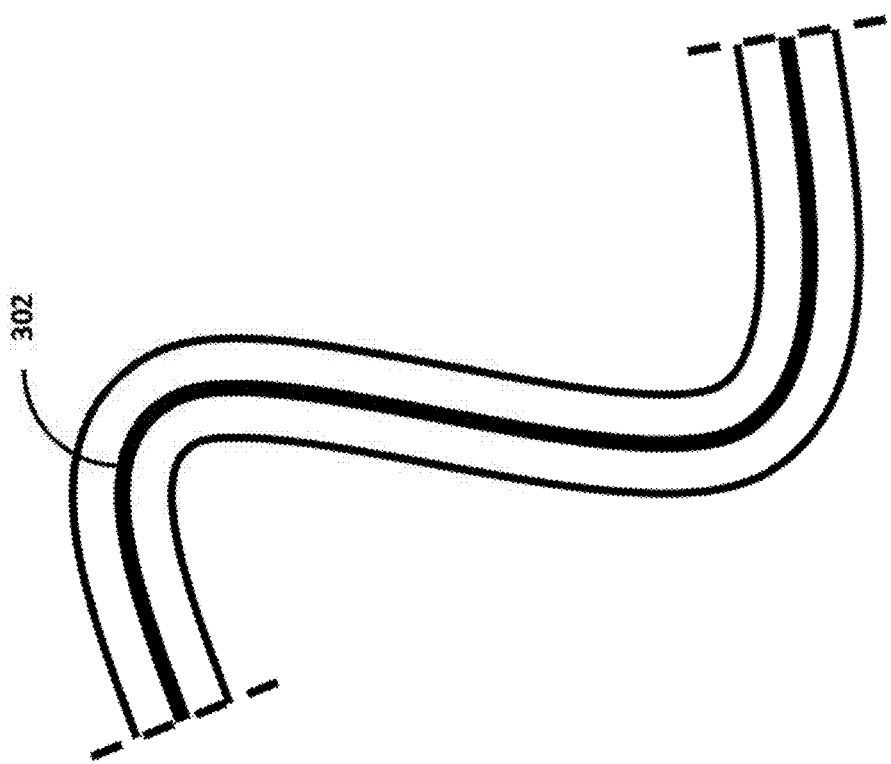
FIG. 30A shows an example of a drainage tube with a slit vent.

In yet another embodiment, the clearing mechanism comprises a tubular hydrophobic vent filter that can be inserted into the drainage lumen of the device such that air will be evacuated throughout its length. A segmental hydrophobic vent can also be incorporated at set intervals to ensure that air is evacuated from the tube as it passes these regions. While others have attempted to prevent air locks with a hydrophobic vent filter at the interface of the Foley catheter and drainage tube, which allows air to escape, this approach may still result in air locks regularly if the vent is not at the zenith of the drainage tube and pointed downward (such that the drainage tube end of the vent is below the Foley catheter side). In some embodiments of the present invention the hydrophobic vent will be interspaced at minimum of 1-2 foot intervals to prevent submersion of at least one or more of the vents in urine. By providing redundancy the present invention prevents failure resulting from all the vents being submerged. The vent or vents may comprise PTFE or ePTFE material and be affixed with a barb and or grommetted into the tube at intervals to allow for easy manufacturability. In an alternative embodiment, the vent comprises one or more slits or spirals that run the length of the drainage tube, thereby allowing air to escape the tube at any point, regardless of the position of the drainage tube, thus preventing airlocks. FIG. 30A shows an example of a drainage tube with slit vent 302, and FIG. 30B shows an example of a drainage tube with spiral vent 303.

Figure 31:
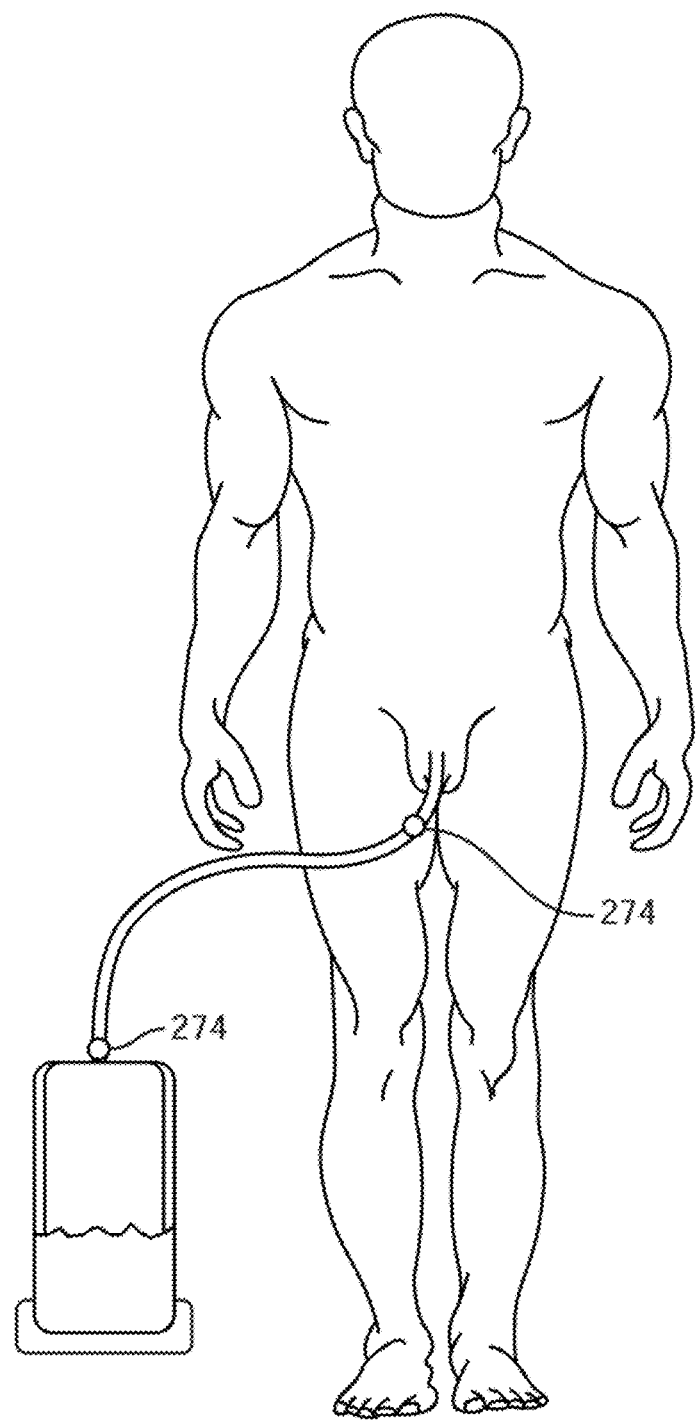
FIG. 31 shows another embodiment where airlock detection occurs using two conductive leads within the drainage tube: one near the patient end and one near the collection chamber.

FIG. 31 shows another embodiment where airlock detection is performed using two conductive leads 274 within the drainage tube: one near the patient end and one near the collection chamber. If the drainage tube is full of urine (not air locked), the resistance between the two leads will be relatively low. If an air lock forms, the resistance will increase significantly, which is detected and the pump is activated to remove the air lock. This feature will allow for the pump to only be activated when necessary and conserve battery power.

Figure 32:
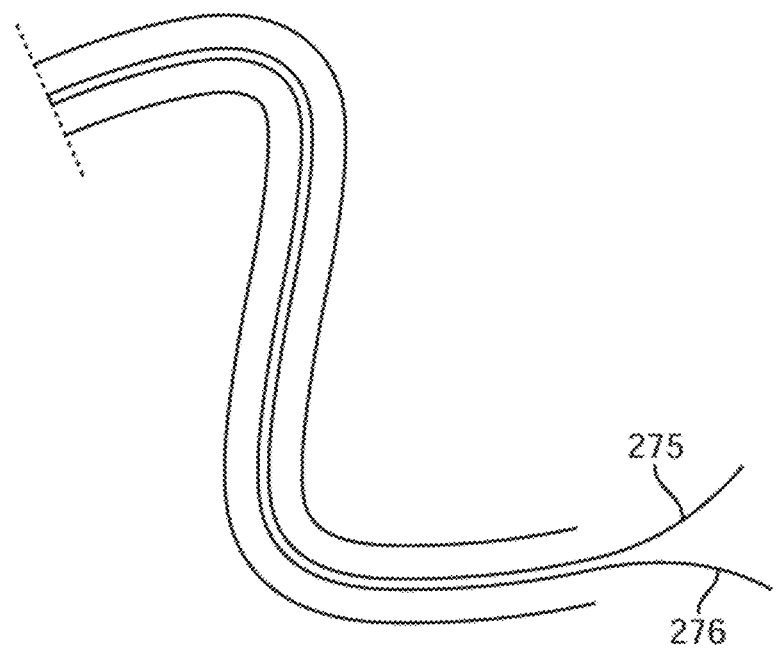
FIG. 32 shows a drainage tube where the wires and pressure lumen run the length of the drainage tube and can connect directly, and in one step, to the reusable box that houses the pump and displays urine output.

In yet another embodiment, a thermistor, thermocouple or similar temperature sensor is included to take measurements of the bladder temperature, which is equal to core body temperature, and the thermistor wire runs along the length of the drainage tube. Currently-used Foley catheters are cumbersome to set up and require multiple steps: the Foley is first attached to the drainage tubing, then additional connections are made to the reusable housing or monitor for temperature, pressure, etc. However, as shown in FIG. 32, if the wires 275 and pressure lumen 276 run the length of the drainage tube, then they could terminate within the measurement vessel and the connections could be made automatically when the vessel is connected to the reusable housing or docking station. The connections for the wires can be secured with snap fits, pogo pins, magnetic connectors, or any other similar means. The connection for the pressure lumen can be secured with a barb and gasket, Luer lock, or any other similar means. The temperature, pressure, and any other data could then be integrated into the display with a single connection step.

Temperature may also be measured in the measurement vessel itself. This measurement is included to account for potential temperature dependencies of the other measurements, such as conductance or oxygen tension. The temperature reading from the sensor is thus included in the algorithm to provide fully calibrated results. The temperature measurement may also be an additional parameter to incorporate into the others to further distinguish between causes of AKI, to detect UTI, to determine the development or status of AKI or to monitor the response the therapy/therapeutic intervention.

In another embodiment, measurements of the described parameters can be obtained with each filling of a 5-10 cc sample collection vessel, which takes a few minutes. Though not continuous, this frequency is effectively as clinically useful as continuous measurements for urine oxygen tension, urine conductance and urine specific gravity. For urine output volume, continuous measurements can be obtained between emptying of the sample collection vessel by means of counting drips, which appear as spikes in the pressure readings. The size of the drips is consistent and known based on the geometry of the drainage line exit. Therefore, continuous measurements of urine output volume can be obtained with drip-rate (sub-cc) precision.

Another embodiment comprises a pressure tube inside a measurement vessel. The pressure tube preferably has a large diameter/cross-sectional area to overcome surface tension effects and to increase the magnitude of the pressure signal. The material of the tube preferably is hydrophobic to reduce surface tension. FIG. 33 shows small float 277 that can be used in pressure tube 278 to completely drain when the siphon drains. As the urine empties, the weight of the float purges the tube.

Figure 34:
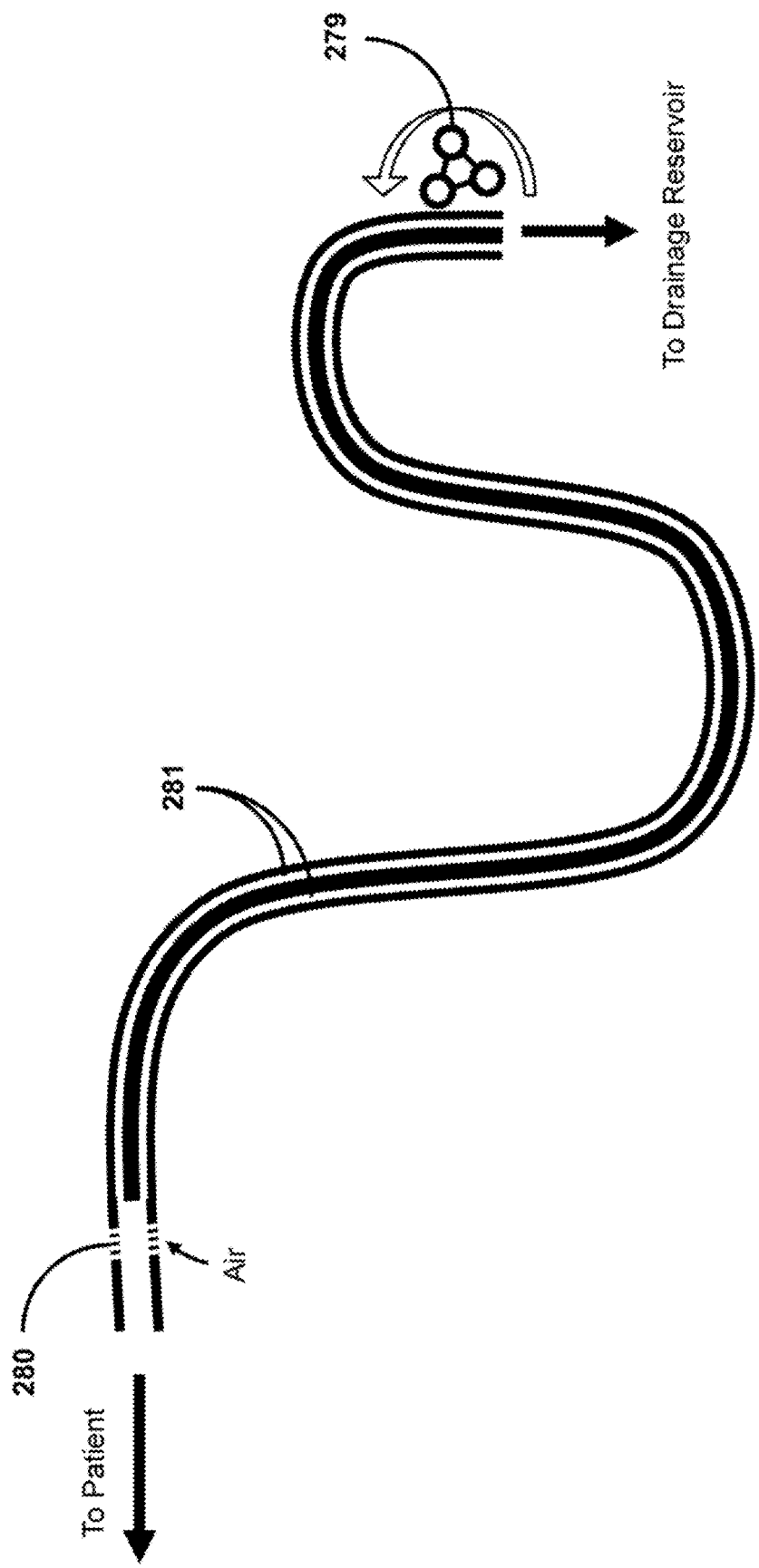
FIG. 34 shows an example of the clearing mechanism in combination with a vent at the proximal (patient) end of the drainage lumens.

FIG. 34 shows an embodiment of the clearing mechanism comprising vent 280 near the proximal (patient) end of the drainage tube that allows air to enter the drainage tube if negative pressure is created either due to a siphon in the drainage tube or due to pumping mechanism 279. Such negative pressure can lead to suction trauma, such as trauma caused to the mucosal lining of the bladder. Note that this is different than the embodiments described above and shown in FIGS. 30A and 30B where the vent(s) allowed air to escape, but not enter, the drainage tube. Drainage lumens 281 preferably have an inner diameter less than 0.25 inches such that liquid in the lumen maintains circumferential contact with the lumen, which forms a seal and allows the liquid to advance when pumping mechanism 279 is activated. There may be multiple drainage lumens 281 to prevent blockage of flow if the pumping mechanism 279 fails. In this embodiment, drainage lumens 281 are preferentially empty, which may require continuous activation of pumping mechanism 279. Alternatively, the pumping mechanism may be activated prior to making a measurement of volume to ensure that all the liquid has been drained, which lengthens the battery life of the device. Preferably, the vent has a resistance to airflow that is greater than the resistance to liquid flow from the patient, such that any buildup of liquid in the patient is purged into the drainage line before air enters through the vent. For example, in the case of urine drainage, a full bladder will be emptied into the drainage line before air enters through the vent as long as the resistance of airflow through the vent is greater than the resistance of urine flowing through the patient's catheter. However, the vent preferably has the smallest possible resistance to airflow while meeting this requirement in order to minimize suction trauma. The pumping mechanism used can be any suitable mechanism, including those described above. Sample mechanisms include a peristaltic-like pump or suction applied directly to the collection vessel. Although FIG. 34 shows the pump on the patient side of the drainage reservoir, the pump may alternatively be on the other side of the drainage reservoir, so that the reservoir is between the patient and the pump.

Although top-vented urine drainage lines do exist, none have small lumens as described above. While they are effective at preventing suction trauma, they are still prone to airlocks whenever the vent is in contact with urine. This leads to retained urine in the bladder and inaccurate urine output measurements. Therefore, in order to prevent suction trauma while also obtaining accurate urine output measurements, the present invention makes use of small lumens and a pumping mechanism in conjunction with a top vent which allows air to enter the drainage line.

In an alternative embodiment, air locks are prevented by means of an extendable drainage tube (not shown), which prevents pockets of air from forming in the high portions of the tube and urine from gathering in the low portions. An extendable tube prevents this from occurring by keeping the tube as straight as possible between the urinary catheter and the collection bag. In one aspect, the extendable drainage tube is composed of multiple telescopic sections that can be extended or collapsed to match the distance from the patient to the collection bag. In another aspect, the drainage tube is pleated to form an accordion, which can be extended or collapsed as necessary. In yet another aspect, the tube is coiled. In yet another aspect, the drainage tube is retractable by means of a spring coil that wraps the tubing around a wheel to achieve the appropriate length.

In another embodiment, air locks are removed by means of a collapsible drainage tube that resides in a stiffer kink-resistant tube (not shown). Periodically, the drainage tube is collapsed, such as by applying a positive pressure to the space between the collapsible tube and the kink-proof tube or by applying negative pressure to the inside of the collapsible tube. Collapsing of the drainage tube then urges urine away from the patient and toward the collection vessel.

In another embodiment, the clearing mechanism comprises a tube with an inner diameter less than 0.25 inches as the drainage tube (not shown), such that no air pockets are able to move up the length of the tube. This is possible due to the surface tension within the smaller tubes, which prevent movement of fluid when one end of the tube is closed to atmosphere (as in the case of the bladder). Thus, the drainage tube always remains full of urine, and for each volume of urine produced the same volume of urine must exit the drainage tube, as urine is incompressible. In another embodiment, the inner diameter is less than 0.125 inches. In another aspect, said drainage tube acts as a siphon and provides a small, safe amount of vacuum to the bladder.

The use of small-diameter tubing also results in a smaller volume of residual urine in the drainage tube compared with the prior art. Having a smaller residual volume is preferential, as it allows urine to move more quickly from the patient's bladder to the collection vessel. The speed of this transport is important in order to take measurements of the urine that has been produced more recently. This is particularly important for patients with low rates of urine production, as it takes their urine even longer to be transported from the bladder to the collection vessel. For example, for a patient producing only 10 mL/hr of urine with a standard drainage tube (around 40 mL residual volume), measurements of their urine in the collection vessel will lag true urine production by 4 hours. By contrast, with smaller tubing (such as tubing having around 5 mL residual volume), measurements will only lag true production by 30 minutes.

Figure 35:
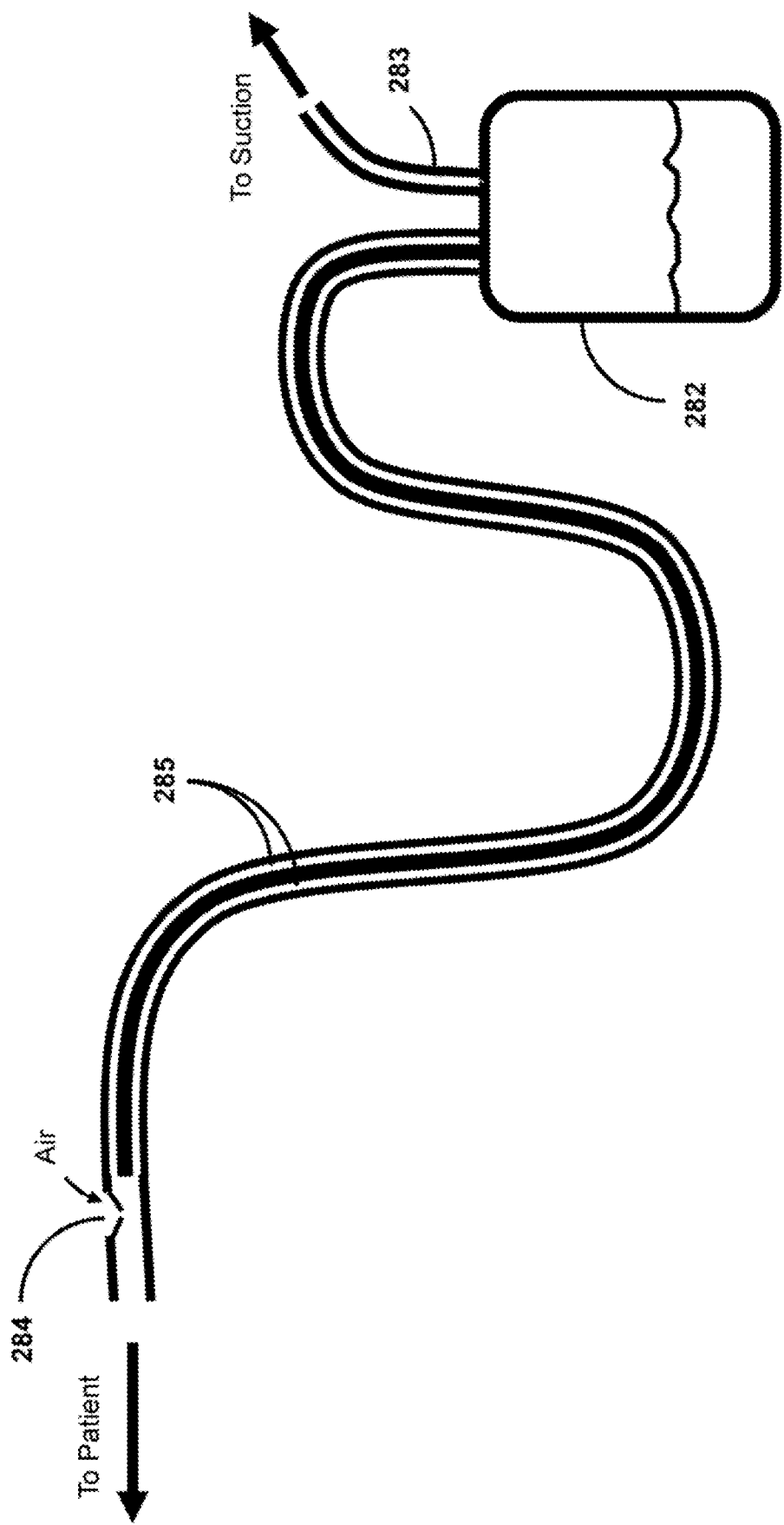
FIG. 35 shows an example of the clearing mechanism in combination with a valve at the proximal (patient) end of the drainage lumens.

FIG. 35 shows an embodiment of the device that is well-suited for draining chest tubes or other drainage tubes that apply constant negative pressure to the patient. Liquid is drained from the patient through drainage lumens 285, which connect to collection vessel 282. Drainage is assisted by pulling negative pressure on the collection vessel 282, for example by attaching a suction tube 283 to the hospital wall suction. Suction may also be applied with other methods, such as with a peristaltic pump 279 illustrated in FIG. 34 or any other suitable pump. Air enters the drainage lumens 285 through a valve 284, which has a crack pressure equal to the desired negative pressure. By choosing the correct crack pressure (for example, −15 to 0 mmHg, or −10 mmHg), the pressure applied to the patient will remain at this pressure as long as the hospital wall suction can generate sufficient suction at the collection vessel 282. Preferably, the drainage lumen(s) used for draining chest tubes are as large as possible while maintaining a siphon. Suitable inner diameters include, but are not limited to, ¼", ⁵⁄₁₆", or ⅜".

Figure 36:
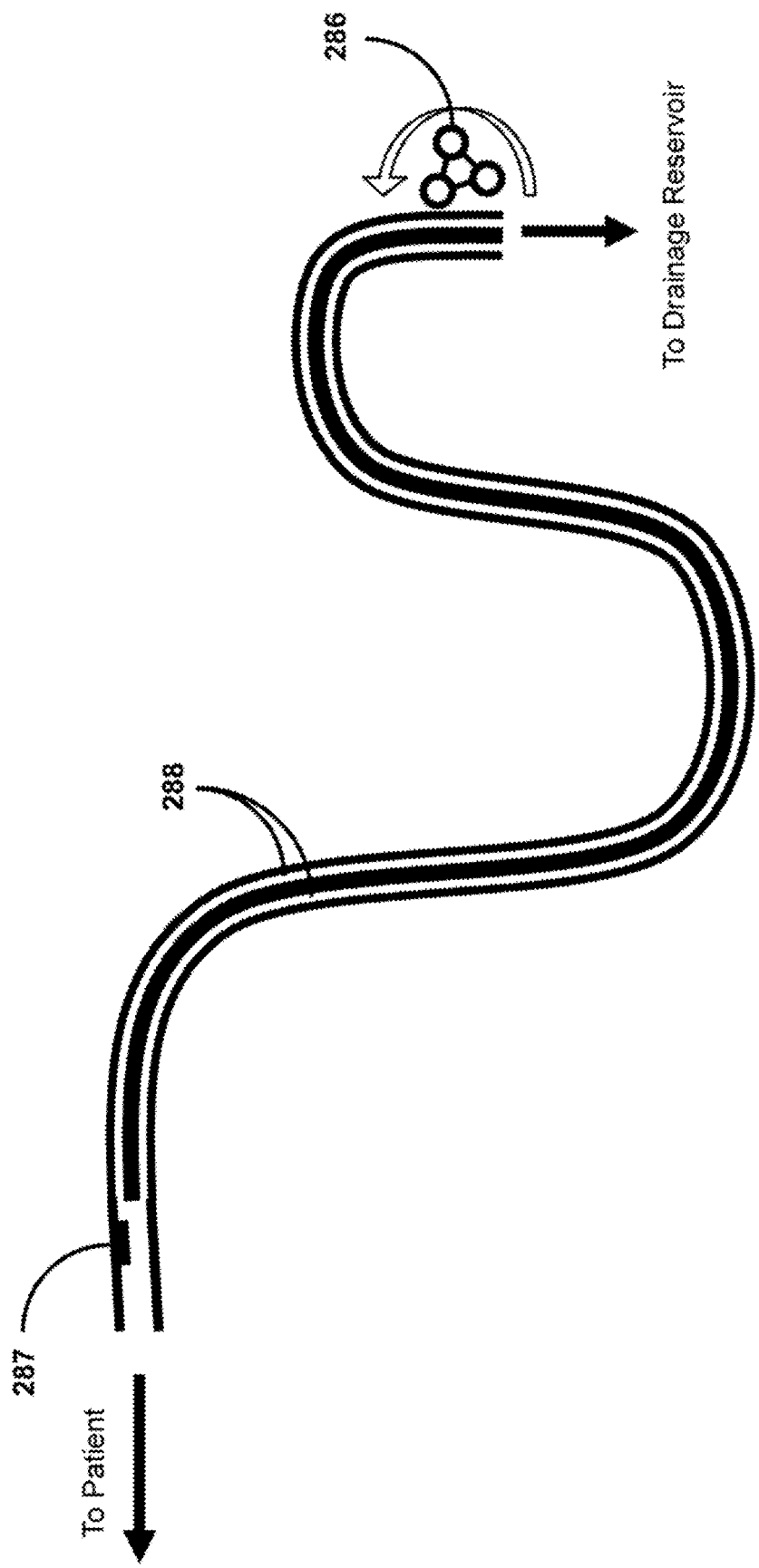
FIG. 36 shows an example of the clearing mechanism in combination with a pressure sensor at the proximal (patient) end of the drainage lumens and closed-loop feedback control of suction.

FIG. 36 shows another embodiment of the device that is well-suited for draining chest tubes or other drainage tubes that apply constant negative pressure to the patient. Liquid is drained from the patient through drainage lumens 288, and negative pressure is applied using a pumping mechanism 286. A pressure sensor 287 resides within drainage tube at the proximal (patient) end, and thereby measures the pressure applied to the patient. The measurement value obtained by the sensor 287 is sent back to the pumping mechanism 286, and the pressure generated by the pumping mechanism 286 is adjusted in order to keep the pressure at the sensor 287 (and patient) at the desired level. The sensor may also be used for passive monitoring of pressure at the patient end of the tube to provide clinicians with information about the level of suction being applied. Although FIG. 36 shows the pump on the patient side of the drainage reservoir, the pump may alternatively be on the other side of the drainage reservoir, so that the reservoir is between the patient and the pump.

In another embodiment of the invention used for draining chest tubes, the volume of the fluid drained is measured in order to provide information to clinicians about the drainage status of the chest tube. This measurement can be accomplished by any suitable means, particularly those described within for measuring urine volume.

In addition to eliminating air locks, several of the air lock clearance designs detailed above have been found to effectively clear deposits and blood clots from urine drainage lines in the bench top model. These problems plague current urine drainage tubes, particularly those with smaller lumen drain tubes and monitoring technologies at the drainage bag, and this invention provides an advance in the state of the art by automating the clearing of these drainage blocking debris and clots. This feature is particularly useful when used in conjunction with pressure sensing either in a balloon at the tip of the Foley or in fluid communication with the bladder. This allows for the monitoring of pressure and vacuum in the bladder and allows for more aggressive pumping based on actual bladder pressure until the clot/obstruction is cleared. Without this pressure/vacuum sensing, the pumping of fluid in the drain tube may generate clinical sequelae in the bladder, such as suction trauma, due to the exposure of the bladder mucosa to excessive vacuum.

Figure 37:
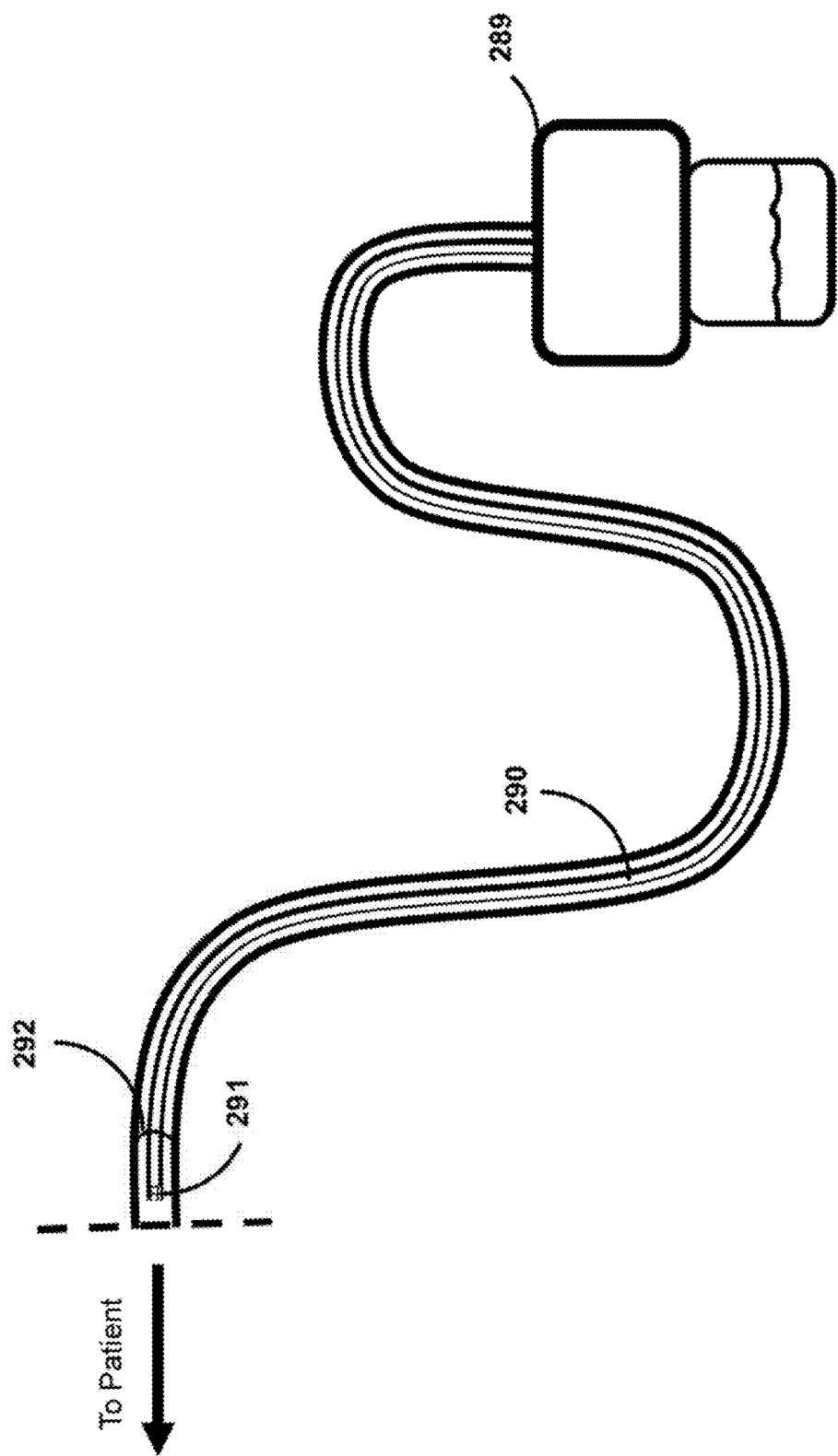
FIG. 37 shows a drainage tube with a gas-sampling lumen that can be used to measure the gas contents of urine before it enters the drainage tube.

In another embodiment, shown in FIG. 37, a gas-sampling lumen 290 runs the length of the drainage tube and terminates with a gas-permeable but liquid-impermeable filter 291 that remains in contact with urine, the meniscus 292 of which is always distal to the filter. When a measurement of oxygen, carbon dioxide, or any other gas is needed, the air within gas-sampling lumen 290 is pulled into base 289 of the drainage device for analysis. This configuration allows for accurate gas analysis even with embodiments of the device that allow air into the drainage line such as those illustrated in FIGS. 34 through 36.

Active Vented System for Draining Bodily Fluids

Figure 38:
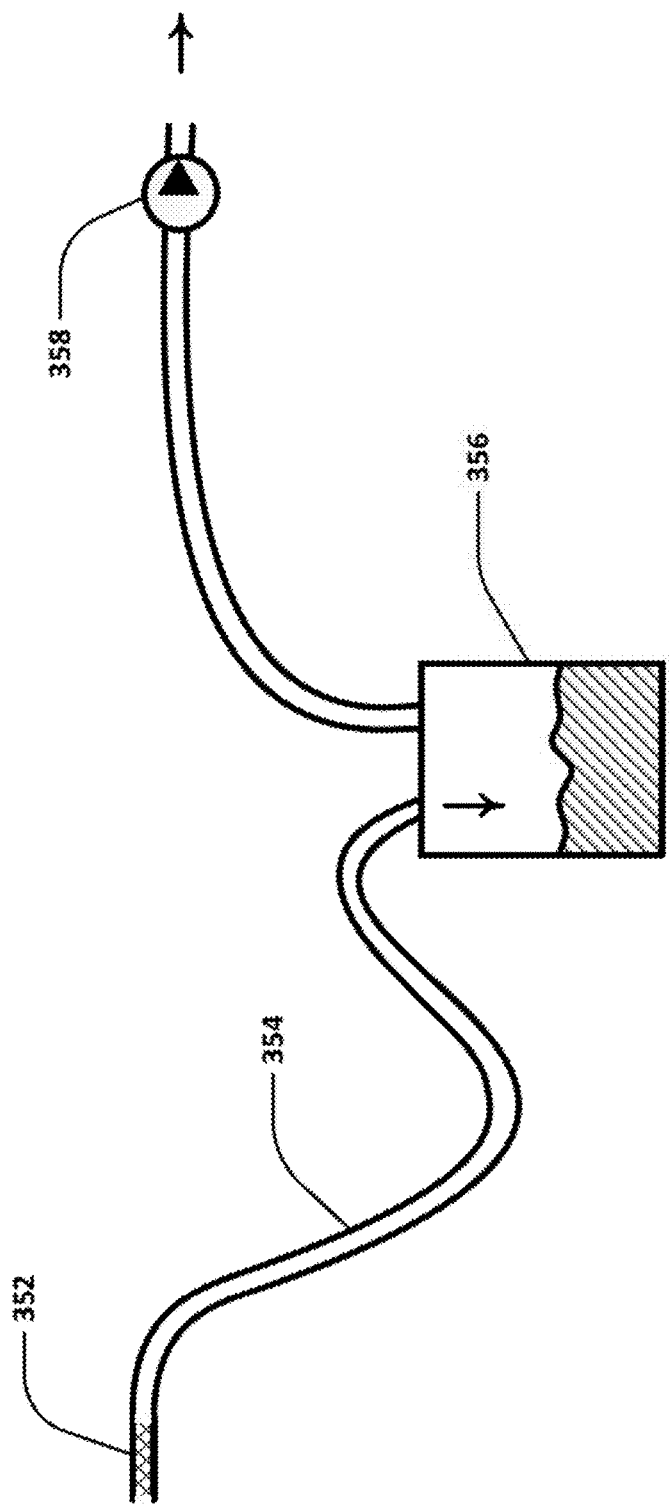
FIG. 38 illustrates the system to drain bodily fluids using an active vent.

As shown in FIG. 38, an active vented system comprises air vent 352, drainage line 354, collection vessel 356, and pump 358. The vented side of the drainage line is connected to the patient. In one embodiment, the fluid drained is urine, and the connection is made to a urinary catheter. Fluid flows from the patient through the drainage line and collects in the collection vessel. The pump in this embodiment is distal to the collection vessel (i.e. not acting directly on the drainage line). The pump facilitates drainage by pulling negative pressure on the collection vessel, which urges fluid through the drainage line. Preferably, the collection vessel is rigid in order to maintain a constant volume when the pump applies negative pressure. The vent on the patient side of the drainage tube is preferably a vent that allows the transmission of gas (preferably air), but prevents the transmission of liquid. The vent thereby prevents substantial negative pressure from being applied to the patient by allowing atmospheric air to enter the system. Such a mechanism prevents suction trauma, for example at the bladder wall.

The pump in this system can be any suitable pump for pumping gases, including, but not limited to peristaltic pumps, diaphragm pumps, or centrifugal pumps. In order to function properly, the pump should preferably be capable of generating negative pressures equal to the maximum liquid column height in the drainage tube. This may be half the length of the drainage tube. With urine drainage tubes having a maximum length of 60 in, the maximum negative pressure required would be around 30 inH2O, or 56 mmHg.

Figure 39:
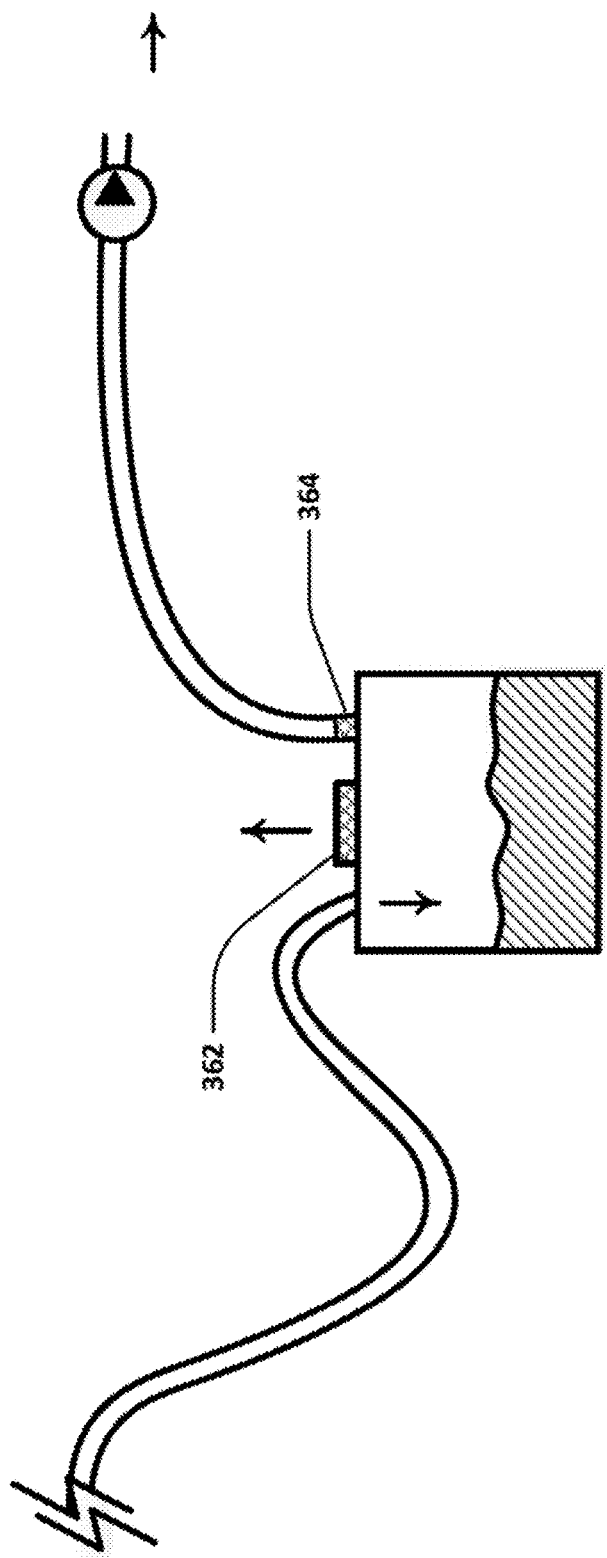
FIG. 39 illustrates the system with additional vents for pressure relief and sterility.

As shown in FIG. 39, an active vented system may have additional vents. One such vent, vent 362, may be located on the collection vessel and allows air to escape the collection vessel. This prevents the buildup of pressure as new fluid enters the vessel, by allowing each volume of fluid entering the system to be offset by the same volume of air exiting the system. Another such vent, vent 364, may be located between the collection vessel and the pump. This vent allows the transmission of gas (preferably air), but prevents the transmission of liquid, in order to prevent bacteria or viruses from entering or exiting the collection vessel and drainage tube. Preferably, this vent is sterility-grade, meaning air that passes through is considered to be sterile. A vent may or may not be present at the patient end of the drainage line (not shown here).

Figure 40:
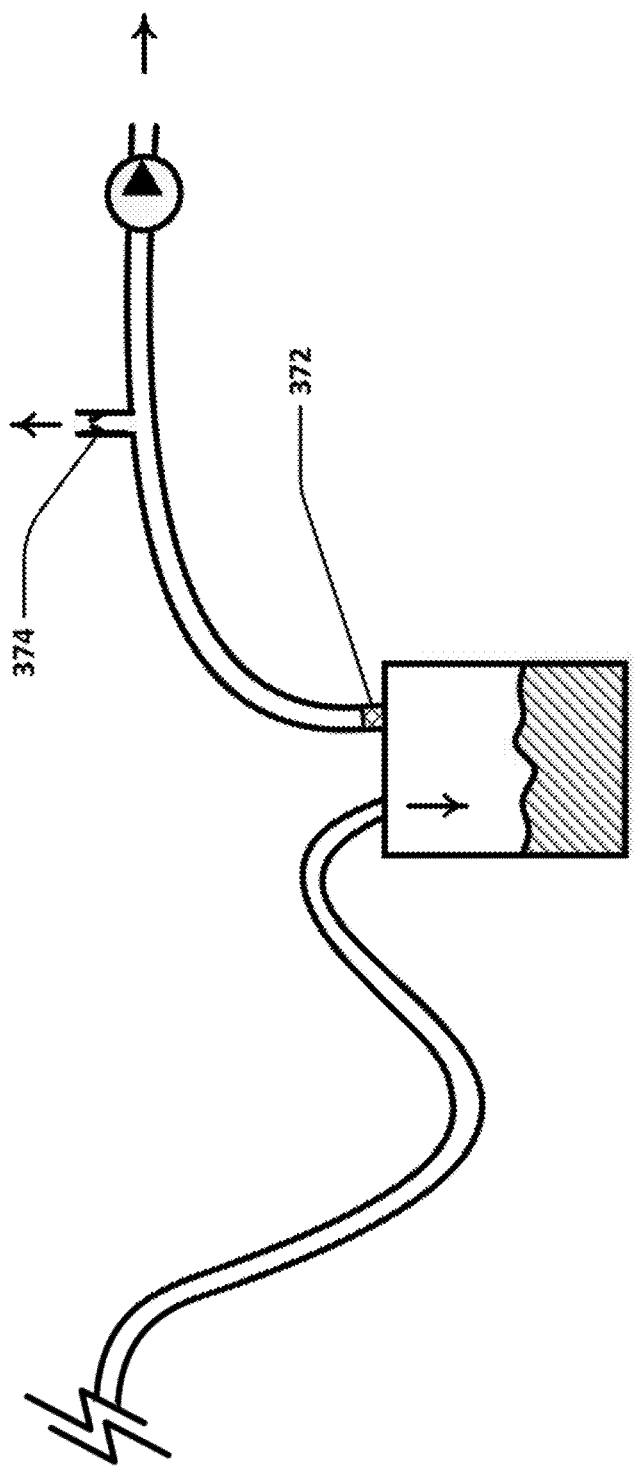
FIG. 40 illustrates the system with a single pressure relief vent and relief valve.

As shown in FIG. 40, pressure offsetting may be accomplished with a single vent on the collection vessel. In this case, the vent, vent 372, may be between the collection vessel and pump as before, but an additional valve 374 allows air to escape the collection vessel in the presence of positive pressure. This valve is preferably a one-way valve that allows air to exit, but not enter, the system. When the pump activates, the one-way valve closes, and air must be pulled from the collection vessel, thereby generating negative pressure in the collection and facilitating flow of fluid through the drainage line. A vent may or may not be present at the patient end of the drainage line (not shown here).

Figure 41C:
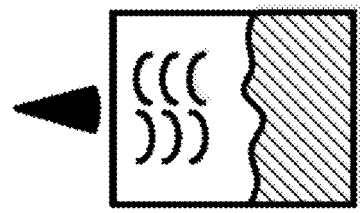
FIGS. 41A-C illustrate exemplary methods of fluid volume measurement with the system.
Figure 41B:
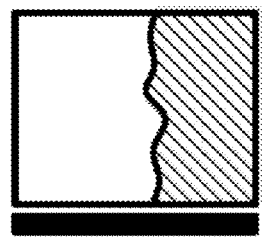
Figure 41A:
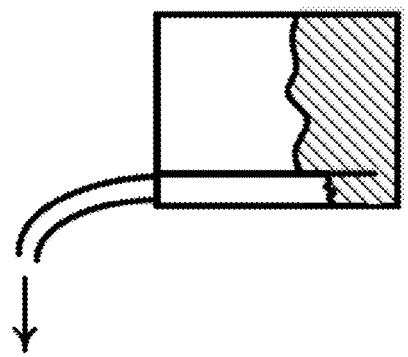

As shown in FIG. 41, the system also preferably has the ability to measure the volume of fluid that has been drained, preferably by means of a pressure sensor (shown in FIG. 41A), capacitive sensor (shown in FIG. 41B), or ultrasonic sensor which may be placed above or below the collection vessel (shown in FIG. 41C). However, any suitable means for measuring fluid volume may be used, more examples of which are outlined in the previous patent filings referenced above.

Figure 42:
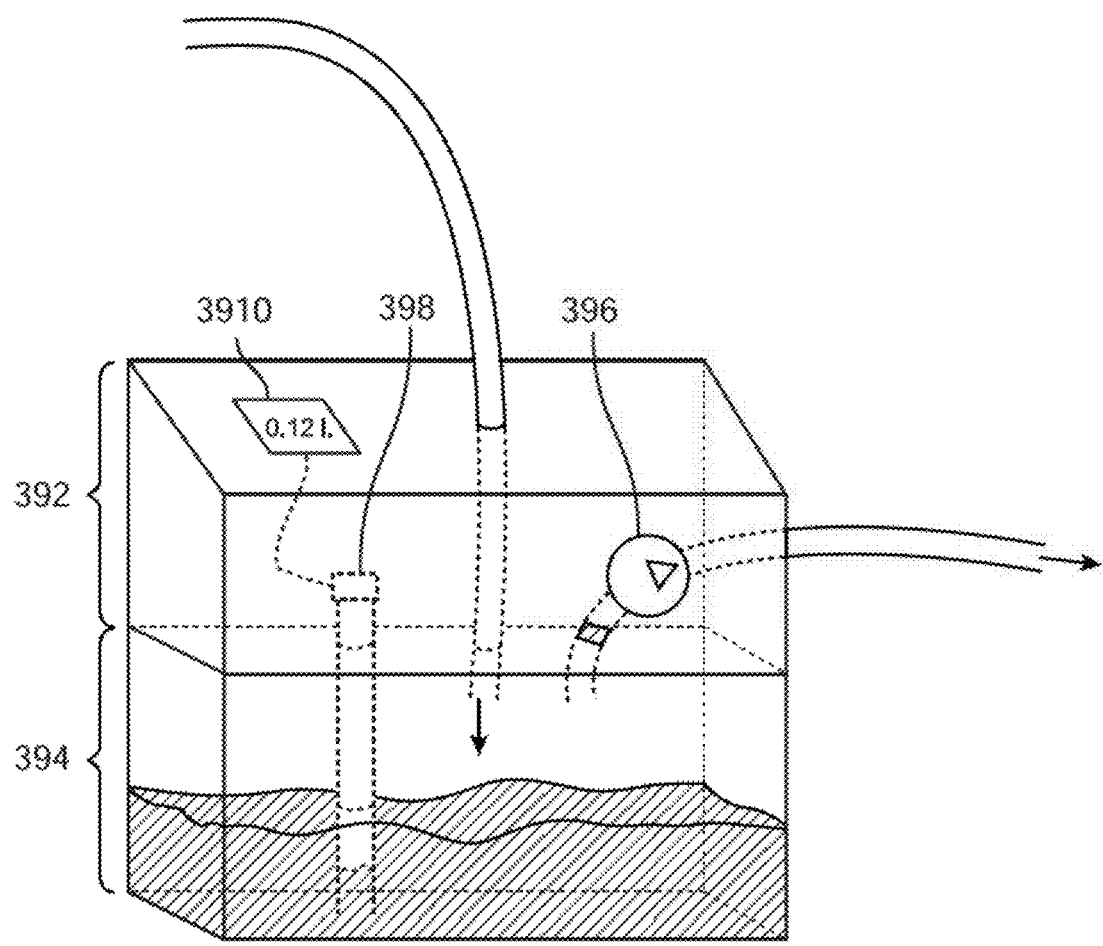
FIG. 42 illustrates the system with modular components (reusable and disposable).

As shown in FIG. 42, the system may be modular, having reusable controller component 392 (to house the electrical components), and disposable measurement vessel component 394 for draining and collecting fluid. The reusable component preferably houses pump 396, volume-sensing mechanism 398 (such as the pressure sensor as shown), screen 3910 to display volume and/or flow, and any other electrical components that may be required, such as a battery, circuit board, and/or microcontroller. The disposable component preferably consists of the patient-side vent, drainage tube, and collection vessel. The reusable and disposable units may be connected with any appropriate means that allows for temporary connection, including, but not limited to, snaps, magnets, hooks, or slots. The pump in the reusable unit may create an airtight seal with the collection vessel using any appropriate means, including, but not limited to, valves, gaskets, and/or Luer fittings.

The vent on the patient side of the drainage tube is preferably made from a membrane that permits the transmission of gases, but not liquids, such as hydrophobic membranes. An example of one such exemplary vent is a PTFE membrane, although other materials may be used. The vent allows air to enter the system when negative pressure is applied to the collection vessel, and air to exit the system when positive pressure is created due to airlocks in the drainage line.

The drainage tube may be any suitable tube for draining bodily fluids, and may be made from any suitable material, including, but not limited to, PVC, silicone, nylon, and polyurethane. The tube preferably has an inner diameter small enough to maintain a meniscus of fluid as it drains (as opposed to fluid dripping down the side of the tube). This inner diameter is preferably less than or equal to ¼ in, and even more preferably less than or equal to 3/16 in. Larger diameter tubing may be used, although more frequent activations of the pump may be required since a new airlock will form with each draining. Small diameter tubing, though still susceptible to airlocks with a vent on the patient side, is much less likely to form airlocks, and therefore requires less frequent activations of the pump. Moreover, the tube preferably has one lumen, but may have multiple lumens, such as 2, 3, or 4 lumens. The tube is preferably clear to allow for visualization of the fluid as it drains.

The drainage container is preferably a rigid container to allow for a negative pressure to form within. Preferably, the container is clear and has rough graduations for volume, in order to allow for the estimation of volume. The container may be made of any suitable material, including, but not limited to, PVC, PMMA, or polycarbonate.

Figure 43:
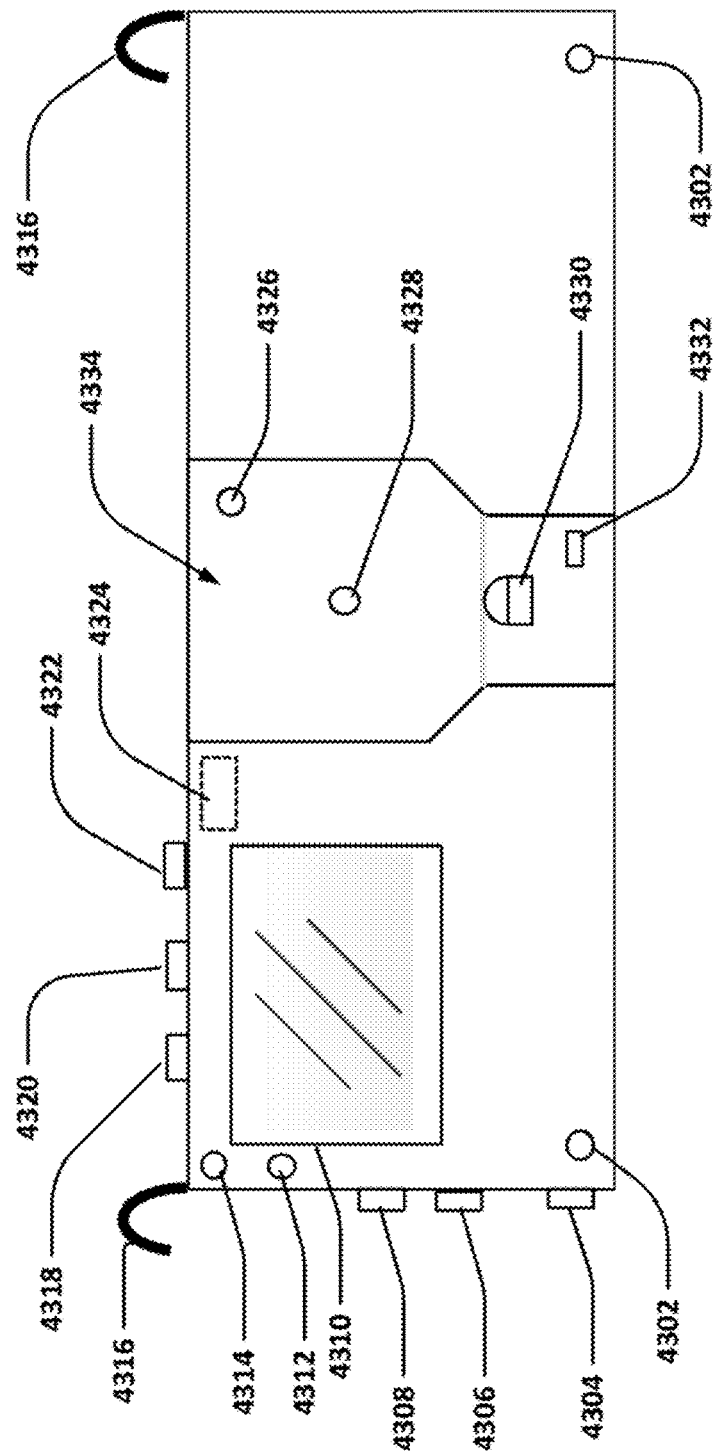
FIG. 43 illustrates a non-disposable controller component of the system.

FIG. 43 illustrates another embodiment of a non-disposable controller component of the system. Disposable measurement vessel or chamber or cassette component is designed to fit into cassette mount 4334 and to interface with the components of the controller. Pump interface 4326 connects to a pump and to a pump interface on the disposable measurement vessel component. The pump is designed to create a vacuum inside the measurement vessel component. Pressure interface 4328 connects to a pressure measurement device and to a pressure interface on the disposable measurement vessel component. The Pressure measurement device is designed to measure the urine, or other fluid, volume measurements. Ultrasonic transducer 4330 is also to provide urine, or other fluid, volume measurements. The ultrasonic measurements can be used in conjunction with the pressure measurements, or either can be used to determine urine, or other fluid, output. Active pinch valve 4332 is designed to connect to the outflow tubing of the measurement vessel. The pinch valve is to control the emptying of the vessel and the pinch valve is controlled by the controller so that it releases urine/fluid when the output reaches a certain volume, as determined by the pressure and/or ultrasonic measurements.

Bed hooks 4316 are to hook the controller to the bed, or other device, as needed. They can also be used to hook the controller to a portable device for patient transport. Collection bag hooks 4302 are to mount a drainage bag where the urine/fluid is ultimately collected, after the urine/fluid passes through the pinch valve.

Screen 4310 is for displaying information including current urine/fluid volume status, system status, etc. Screen 4310 may also be a touch screen and receive inputs, including settings, screen display menu changes, etc. Pressure port 4318 is for connecting the bladder pressure line, which measures bladder pressures using a sensing Foley catheter, if used. Alternatively, the pressure port 4318 takes the form of the other interfaces 4326 and 4328 and is also located within the cassette mount 4334. Temperature in port 4320 is for connecting a thermistor which is measuring body temperature, either via a sensing Foley catheter or by other means. Temperature out port 4322 is for transmitting any temperature measurements to an external device and/or monitor. Adapter port 4324 is for adapting the controller to other devices, such as in the case of a RFID adapter. This could be used to activate any additional/advanced features, such as measurements of IAP, respiratory rate, heart rate, cardiac output, or any other parameters that may be measured by the Burnett catheter. This allows the additional parameters to be activated and paid for by the hospital only when that information is desired.

Power LED/indicator 4314 is an indication that the power is on or off. Error LED/indicator 4312 is an indicator if any error has occurred within the system. Error details can be displayed on screen 4310, but indicator 4312 alerts users that an error exists. Indicators may also incorporate sounds or other alerts.

Port 4308 is for downloads, uploads, software upgrades, connecting to other devices etc. Port 4308 may be a USB port or other appropriate port. SD port 4306 is for data downloads. Power port 4304 is for connecting the controller to the wall or other power source to power the controller.

Figure 44:
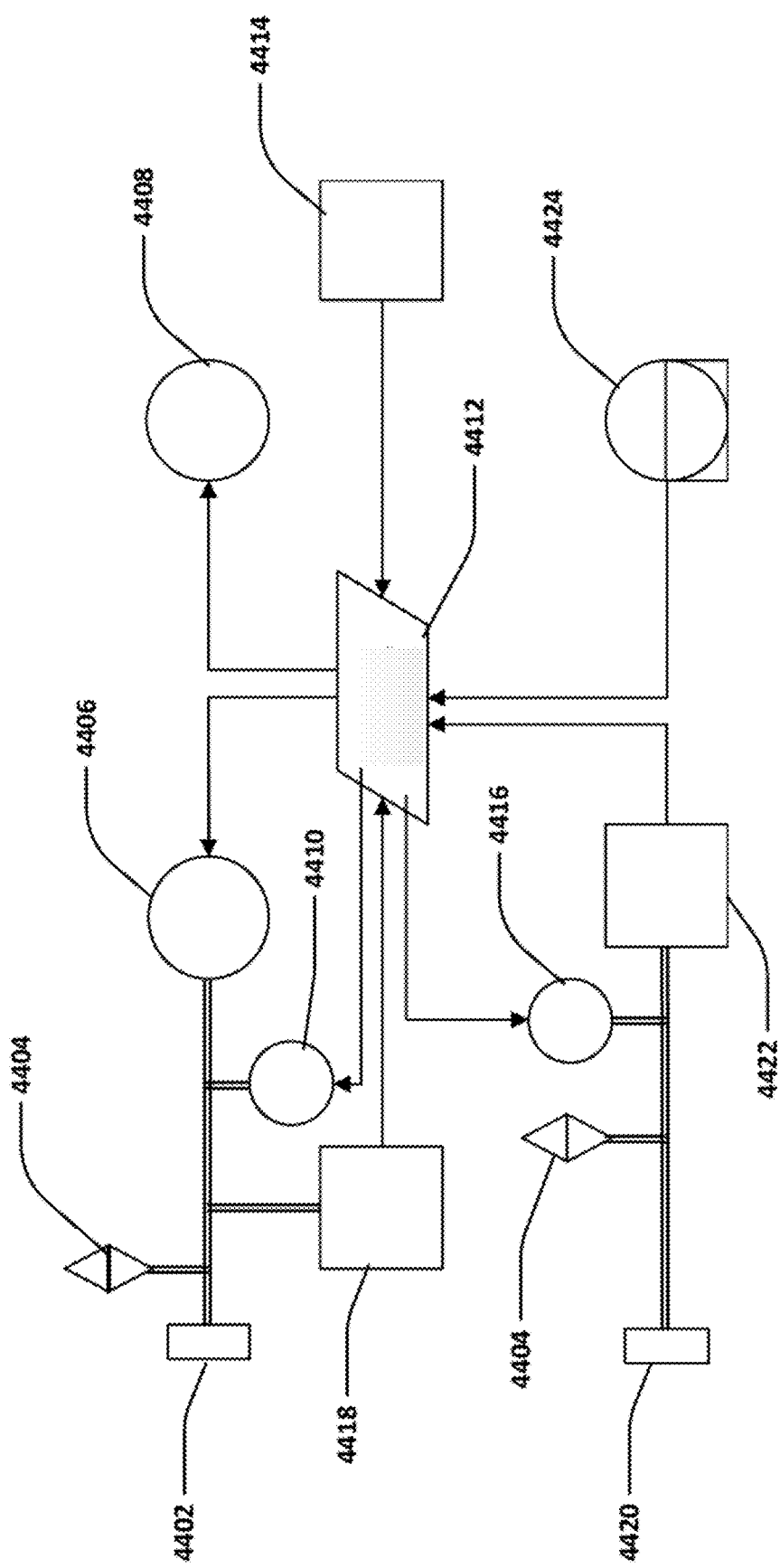
FIG. 44 is a logical diagram of a controller for the system.
Figure 48:
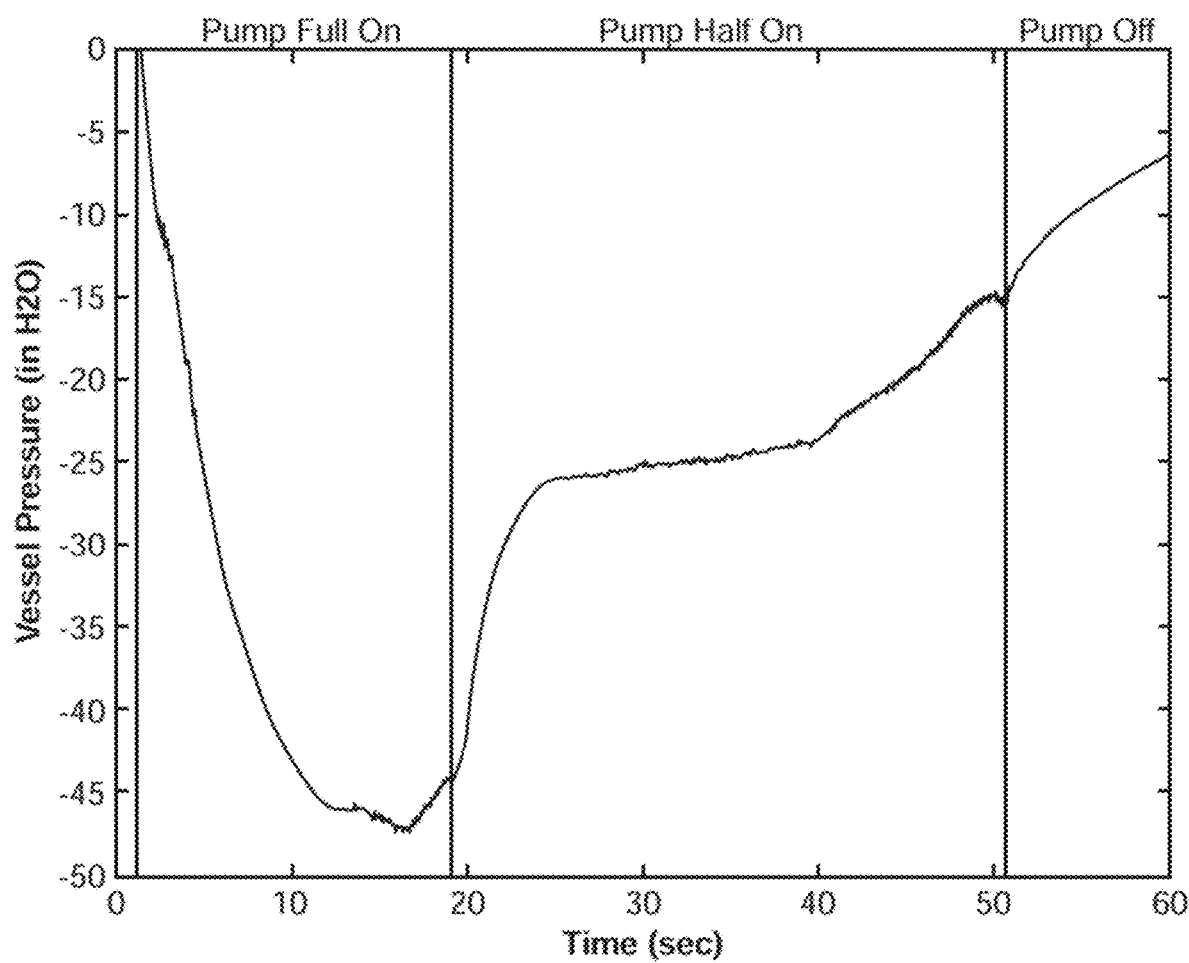
FIG. 48 is a graph of vessel pressure over time with pump usage.

FIG. 44 is a logical diagram of a controller for the system. Pump 4406 represents the pump which connects to pump interface 4326 in FIG. 43. This is the pump which pulls a vacuum on the measurement chamber to clear air locks in the urine drainage line. Pump 4406 connects to pump interface 4326 via pump port 4402. Pump pressure sensor 4418 monitors the pressure within the measurement chamber to determine the status of air lock removal. The reading from pressure sensor 4418 may be used to control pump 4406 in order to prevent substantial negative pressure from being transmitted to the bladder. For example, a graph of what this pressure wave might look like is shown in FIG. 48. Solenoid 4410 is used to relieve pressure/vacuum within the measurement chamber to allow the measurement chamber to fill and empty quickly. Motor 4408 controls pinch valve 4332 shown in FIG. 43. The timing of the opening and closing of the pinch valve may be determined by the volume of liquid within the vessel. Accelerometer 4414 is preferably a 3-axis accelerometer for correcting for any errors due to tilt in the measurement chamber.

Pressure sensor 4422 connects to pressure interface 4328 shown in FIG. 43 via pressure port 4420. Pressure sensor 4422 is used to determine urine/fluid output based on the pressure of the fluid within the measurement vessel/chamber. Puff pump 4416 also connects to pressure interface 4328 via pressure port 4420 and is used to reset pressure based urine/fluid output measurements by providing a "puff" of positive pressure air or gas. This "puff" clears pressure port interface 4420 so that it can provide clean measurements of pressure. Ultrasonic transducer 4424 can also be used to measure urine/fluid output and may be used in conjunction with, or as an alternative to, pressure sensor 4422. Optional safety valves 4404 are in place to protect the pressure sensors by relieving the pressure in the collection vessel in case it becomes extremely high or low. Without these valves, very high or low pressures could damage the pressure sensors. Printed circuit board (PCB) 4412 includes other electrical components, such as a microcontroller, that control/take measurements from the components described above. In another embodiment, puff pump 4416 and pump 4406 may be activated to pump air into vessel 4504 when motor 4408 opens pinch valve 4332 in order to empty vessel 4504 as quickly as possible. Increasing the speed with which vessel 4504 empties is preferable to reduce any errors caused by liquid that enters the vessel as it is emptying and is therefore not captured in the liquid measurements.

Figure 45:
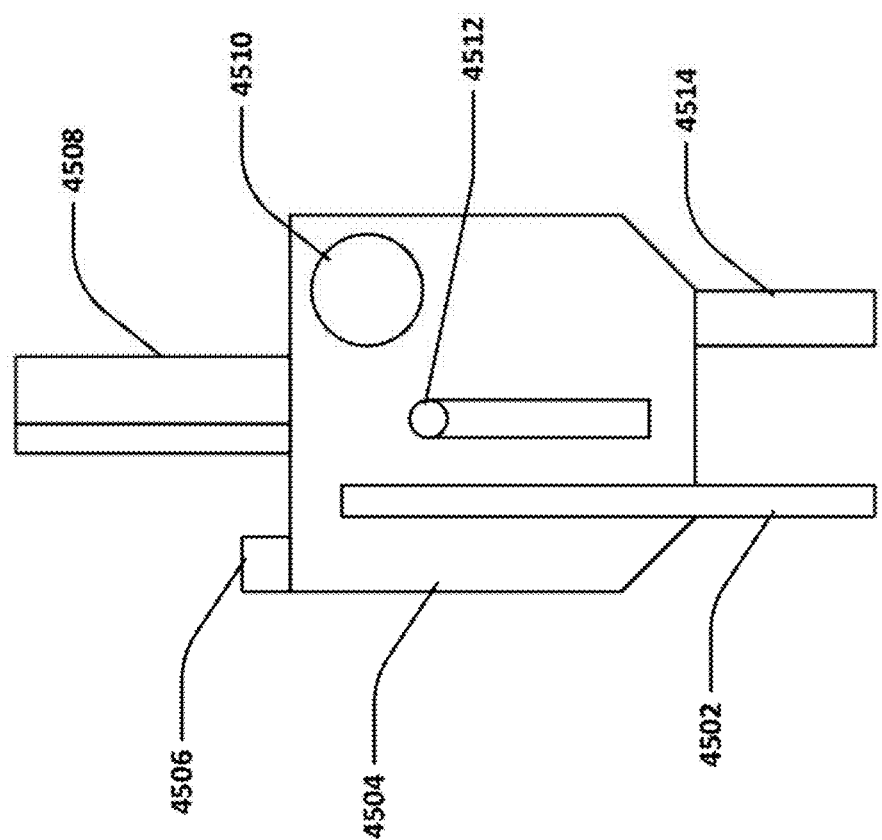
FIG. 45 illustrates a disposable measurement vessel component of the system.

FIG. 45 illustrates a disposable measurement vessel/chamber component of the system. Tapered vessel or chamber 4504 fits into cassette mount 4334 shown in FIG. 43. Urine/fluid flows into the measurement chamber via drainage tube 4508. Drainage tube 4508 may contain one or more lumens. For example, a pressure lumen may exist in addition to a drainage lumen. Other lumens may also exist. Urine/fluid exits the measurement chamber via either outflow tubing 4514, or overflow tubing 4502. Urine/fluid outflow via outflow tubing 4514 is controlled by pinch valve 4332 in FIG. 43. Overflow tubing 4502 is generally not controlled by pinch valve 4332 and is utilized if the programmed emptying cycle is not working properly as a safety measure. Chamber pump interface 4510 connects with controller pump interface 4326 shown in FIG. 43. Pump interface 4510 may have a filter or valve as part of the connector to prevent fluid from crossing the disposable/non-disposable interface. For example, a hydrophobic filter may be used. This pump connected through pump interface 4510 is used to clear airlocks in the urine/fluid drainage tubing. Chamber pressure interface 4512 connects with controller pressure interface 4328 shown in FIG. 43. Pressure interface 4512 may have a filter or valve as part of the connector to prevent fluid from crossing the disposable/non-disposable interface. For example, a hydrophobic filter may be used. Pressure interface 4512 connects with the pressure sensor used for urine/fluid pressure measurements to determine urine/fluid output. Bladder pressure connector 4506 may exist on the disposable fluid measurement chamber, or it may exist on the controller. This pressure connector connects measures bladder pressure via a sensing Foley catheter. This connection may be made in a similar manner to the interfaces 4510 and 4512, especially in the case that drainage tube 4508 has a pressure lumen. Alternatively, the connection may be made with a separate pressure sensing tube that connects from the sensing Foley catheter to the controller with any suitable means, such as a Luer lock or gasket interface. An ultrasonic sensor interface (not shown here) may also be present to measure urine/fluid output.

The vessel container may be made out of Polypropylene. Polyvinyl Chloride. Polycarbonate or other suitable material. The interface filters may be made out of ePTFE, Versapor or other suitable material.

Figure 46:
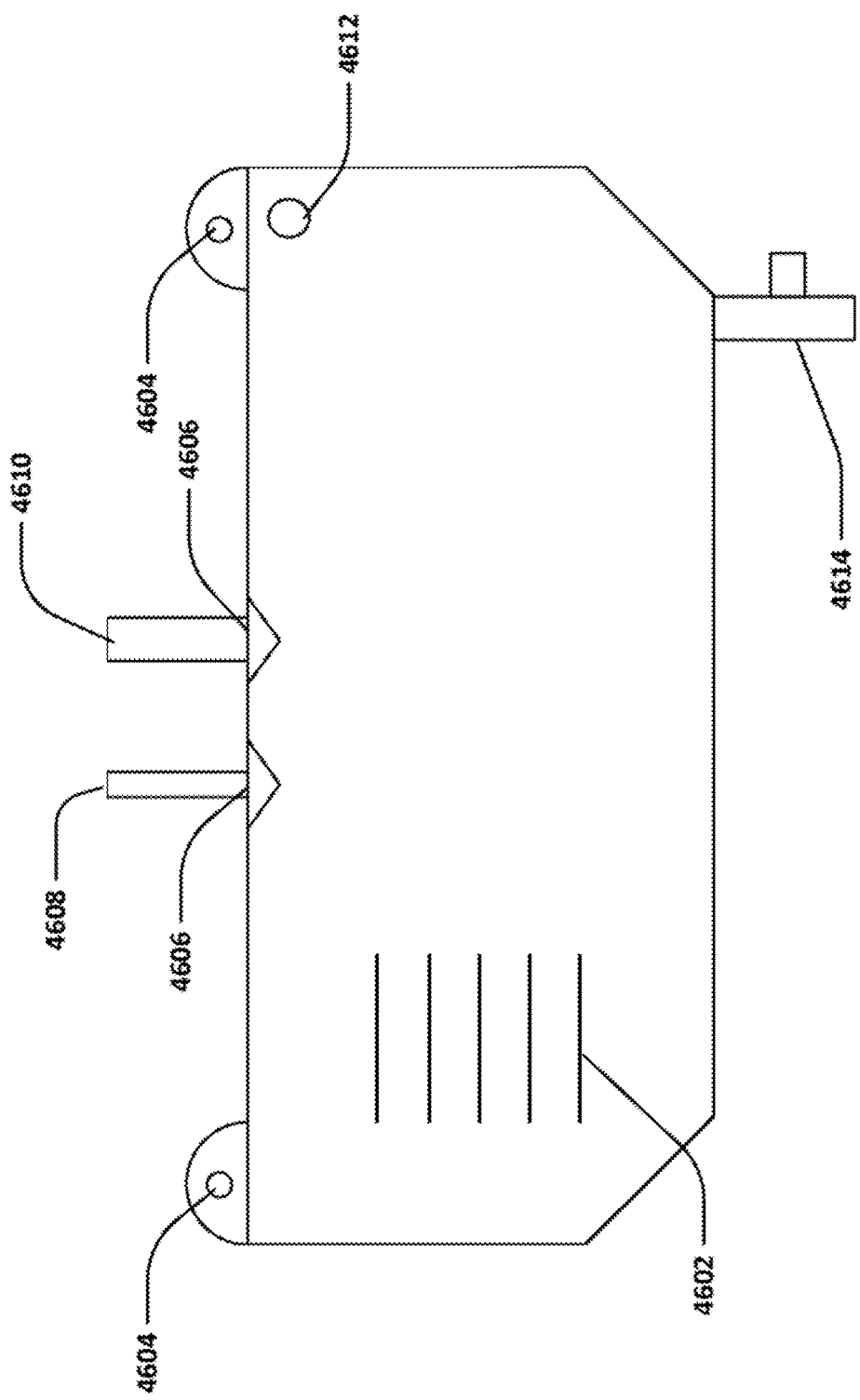
FIG. 46 illustrates a drainage bag.

FIG. 46 illustrates a drainage bag. The drainage bag includes one way valves 4606 connected to overflow tubing 4608 and outflow tubing 4610 to prevent urine/fluid from exiting the drainage bag once collected. These valves also prevent air from entering the collection vessel 4504 when pump 4406 is pulling vacuum so that the vacuum acts on the drainage tubing and not the bag. Mounting holes 4604 mount on to mounting hooks 4302 of the controller shown in FIG. 43. Vent 4612, which may be a hydrophobic or other vent, allows air or gas to exit the drainage bag, but does not allow fluid to exit the bag. This prevents excessive air, and potentially pressure, buildup in the bag, and thus allows for efficient filling of the drainage bag Graduated markings 4602 show a somewhat crude measurement of the fluid volume in the bag as it is collected. Outflow valve 4614 may be used to empty the bag of fluid/urine. Preferably, the valve is operable easily by one person.

The drainage bag may be made out of clear vinyl or other suitable material. The one-way valves may be made out of vinyl or other suitable material. The hydrophobic vent may be made out of ePTFE, Versapor, or other suitable material. The outflow valve may be made out of PVC, PC, or other suitable material.

Figure 47:
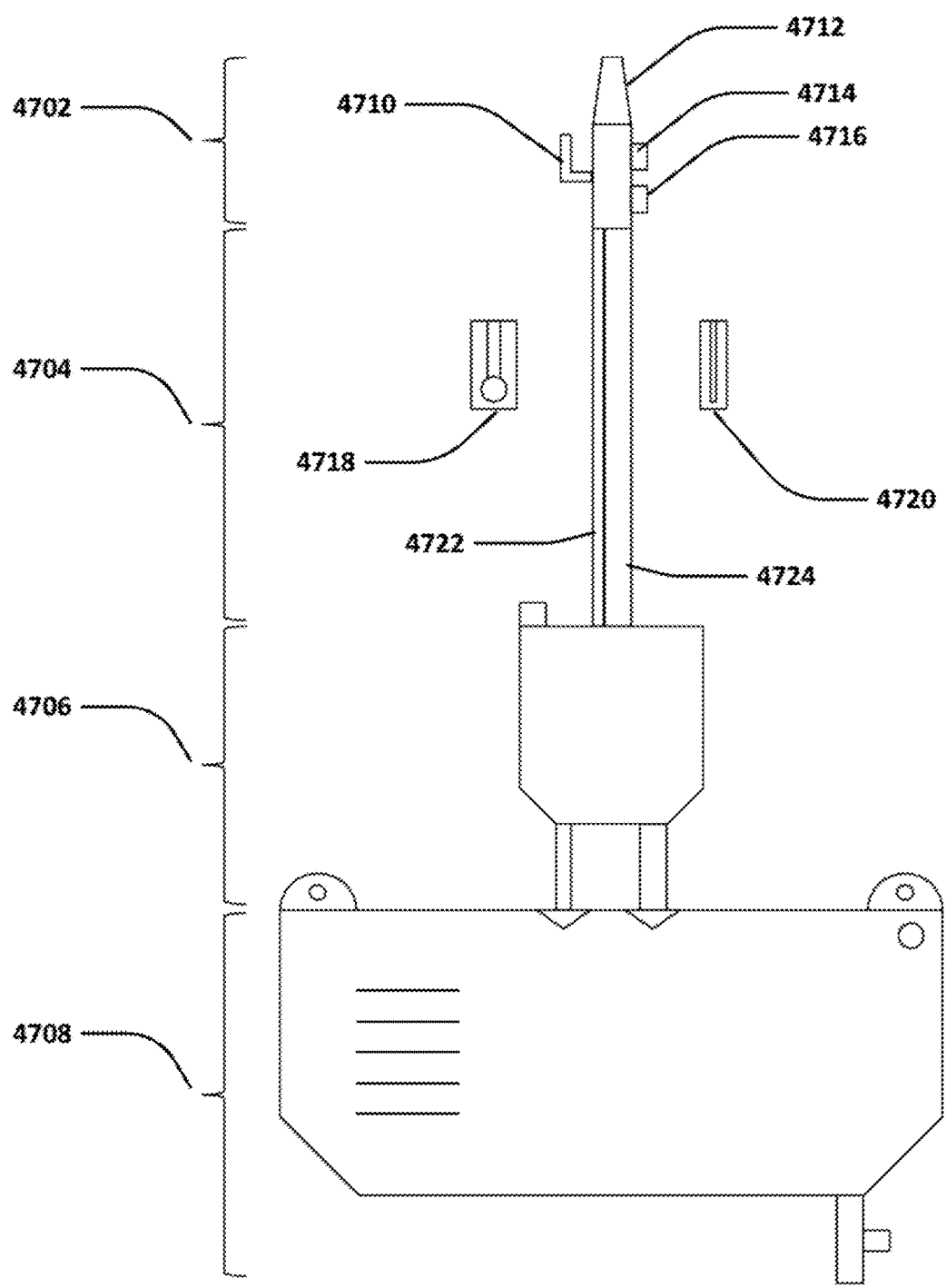
FIG. 47 illustrates an embodiment of the system.

FIG. 47 illustrates an embodiment of the system. FIG. 47 shows how drainage bag 4708, measurement vessel 4706, drainage tubing 4704 and Foley barb 4702 connect. The controller is not shown here. Preferably, the components shown in FIG. 47 are disposable where the controller is not. Drainage tubing may be single or multiple lumens. Here, it is shown with drainage lumen 4724 and pressure lumen 4722. Tubing clamp 4718 and sheet clip 4720 can also be used with the system. Foley barb 4702 may include tapered barb 4712 to connect to the Foley catheter, pressure connector 4710 to connect to the pressure lumen of a sensing Foley catheter, if used, Luer lock valve 4714 used for urine sampling, and vent/valve 4716 to relieve negative pressure in the drainage line. The vent may be a hydrophobic membrane which allows gas, but not fluid, to pass. The valve is a one-way valve which prevents urine from contacting the vent.

FIG. 48 is a graph of vessel pressure over time with pump usage. The first portion of the graph shows the pressure, which is negative because the pump is pulling a vacuum, in the measurement vessel with the pump on full. Note that the pressure "bottoms out" after some time. If the pump were to continue pumping at full power much beyond this point, the pressure transmitted to the bladder could become substantially negative. The second portion of the graph shows the pressure when the pump is only pumping at half power, so the vacuum is not as strong. The third section shows the pressure returning to zero after the pump is turned off. This pressure profile can be monitored by the controller to determine when the pump should be turned on, for how long and at what power. In this way, the system can be programmed to maximize airlock removal, while minimizing negative pressure being applied to the bladder wall which could cause trauma.

Pressure is measured in the collection vessel and used as a feedback mechanism for the pump. For example, the pump may run until the desired level of negative pressure is achieved, after which it shuts off and waits for the fluid to empty completely (as indicated by a rise in pressure back to 1 atm). The pump preferably runs at set intervals, such as every 5, 10, 15, or 60 minutes, according to the desired level of temporal resolution from the physician. Alternatively, the volume measurement system may be used to control the pump. For example, when no flow has been detected for a given amount of time, the pump may be activated.

Example of Data Processing System

Figure 49:
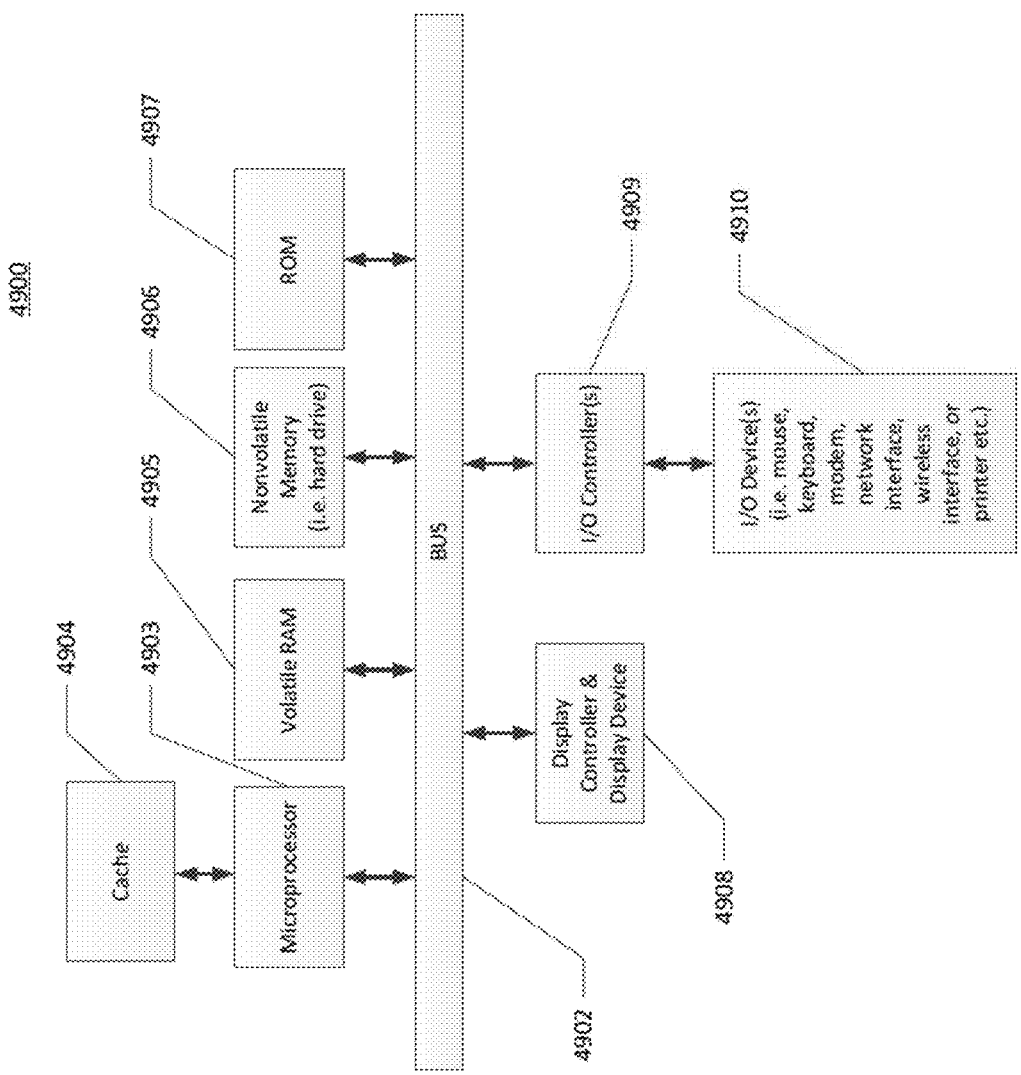
FIG. 49 is a block diagram of a data processing system, which may be used with any embodiments of the invention.

FIG. 49 is a block diagram of a data processing system, which may be used with any embodiment of the invention. For example, the system 4900 may be used as part of a controller. Note that while FIG. 49 illustrates various components of a computer system, it is not intended to represent any particular architecture or manner of interconnecting the components, as such details are not germane to the present invention. It will also be appreciated that network computers, handheld computers, mobile devices, tablets, cell phones and other data processing systems which have fewer components or perhaps more components may also be used with the present invention.

As shown in FIG. 49, the computer system 4900, which is a form of a data processing system, includes a bus or interconnect 4902 which is coupled to one or more microprocessors 4903 and a ROM 4907, a volatile RAM 4905, and a non-volatile memory 4906. The microprocessor 4903 is coupled to cache memory 4904. The bus 4902 interconnects these various components together and also interconnects these components 4903, 4907, 4905, and 4906 to a display controller and display device 4908, as well as to input/output (I/O) devices 4910, which may be mice, keyboards, modems, network interfaces, printers, and other devices which are well-known in the art.

Typically, the input/output devices 4910 are coupled to the system through input/output controllers 4909. The volatile RAM 4905 is typically implemented as dynamic RAM (DRAM) which requires power continuously in order to refresh or maintain the data in the memory. The non-volatile memory 4906 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 49 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 4902 may include one or more buses connected to each other through various bridges, controllers, and/or adapters, as is well-known in the art. In one embodiment, the I/O controller 4909 includes a USB (Universal Serial Bus) adapter for controlling USB peripherals. Alternatively, I/O controller 4909 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks: random access memory; read only memory; flash memory devices; phase-change memory) and transitory computer-readable transmission media (e.g., electrical, optical, acoustical or other form of propagated signals-such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Unless defined otherwise, all technical terms used herein have the same meanings as commonly understood by one of ordinary skill in the medical arts. Specific methods, devices, and materials are described in this application, but any methods and materials similar or equivalent to those described herein can be used in the practice of the present invention. While embodiments of the invention have been described in some detail and by way of illustrations, such illustrations are for purposes of clarity of understanding only, and are not intended to be limiting. Various terms have been used in the description to convey an understanding of the invention; it will be understood that the meaning of these various terms extends to common linguistic or grammatical variations thereof. Further, while some theoretical considerations may have been advanced in furtherance of providing an understanding of the technology, the appended claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims appended to the patent application, including the full range of equivalency to which each element thereof is entitled.

What is claimed is:

1. A device for draining bodily fluids, comprising:
   an elongate body defining one or more lumens configured to receive a bodily fluid from a cavity of a patient body;
   a reservoir in fluid communication with the one or more lumens for receiving the bodily fluid;
   one or more optical sensors in communication with the reservoir for detecting color, opacity, or wavelength specific entities from the bodily fluid received within the reservoir which is configured to self-empty at a predetermined volume such that the one or more optical sensors detect a current value from the bodily fluid;
   a pumping mechanism to urge bodily fluid through the one or more lumens and positioned distal to the reservoir, wherein the pumping mechanism is configured such that bodily fluid through the one or more lumens remains unobstructed to maintain an open space within the one or more lumens; and
   a vent or valve mechanism in communication with the elongate body and configured to allow air to enter or exit the one or more lumens such that outflow of the bodily fluid through the one or more lumens remains unobstructed and a negative pressure buildup in the cavity is inhibited.

2. The device of claim 1 wherein the pumping mechanism comprises a peristaltic, diaphragm, or centrifugal pump.

3. The device of claim 1 wherein the pumping mechanism is further configured to generate a negative pressure to overcome a maximum liquid column height in the elongate body.

4. The device of claim 1 wherein the one or more lumens each define an interior diameter sized to maintain a siphon or continuous fluid path between the cavity and the reservoir.

5. The device of claim 4 wherein the interior diameter is less than 0.25 inches such that the bodily fluid within the one or more lumens maintains circumferential contact with the one or more lumens.

6. The device of claim 4 wherein the interior diameter is less than 0.125 inches such that the bodily fluid within the one or more lumens maintains circumferential contact with the one or more lumens.

7. The device of claim 1 further comprising a controller in communication with at least the pumping mechanism.

8. The device of claim 7 wherein the controller is configured to determine a volume of the bodily fluid.

9. The device of claim 8 wherein the controller is configured to determine the volume via a measurement of a fluid pressure or ultrasound.

10. The device of claim 7 wherein the controller is configured to determine a fluid pressure within the cavity of the patient body.

11. The device of claim 7 wherein the controller is configured to control the pumping mechanism in response to a pressure measurement from within the reservoir or cavity of the patient body.

12. The device of claim 1 wherein the reservoir is configured to measure a fluid pressure within.

13. The device of claim 1 further comprising at least a second vent or valve in communication with the reservoir.

14. The device of claim 1 wherein the vent or valve is configured for unidirectional flow.

15. The device of claim 1 wherein the vent or valve is configured to have a resistance to airflow that is greater than a resistance to a flow of the bodily liquid from the cavity of the patient body such that bodily fluid is purged into the elongate body prior to air entering through the vent or valve.

16. The device of claim 1 wherein the vent or valve has a crack pressure of −15-0 mmHg.

17. The device of claim 1 wherein the reservoir is configured for measuring a volume of the bodily fluid.

18. A method for draining bodily fluids, comprising:
    positioning an elongate body defining one or more lumens within a cavity of a patient body such that the one or more lumens receive a bodily fluid from the cavity;
    actuating a pumping mechanism to urge the bodily fluid through the one or more lumens from the cavity such that outflow of the bodily fluid through the one or more lumens remains unobstructed;
    flowing air into or from the one or more lumens via a vent or valve mechanism located between a reservoir and the cavity and in communication with the elongate body such that outflow of the bodily fluid through the one or more lumens remains unobstructed and negative pressure buildup within the cavity is inhibited;
    receiving the bodily fluid in the reservoir which is in fluid communication with the one or more lumens;
    detecting color, opacity, or wavelength specific entities from the bodily fluid received within the reservoir via one or more optical sensors in communication with the reservoir; and
    self-emptying the reservoir at a predetermined volume such that the one or more optical sensors detect a current value from the bodily fluid within the reservoir.

19. The method of claim 18 wherein actuating a pumping mechanism comprises actuating a peristaltic, diaphragm, or centrifugal pump.

20. The method of claim 18 wherein actuating a pumping mechanism comprises generating a negative pressure to overcome a maximum liquid column height in the elongate body.

21. The method of claim 18 wherein the one or more lumens each define an interior diameter sized to maintain a siphon or continuous fluid path between the cavity and the reservoir.

22. The method of claim 21 wherein the interior diameter is less than 0.25 inches such that the bodily fluid within the one or more lumens maintains circumferential contact with the one or more lumens.

23. The method of claim 21 wherein the interior diameter is less than 0.125 inches such that the bodily fluid within the one or more lumens maintains circumferential contact with the one or more lumens.

24. The method of claim 18 wherein actuating a pumping mechanism further comprises controlling the pumping mechanism via a controller in communication with at least the pumping mechanism.

25. The method of claim 24 wherein the controller is configured to determine a volume of the bodily fluid.

26. The method of claim 24 wherein the controller is configured to determine the volume via a measurement of a fluid pressure or ultrasound.

27. The method of claim 24 wherein the controller is configured to determine a fluid pressure within the cavity of the patient body.

28. The method of claim 24 wherein the controller is configured to control the pumping mechanism in response to a pressure measurement from within the reservoir or cavity of the patient body.

29. The method of claim 18 further comprising measuring a fluid pressure within the reservoir.

30. The method of claim 18 further comprising at least a second vent or valve in communication with the reservoir.

31. The method of claim 18 wherein the vent or valve is configured for unidirectional flow.

32. The method of claim 18 wherein the vent or valve is configured to have a resistance to airflow that is greater than a resistance to a flow of the bodily liquid from the cavity of the patient body such that bodily fluid is purged into the elongate body prior to air entering through the vent or valve.

33. The method of claim 18 wherein the vent or valve has a crack pressure of −15-0 mmHg.

34. The method of claim 18 further comprising measuring a volume of the bodily fluid within the reservoir.

* * * * *